United States Patent
Zhang et al.

(10) Patent No.: US 7,960,373 B2
(45) Date of Patent: Jun. 14, 2011

(54) 2-ALKOXY-3,4,5-TRIHYDROXYALKYLA-MIDE-BENZOTHIAZEPINES PREPARATION THEREOF, COMPOSITIONS CONTAINING THEM AND USE THEREOF

(75) Inventors: Jidong Zhang, Paris (FR); Yannick Benedetti, Rosny Sous Bois (FR); Frederico Nardi, Paris (FR); Alain Commerçon, Vitry-sur-Seine (FR)

(73) Assignee: Sanofi-Aventis, Paris (FR)

( * ) Notice: Subject to any disclaimer, the term of this patent is extended or adjusted under 35 U.S.C. 154(b) by 304 days.

(21) Appl. No.: 12/267,691

(22) Filed: Nov. 10, 2008

(65) Prior Publication Data
US 2009/0093459 A1    Apr. 9, 2009

Related U.S. Application Data

(63) Continuation of application No. PCT/FR2007/000867, filed on May 23, 2007.

(30) Foreign Application Priority Data

May 24, 2006 (FR) .................................... 06 04735

(51) Int. Cl.
*C07D 223/12* (2006.01)
*A61K 31/55* (2006.01)
(52) U.S. Cl. .................................... 514/211.06; 540/488
(58) Field of Classification Search .................. 540/488; 514/211.06; 549/305, 306
See application file for complete search history.

(56) References Cited

U.S. PATENT DOCUMENTS

| | | | |
|---|---|---|---|
| 4,692,522 | A | 9/1987 | Parsons et al. |
| 4,831,135 | A | 5/1989 | Crews et al. |
| 5,283,241 | A | 2/1994 | Bochis et al. |
| 6,239,127 | B1 | 5/2001 | Kinder, Jr. et al. |
| 7,153,846 | B2 | 12/2006 | Hoffmann et al. |
| 2002/0128474 | A1 | 9/2002 | Xu et al. |
| 2007/0065929 | A1 | 3/2007 | Hoffmann et al. |
| 2007/0065932 | A1 | 3/2007 | Hoffmann et al. |
| 2007/0244087 | A1 | 10/2007 | Zhang et al. |
| 2007/0249584 | A1 | 10/2007 | Zhang et al. |

FOREIGN PATENT DOCUMENTS

| | | |
|---|---|---|
| EP | 0 687 673 A1 | 12/1995 |
| JP | 2004262793 | 9/2004 |
| WO | WO 98/35941 | 8/1998 |
| WO | WO 00/29382 | 5/2000 |
| WO | WO 01/85697 A1 | 11/2001 |
| WO | WO 02/39990 A2 | 5/2002 |
| WO | WO 2005/014574 A1 | 2/2005 |
| WO | WO 2005/044803 | 5/2005 |
| WO | WO 2006/056696 A2 | 6/2006 |

OTHER PUBLICATIONS

U.S. Appl. No. 12/267,689, filed Nov. 10, 2008, Zhang et al.
U.S. Appl. No. 12/267,692, filed Nov. 10, 2008, Zhang et al.
Adamczeski et al, Novel Sponge-Derived Amino Acids. 5. Structures, Stereochemistry, and Synthesis of Several New Heterocycles, J. Am. Chem. Soc. 1989, 111, pp. 647-654.
Chang et al, Synthesis of optically active alpha-aminobenzolactam via an oxidative-cyclization reaction, Tetrahedron: Asymmetry 14 (2003) pp. 2081-2085.
Groweiss, et al., Cytotoxic Metabolites from an Australian Collection of the Sponge, J. Nat. Prod.; 1999; 62; pp. 1691-1693.
Kinder et al, Synthesis and Antitumor Activity of Ester-Modified Analogues of Bengamide B, J. Med. Chem. 2001, 44, pp. 3692-3699.
Morton et al, Novel Solid-Phase Sythesis of 1,5-benzothiazepine-4-one Derivatives, Tetrahedron Letters 41 (2000) pp. 3029-3033.
Parsons et al, Cholecystokinin Antagonists. Synthesis and Biological Evaluation of a 3-Substituted Benzolactams, J. Med. Chem. 1989, 32, pp. 1681-1685.
Quinoa et al, Bengamides, Heterocyclic Anthelminthics from a Jaspidae Marine Sponge, J. Org. Chem. (1986) 51, pp. 4494-4497.
Ramana et al, A Carbohydrate-Based Approach for the Total Synthesis of 1,3-Polyol/alpha-Pyrone Antifungal Natural Products, J. Org. Chem. 2005, 70, pp. 8216-8219.
Slade et al, Angiotensin Converting Enzyme Inhibitors: 1,5-Benzothiazepine Derivatives, J. Med. Chem., 1985, 28, pp. 1517-1521.
Thale et al, Bengamides Revisited: New Structures and Antitumor Studies, J. Org. Chem. 2001, 66, pp. 1733-1741.

*Primary Examiner* — Bruck Kifle
(74) *Attorney, Agent, or Firm* — Scully, Scott, Murphy & Presser, P.C.

(57) ABSTRACT

The present invention relates to 2-alkoxy-3,4,5-trihydroxy-alkylamide benzothiazepine compounds, to pharmaceutical compositions comprising such compounds, to methods of treatment comprising administering such compounds, to processes for the preparation of such compounds and to intermediate precursors to such compounds.

33 Claims, No Drawings

2-ALKOXY-3,4,5-TRIHYDROXYALKYLA-MIDE-BENZOTHIAZEPINES PREPARATION THEREOF, COMPOSITIONS CONTAINING THEM AND USE THEREOF

The present invention relates especially to 2-alkoxy-3,4,5-trihydroxyalkylamide-benzothiazepines, to their preparation, to compositions containing them and to their use as medicaments.

More particularly, and according to a first aspect, the invention relates to 2-alkoxy-3,4,5-trihydroxyalkylamide-benzothiazepines that are useful as anticancer agents.

2-Methoxy-3,4,5-trihydroxyalkylamides have been described in U.S. Pat. No. 6,239,127, US 2001/0 044 433 A1, WO 01/85697, WO 00/29382, U.S. Pat. No. 4,831,135, EP 687 673 and US 2002/0128 474 A1. These documents essentially disclose analogues and derivatives of bengamide, a natural product isolated from a marine sponge, Jaspis coriacea.

These same products have been described in the literature: J. Org. Chem. (1986), 51(23), 4494-7; J. Org. Chem. (2001), 66(5), 1733-41; J. Med. Chem. 2001, 44, 3692-9.

The problem that the present invention proposes to solve is that of obtaining novel products with anticancer activity. In addition to maintaining anticancer activity, some of these novel products may also have advantageous properties in relation with their pharmacological activity, such as their pharmacokinetics, bioavailability, solubility, stability, toxicity, absorption or metabolism.

One subject of the present invention is products corresponding to the general formula (I) below:

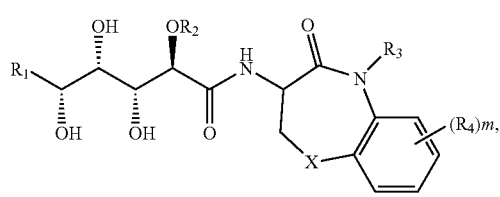

in which:
a) $R_1$ is independently selected from the group consisting of (C1-C12)alkyl, (C2-C12)alkenyl, (C2-C12)alkynyl, cycloalkyl, heterocyclyl, aryl, heteroaryl, cyclo(C1-C12)alkylalkyl, cyclo(C2-C12)alkylalkenyl, cyclo(C2-C12)alkylalkynyl, heterocyclyl(C1-C12)alkyl, heterocyclyl(C2-C12)alkenyl, heterocyclyl(C2-C12)alkynyl, aryl(C1-C12)alkyl, aryl(C2-C12)alkenyl, aryl(C2-C12)alkynyl, heteroaryl(C1-C12)alkyl, heteroaryl(C2-C12)alkenyl and heteroaryl(C2-C12)alkynyl, the aryl group of each $R_1$ being optionally substituted with one or more halogens;
b) $R_2$ is selected from the group consisting of (C1-C6)alkyl, aryl(C1-C6)alkyl, heteroaryl(C1-C6)alkyl, aryl, heteroaryl, (C1-C6)alkylthio(C1-C6)alkyl, di(C1-C6)alkylamino(C1-C6)alkyl, aryloxy(C1-C6)alkyl and (C1-C6)alkoxy(C1-C6)alkyl;
c) $R_3$ is selected from the group consisting of H, $COO(R_5)$, $CONH(R_5)$, $CO(R_5)$, $O(R_5)$ and $R_5$;
d) $R_4$ is independently selected from the group consisting of H, F, Cl, Br, $N(R_5)_2$, $NO_2$, CN, $COO(R_5)$, $CON(R_5)_2$, $NHCO(R_5)$, $NHCOO(R_5)$, $OCONH(R_5)$, $O(R_5)$ and $R_5$, or alternatively two substituents $R_4$, linked to two adjacent carbons of the phenyl, together form a ring chosen from cycloalkyl, heterocyclyl, aryl and heteroaryl, optionally substituted with one or more $R_4$;
e) m has the value 0, 1, 2, 3 or 4;
f) X is chosen from S, SO and $SO_2$;
g) $R_5$ is the independently chosen from a non-bonding lone pair of electrons, H, (C1-C12)alkyl, (C2-C12)alkenyl, (C2-C12)alkynyl, halo(C1-C12)alkyl, aryl(C1-C12)alkyl, heteroaryl(C1-C12)alkyl, heteroarylaryl(C1-C12)alkyl, aryl, heteroaryl and cycloalkyl, in which each $R_5$ is optionally substituted with at least one substituent chosen from OH, halogen, (C1-C4)alkyl, (C1-C4)alkoxy, aryl(C1-C4)alkyl, aryl, heteroaryl(C1-C4)alkyl, heteroaryl, —N(CH$_3$)$_2$, —NH$_2$, CONH$_2$,

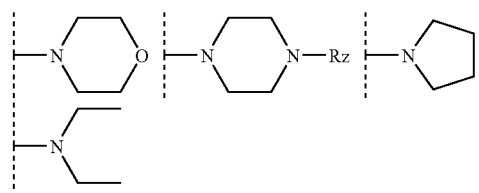

each of the Rz is independently selected from the group consisting of H, $COO(R_5)$, $CONH(R_5)$, $CON(R_5)_2$, $CO(R_5)$ and $R_5$, in which each $R_5$ is independently chosen from (C1-C4)alkyl, halo(C1-C4)alkyl, aryl(C1-C4)alkyl and heteroaryl(C1-C4)alkyl, in which each $R_5$ is optionally substituted with a substituent chosen from OH, halogen, (C1-C4)alkyl, (C1-C4)alkoxy, aryl(C1-C4)alkyl, aryl, heteroaryl(C1-C4)alkyl and heteroaryl; on condition that when $R_1$ is (E)—CH═CH—C(CH$_3$)$_3$, $R_2$ is methyl, X is S and m is 0, then $R_3$ is not a hydrogen atom, a (3,5-difluorophenyl)methyl group or a —CH$_2$—CH═CH$_2$ group.

One subject of the present invention is the products of general formula (I) above in which $R_1$ is independently selected from the group consisting of (C1-C12)alkyl, (C2-C12)alkenyl, (C2-C12)alkynyl, cycloalkyl, heterocyclyl, aryl, heteroaryl, aryl(C1-C12)alkyl, aryl(C2-C12)alkenyl, aryl(C2-C12)alkynyl, heteroaryl(C1-C12)alkyl, heteroaryl(C2-C12)alkenyl and heteroaryl(C2-C12)alkynyl.

A subject of the present invention is the products of general formula (I) above in which $R_2$ is selected from the group consisting of (C1-C6)alkyl, aryl(C1-C6)alkyl, heteroaryl(C1-C6)alkyl, aryl, heteroaryl, (C2-C12)alkenylaryl, (C2-C12)alkenylheteroaryl, (C1-C6)alkylthio(C1-C6)alkyl, di(C1-C6)alkylamino(C1-C6)alkyl and aryloxy(C1-C6)alkyl.

According to the invention, $R_1$ is preferentially chosen from —C(R$_6$)═C(R$_7$)(R$_8$) in which $R_6$, $R_7$ and $R_8$ are independently selected from H, (C1-C6)alkyl, cycloalkyl, heterocyclyl, aryl and heteroaryl.

More preferentially, $R_1$ is chosen from (E) —CH═CH—CH(CH$_3$)(C$_2$H$_5$), (E) —CH═CH—CH(CH$_3$)$_2$ and (E) —CH═CH—C(CH$_3$)$_3$, or alternatively from (E) —C(CH$_3$)═CH—CH(CH$_3$)(C$_2$H$_5$), (E) —C(CH$_3$)═CH—CH(CH$_3$)$_2$ and (E) —C(CH$_3$)═CH—C(CH$_3$)$_3$.

More preferentially, $R_1$ is chosen from (E) —CH═CH—C$_5$H$_9$, (E) —CH═CH—C$_6$H$_{11}$, (E) —CH═CH—(CH$_2$)$_3$—CH$_3$ and (E) —CH═CH—C$_6$H$_5$ in which the phenyl is optionally substituted with a fluorine atom.

According to the invention, $R_2$ is preferentially methyl.

Among the subjects of the present invention, a first group is characterized in that X is S. A second group is characterized in that X is SO and a third group is characterized in that X is $SO_2$.

Among the subjects of the present invention, a fourth group is characterized in that $R_3$ is independently chosen from: methyl, a phenylmethyl group and a (3,5-difluorophenyl)methyl group. A fifth group is characterized in that $R_3$ is H.

Among the subjects of the present invention, a sixth group is characterized in that $R_4$ is independently chosen from: F, Cl, Br, phenyl, cyanophenyl, trifluoromethyl, methoxy and phenoxy, or alternatively two substituents $R_4$, linked to two adjacent carbons of the phenyl, together form a pyrazine ring. A seventh group is characterized in that m is 0.

Preferably, the invention relates to the products illustrated in Table 1.

According to another aspect, the invention relates to processes for preparing the products of general formula (I) or (I'). The products of general formula (I') are precursors, which may be active, of the products of general formula (I). The products of general formula (I) are obtained from the products of general formula (I') via described processes or via one or more reactions that are standard for those skilled in the art, for instance a cyclopropanation, an oxidation or a chiral separation. The products of Examples 1 and 2 are especially obtained via oxidation of product 6 of general formula (I').

The products of general formula (I) or (I') may be obtained via hydrolysis of the products of general formula (II):

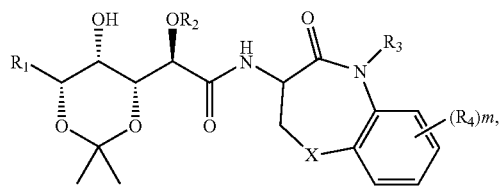

(II)

in which $R_1$, $R_2$, $R_3$, $R_4$, X and m are as defined above.

The products of general formula (II) may be obtained by reacting a product of general formula (III):

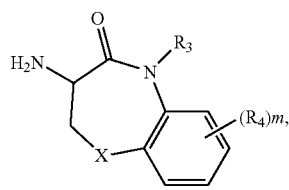

(III)

in which $R_3$, $R_4$, X and m are as defined above, with a product of general formula (IV):

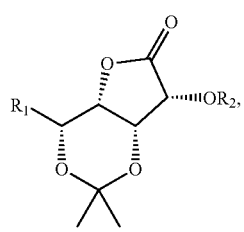

(IV)

in which $R_1$ and $R_2$ are as defined above.

The products of general formula (I) or (I') may also be obtained by reacting a product of general formula (III) as defined above with a product of general formula (V):

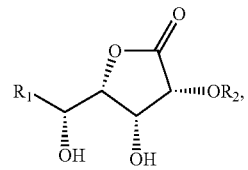

(V)

in which $R_1$ and $R_2$ are as defined above.

The products of general formula (V) may be obtained via hydrolysis of a product of general formula (IV):

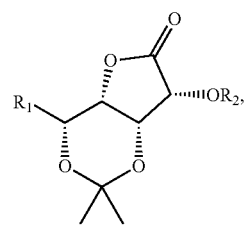

(IV)

in which $R_1$ and $R_2$ are as defined above. Products of general formula (V) for which $R_1$ represents —CH=CH—$R'_1$ may also be obtained via hydrolysis of a product of general formula (VII):

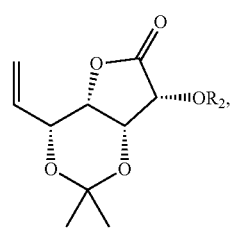

(VII)

in which $R_2$ is as defined above, in order to obtain a product of general formula (VI):

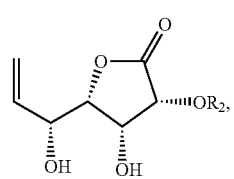

(VI)

in which $R_2$ is as defined above, which undergoes a metathesis in order to obtain a product of general formula (V):

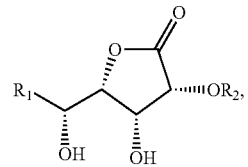

(V)

for which R₁ represents —CH=CH—R'₁ and R'₁ represents a (C1-C6)alkyl, cycloalkyl, heterocyclyl, aryl or heteroaryl group.

The products of general formula (VII) may be obtained via double dehydration of a product of general formula (VIII):

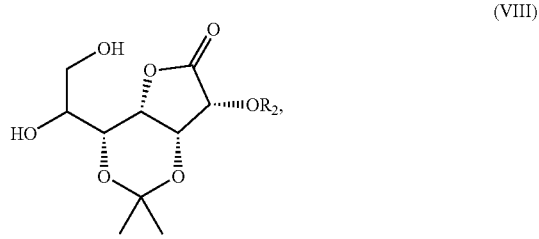

(VIII)

in which R₂ is as defined above.

The products of general formulae (I') and (II) as defined above, with the exception of those for which R₁ is (E) —CH=CH—C(CH₃)₃, R₂ is methyl, X is S, m is 0 and R₃ is a hydrogen atom, a (3,5-difluorophenyl)methyl group or a —CH₂—CH=CH₂ group, are a subject of the present invention.

The products of general formula (III) for which X is S, R₃ is H, methyl, phenylmethyl or (3,5-difluorophenyl)methyl and R₄ is F, Cl, Br, phenyl, cyanophenyl, trifluoromethyl, methoxy or phenoxy, or alternatively m has the value 0, with the exception of those for which X is S, m is 0 and R₃ is a hydrogen atom or a (3,5-difluorophenyl)methyl group and with the exception of those for which X is S, R₃ is phenylmethyl and R₄ is trifluoromethyl or methoxy, are a subject of the present invention.

The products of general formulae (IV) and (V) for which R₂ is methyl and R₁ is -(E) —CH=CH—C₅H₉ or -(E) —CH=CH—C₆H₅ in which the phenyl is substituted with a fluorine atom, are a subject of the present invention.

The products of general formula (VI) for which R₂ is methyl are a subject of the present invention. The products of general formula (VII) for which R₂ is methyl are a subject of the present invention.

The products according to the present invention may exist in the form of bases, acid-addition salts, solvates, hydrates or prodrugs.

The products according to the invention may be in non-chiral form or racemic form, or in a form enriched in one stereoisomer, or enriched in one enantiomer; and may optionally be salified. The products for which the carbon linked to the exocyclic amine is of (R) configuration are preferred.

The products in accordance with the invention may be used for the manufacture of a medicament that is useful for preventing or treating a pathological condition, in particular a cancer.

The products of the present invention may also be used for the manufacture of a medicament that is useful for preventing or treating a pathological condition in which neovascularization or angiogenesis takes place inappropriately, i.e. in cancers in general and in particular cancers such as Kaposi's sarcoma or infantile haemoangioma, but also in rheumatoid arthritis, osteoarthritis and/or the associated pain, inflammatory bowel diseases such as haemorrhagic rectocolitis or Crohn's disease, and eye pathologies such as age-related macular degeneration, diabetic retinopathy, chronic inflammation and psoriasis.

Angiogenesis is a process of generation of new blood vessels from pre-existing vessels. Tumoral angiogenesis (forma-tion of new blood vessels), which is essential for tumour growth, is also one of the essential factors of metastasic dissemination (Oncogene, 2003 May 19; 22(20): 3172-9; Nat. Med. 1995, January; 1(1): 27-31).

The present invention also relates to therapeutic compositions containing a compound according to the invention, in combination with an excipient that is pharmaceutically acceptable according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected against the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and solvents or of complexing agents and solvents.

The liquid forms will preferably be injectable, and, as a result, will have a formulation that is acceptable for such a use.

Acceptable routes of administration by injection include the intravenous, intraperitoneal, intramuscular and subcutaneous routes, the intravenous route being preferred.

The administered dose of the compounds of the invention will be adapted by the practitioner depending on the route of administration to the patient and said patient's condition.

The compounds of the present invention may be administered alone or as a mixture with other anticancer agents. Among the possible combinations that may be mentioned are:
  alkylating agents and especially cyclophosphamide, melphalan, ifosfamide, chlorambucil, busulfan, thiotepa, prednimustine, carmustin, lomustin, semustin, streptozotocin, decarbazin, temozolomide, procarbazin and hexamethylmelamine
  platinum derivatives especially such as cisplatin, carboplatin or oxaliplatin
  antibiotics especially such as bleomycin, mitomycin and dactinomycin
  antimicrotubule agents especially such as vinblastine, vincristine, vindesine, vinorelbine and taxoids (paclitaxel and docetaxel)
  anthracyclines especially such as doxorubicin, daunorubicin, idarubicin, epirubicin, mitoxantrone and losoxantrone
  topoisomerases of groups I and II, such as etoposide, teniposide, amsacrine, irinotecan, topotecan and tomudex
  fluoropyrimidines such as 5-fluorouracil, UFT and floxuridine
  cytidine analogues such as 5-azacytidine, cytarabine, gemcitabine, 6-mercaptopurine and 6-thioguanine
  adenosine analogues such as pentostatin, cytarabine or fludarabine phosphate
  methotrexate and folinic acid
  enzymes and various compounds such as L-asparaginase, hydroxyurea, trans-retinoic acid, suramine, dexrazoxane, amifostine and herceptin, and also oestrogenic and androgenic hormones
  antivascular agents such as combretastatin or colchicine derivatives and prodrugs thereof.
  antivascular agents such as combretastatin, for example CA4P, chalcones or colchicine, for example ZD6126, and prodrugs thereof
  kinase inhibitors such as ertonilib or imatinib biotherapeutic agents, for instance antibodies such as rituximab, bevacizumab, cetuximab, trastuzumab or alemtuzumab proteasome inhibitors such as bortezomib.

It is also possible to combine the compounds of the present invention with a radiation treatment. These treatments may be administered simultaneously, separately or sequentially. The treatment will be adapted by the practitioner according to the patient to be treated.

DEFINITIONS

The term "halogen" refers to an element chosen from F, Cl, Br and I.

The term "alkyl" refers to a saturated, linear or branched hydrocarbon-based substituent containing from 1 to 12 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl are examples of alkyl substituents.

The term "alkenyl" refers to a linear or branched hydrocarbon-based substituent containing one or more unsaturations, and containing from 2 to 12 carbon atoms. The substituents ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methylidenylprop-2-enyl, Z-2-methylbut-1,3-dienyl, E-2-methylbut-1,3-dienyl, 2-methyl-1-methylidenylprop-2-enyl, undec-1-enyl and undec-10-enyl are examples of alkenyl substituents.

The term "alkynyl" refers to a linear or branched hydrocarbon-based substituent containing at least two unsaturations borne by a pair of vicinal carbon atoms, and containing from 2 to 12 carbon atoms. The substituents ethynyl; prop-1-ynyl; prop-2-ynyl; and but-1-ynyl are examples of alkynyl substituents.

The term "aryl" refers to a monocyclic or polycyclic aromatic substituent containing from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of aryl substituents.

The term "heteroaryl" refers to a monocyclic or polycyclic heteroaromatic substituent containing from 1 to 13 carbon atoms and from 1 to 4 heteroatoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl are examples of heteroaryl substituents.

The term "heteroatom" refers herein to an at least divalent atom, other than carbon. N; O; S; and Se are examples of heteroatoms.

The term "cycloalkyl" refers to a saturated or partially unsaturated cyclic hydrocarbon-based substituent containing from 3 to 12 carbon atoms. The substituents cyclopropyl; cyclobutyl; cyclopentyl; cyclopentenyl; cyclopentadienyl; cyclohexyl; cyclohexenyl; cycloheptyl; bicyclo[2.2.1]heptyl; cyclooctyl; bicyclo[2.2.2]octyl; adamantyl; and perhydronaphthyl are examples of cycloalkyl substituents.

The term "heterocyclyl" refers to a saturated or partially unsaturated cyclic hydrocarbon-based substituent containing from 1 to 13 carbon atoms and from 1 to 4 heteroatoms. Preferably, the saturated or partially unsaturated cyclic hydrocarbon-based substituent will be monocyclic and will contain 4 or 5 carbon atoms and 1 to 3 heteroatoms.

As regards fused phenyl, when m has the value zero, this means that it is an unsubstituted phenyl (or a phenyl substituted with 4 hydrogen atoms), and when m has the value 1, 2, 3 or 4, this means that 1, 2, 3 or 4 hydrogen atoms are substituted with a substituent $R_4$.

The advantages of the invention will be illustrated more particularly by the following examples:

Abbreviations:

Ac acetate; Bn benzyl; ° C. degrees Celsius; cat. catalyst; TLC thin-layer chromatography; PCC preparative column chromatography; cm centimeter; δ chemical shift; d doublet; dd doublet of doublets; DMF dimethylformamide; DMSO-$d_6$ deuterated dimethyl sulfoxide; dt doublet of triplets; eq. equivalent; ES+/− electrospray (positive/negative modes); Et ethyl; g gram; h hour; Hz hertz; $IC_{50}$ inhibition constant at 50% of activity; iPr isopropyl; d. day; J coupling constant; LCMS liquid chromatography coupled to mass spectrometry; m multiplet; Me methyl; mg milligram; MHz megahertz; mL milliliter; μl microliter; mm millimeter; μm micrometer; mmol millimole; min minute; N mol·$L^{-1}$; m.p. melting point; Ph phenyl; ppm parts per million; q quartet; Yld yield; Rf frontal ratio; $^1H$ NMR proton nuclear magnetic resonance; s singlet; bs broad singlet; t triplet; r.t. room temperature; tBu tert-butyl; TFA trifluoroacetic acid; THF tetrahydrofuran; $t_R$ retention time; UV ultraviolet; V volt.

EXAMPLE 1

N-[(1R,3R)-5-(3,5-difluorobenzyl)-1,4-dioxo-2,3,4,5-tetrahydro-1,5-benzothiazepin-3-yl]-((6E)-(2R,3R,4S,5R)-3,4,5-trihydroxy-2-methoxy-8,8-dimethyl-non-6-enamide and

EXAMPLE 2

N-[(1S,3R)-5-(3,5-difluorobenzyl)-1,4-dioxo-2,3,4,5-tetrahydro-1,5-benzothiazepin-3-yl]-((6E)-(2R,3R,4S,5R)-3,4,5-trihydroxy-2-methoxy-8,8-dimethyl-non-6-enamide Step 1: Preparation of tert-butyl (3R)-[5-(3,5-difluorobenzyl)-4-oxo-2,3,4,5-tetrahydro-1,5-benzothiazepin-3-yl]carbamate (2)

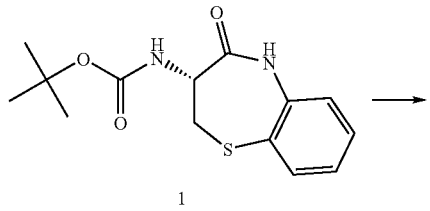

1

-continued

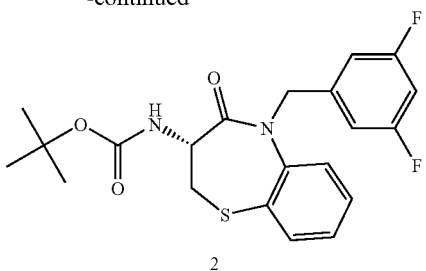

2

177 mg of sodium hydride as a 60% suspension in oil (4.42 mmol) are introduced at room temperature into a 100 mL round-bottomed flask, with stirring and under an argon atmosphere, containing 40 mL of THF and 1.3 g of 1 (4.4 mmol). The medium is stirred for 1 hour and 1.8 g (8.83 mmol) of 3,5-difluorobenzyl bromide are then added. The medium is stirred overnight. 100 mL of EtOAc are added and the organic phase is washed with twice 100 mL of water. The organic phase is dried over MgSO$_4$, filtered and then evaporated to dryness. 3 g of a yellow oil are obtained, which product gives, after chromatography on a silica cartridge (120 g) eluting with a heptane/EtOAc mixture (as a gradient: 12% to 100% EtOAc), 1.59 g of product 2.

$^1$H NMR (400 MHz, DMSO-d$_6$), δ (ppm): 1.35 (s, 9H); 3.11 (t, J=11.5 Hz, 1H); 3.48 (dd, J=7.0 and 11.5 Hz, 1H); 4.15 (m, 1H); 5.03 (d, J=16.0 Hz, 1H); 5.13 (d, J=16.0 Hz, 1H); from 6.98 to 7.10 (m, 3H); 7.28 (broad t, J=8.0 Hz, 1H); 7.39 (broad d, J=8.0 Hz, 1H); from 7.47 to 7.53 (m, 2H); 7.63 (broad d, J=7.5 Hz, 1H).

Step 2: Preparation of (3R)-3-amino-5-(3,5-difluorobenzyl)-2,3-dihydro-5H-1,5-benzothiazepin-4-one hydrochloride (3)

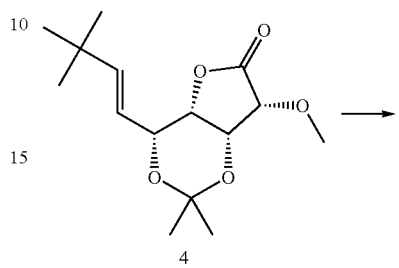

1.59 g of 2 (3.78 mmol) are placed in a 100 mL round-bottomed flask and 25 mL of a solution of hydrogen chloride in dioxane (4 M) are added. The medium is stirred for 5 hours at room temperature under argon. After evaporating off the solvent, 1.44 g of amine 3 are obtained in hydrochloride form, which product is used directly for the following step.

$^1$H NMR (400 MHz, DMSO-d$_6$), δ (ppm): 3.25 (t, J=11.5 Hz, 1H); 3.75 (dd, J=7.0 and 11.5 Hz, 1H); 3.94 (dd, J=7.0 and 11.5 Hz, 1H); 5.09 (d, J=16.0 Hz, 1H); 5.24 (d, J=16.0 Hz, 1H); from 6.97 to 7.15 (m, 3H); 7.33 (m, 1H); from 7.48 to 7.59 (m, 2H); 7.68 (dd, J=1.5 and 7.5 Hz, 1H); 8.63 (broad s, 3H).

Step 3: Preparation of (3R,4R,5S)-4-hydroxy-5-((2E)-(2R)-1-hydroxy-4,4-dimethylpent-2-enyl)-3-methoxydihydrofuran-2-one (5)

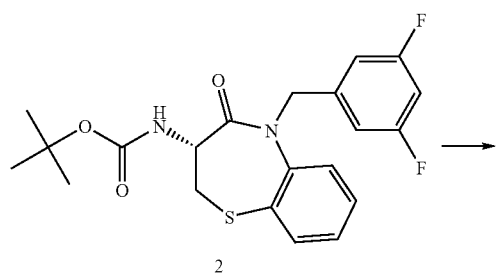

17 mL of TFA dissolved in 10 mL of water are added to a 250 mL round-bottomed flask containing 40 mL of water and 3.6 g of 4 (which may be prepared according to the procedures described in Org. Process Res. Dev. 2003, 7(6), 856-865) as a suspension. The medium is stirred for 1.5 hours at room temperature and is then diluted with 290 mL of water, frozen and freeze-dried. 4 g of an oil are obtained, which product crystallizes from 20 mL of isopropyl ether at room temperature. After filtering off by suction, washing with isopropyl ether and drying under vacuum at 40° C., 2.46 g of expected product 5 are obtained (white crystals).

m.p.: 123° C.

IC: m/z=262 MNH$_4$$^+$.

$^1$H NMR (400 MHz, DMSO-d$_6$) δ (ppm): 1.00 (s, 9H); 3.41 (s, 3H); 3.93 (dd, J=2.5 and 9.0 Hz, 1H); from 4.22 to 4.31 (m, 3H); 5.19 (d, J=5.0 Hz, 1H); 5.42 (dd, J=5.0 and 16.0 Hz, 1H); 5.43 (d, J=4.5 Hz, 1H); 5.87 (d, J=16.0 Hz, 1H).

IR (KBr): 3239; 2964; 2914; 1701; 1499; 1312; 1253; 1047 and 751 cm$^{-1}$.

Step 4: Preparation of N-[(3R)-5-(3,5-difluorobenzyl)-4-oxo-2,3,4,5-tetrahydro-1,5-benzothiazepin-3-yl]-(6E)-(2R,3R,4S,5R)-3,4,5-trihydroxy-2-methoxy-8,8-dimethylnon-6-enamide (6)

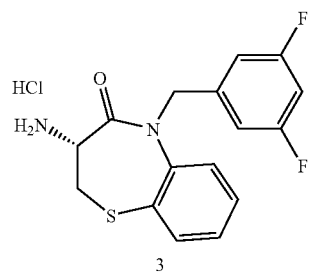

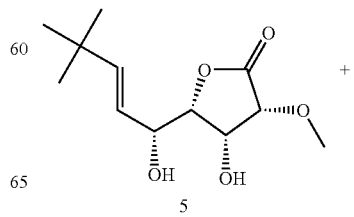

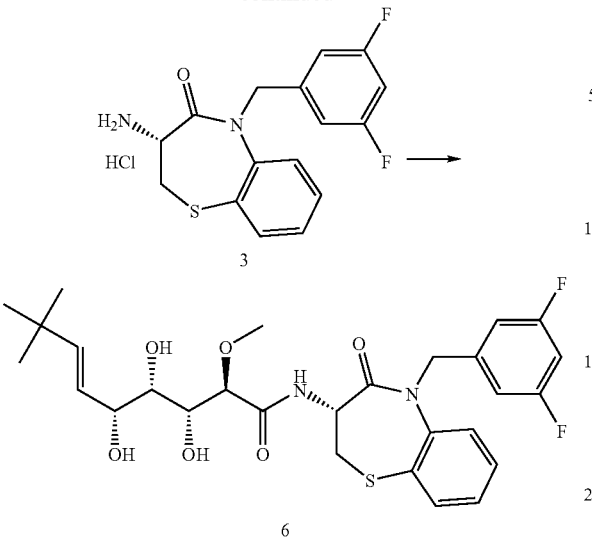

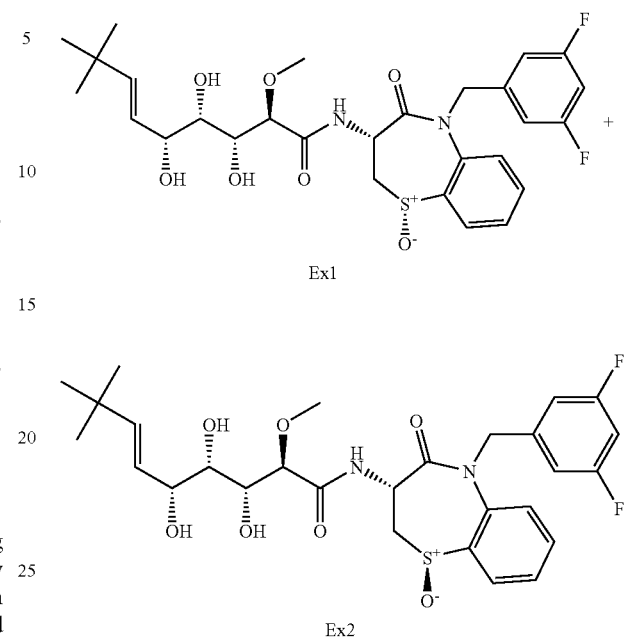

99 mg of 5 (405 μmol), 362 mg of 3 (1.0 mmol) and 135 mg of sodium 2-ethylhexanoate (0.81 mmol) are successively introduced into 2.0 mL of THF in a Wheaton tube, with stirring and under an argon atmosphere. The mixture is stirred at room temperature for 24 hours. 3 mL of ethyl acetate are added to the reaction medium. The medium is washed successively with 3 mL of HCl solution (1N) and then with 5 mL of saturated NaHCO$_3$ solution and 3 mL of water. The organic phase is dried over anhydrous magnesium sulfate, filtered and then evaporated to dryness. 300 mg of a brown solid are obtained, which product is chromatographed on a silica cartridge (10 g, heptane/EtOAc eluent—as a gradient: 25% to 100% EtOAc). 123 mg of expected product 6 are collected.

ES: 565(+)=(M+H)(+); 547(+)=(M+H)(+)−H$_2$O.

$^1$H NMR (400 MHz, DMSO-d$_6$), δ (ppm): 0.95 (s, 9H); 3.20 (s, 3H); 3.21 (t, J=12.0 Hz, 1H); from 3.32 to 3.47 (masked m, 1H); 3.48 (dd, J=7.0 and 12.0 Hz, 1H); 3.50 (partially masked m, 1H); 3.69 (d, J=8.0 Hz, 1H); 3.92 (m, 1H); 4.30 (broad m, 2H); 4.45 (m, 1H); 4.54 (d, J=4.5 Hz, 1H); 5.03 (d, J=16.0 Hz, 1H); 5.21 (d, J=16.0 Hz, 1H); 5.28 (dd, J=7.0 and 16.0 Hz, 1H); 5.61 (broad d, J=16.0 Hz, 1H); from 7.00 to 7.10 (m, 3H); 7.29 (m, 1H); from 7.45 to 7.55 (m, 2H); 7.61 (dd, J=1.5 and 7.5 Hz, 1H); 8.49 (d, J=8.0 Hz, 1H).

Step 4: Preparation of N-[(1R,3R)-5-(3,5-difluorobenzyl)-1,4-dioxo-2,3,4,5-tetrahydro-1,5-benzothiazepin-3-yl]-((6E)-(2R,3R,4S,5R)-3,4,5-trihydroxy-2-methoxy-8,8-dimethyl-non-6-enamide (Example 1) and N-[(1S,3R)-5-(3,5-difluorobenzyl)-1,4-dioxo-2,3,4,5-tetrahydro-1,5-benzothiazepin-3-yl]-((6E)-(2R,3R,4S,5R)-3,4,5-trihydroxy-2-methoxy-8,8-dimethylnon-6-enamide (Example 2)

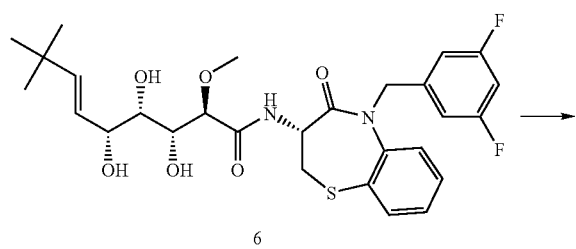

100 mg of 6 (177 μmol), 1 mL of hexafluoro-2-propanol and 35 μL of 33% aqueous hydrogen peroxide solution are placed in a Wheaton tube, with stirring and under an argon atmosphere. The mixture is stirred at room temperature for 5 hours. A further 70 μL of aqueous hydrogen peroxide solution are added and the medium is stirred for 24 hours. 3 mL of Na$_2$SO$_3$ solution are added to the reaction medium. The resulting medium is extracted twice with 3 mL of CH$_2$Cl$_2$. The organic phase is dried over anhydrous magnesium sulfate, filtered and then evaporated to dryness. 65 mg of crude product are obtained, which product is chromatographed on a preparative silica plate (eluent: 90/10 CH$_2$Cl$_2$/MeOH). 11.5 mg of expected product Example 1 and 28.5 mg of expected product Example 2 are collected.

ES: m/z=579 (M−H)$^−$.

Example 1: $^1$H NMR (400 MHz, DMSO-d$_6$), δ (ppm): 0.95 (s, 9H); 3.22 (s, 3H); from 3.26 to 3.32 (masked m, 1H); 3.38 (dd, J=11.0 and 14.5 Hz, 1H); 3.52 (m, 1H); 3.71 (d, J=8.0 Hz, 1H); 3.84 (dd, J=7.5 and 14.5 Hz, 1H); 3.93 (m, 1H); 4.25 (d, J=7.0 Hz, 1H); 4.32 (d, J=5.5 Hz, 1H); 4.55 (d, J=4.5 Hz, 1H); 4.67 (m, 1H); 4.75 (d, J=16.5 Hz, 1H); 5.24 (d, J=16.5 Hz, 1H); 5.29 (dd, J=7.0 and 16.0 Hz, 1H); 5.61 (d, J=16.0 Hz, 1H); 7.07 (tt, J=2.0 and 9.5 Hz, 1H); 7.15 (m, 2H); 7.34 (d, J=7.5 Hz, 1H); 7.42 (t, J=7.5 Hz, 1H); from 7.63 to 7.68 (m, 2H); 8.59 (d, J=7.5 Hz, 1H).

Example 2: $^1$H NMR (400 MHz, DMSO-d$_6$), δ (ppm): 0.95 (s, 9H); from 3.15 to 3.32 (masked m, 2H); 3.22 (s, 3H); 3.49 (m, 1H); 3.69 (d, J=8.0 Hz, 1H); 3.92 (m, 1H); 4.17 (t, J=11.5 Hz, 1H); 4.30 (m, 2H); 4.44 (m, 1H); 4.55 (d, J=4.5 Hz, 1H); 4.94 (d, J=15.5 Hz, 1H); 5.19 (d, J=15.5 Hz, 1H); 5.28 (dd, J=7.0 and 16.0 Hz, 1H); 5.61 (d, J=16.0 Hz, 1H); 6.96 (m, 2H); 7.13 (tt, J=2.0 and 9.5 Hz, 1H); 7.53 (m, 1H); from 7.62 to 7.73 (m, 3H); 8.54 (d, J=7.5 Hz, 1H).

EXAMPLE 3

N-[(3R)-5-benzyl-4-oxo-2,3,4,5-tetrahydro-1,5-benzothiazepin-3-yl]-(6E)-(2R,3R,4S,5R)-3,4,5-trihydroxy-2-methoxy-8,8-dimethyl non-6-enamide

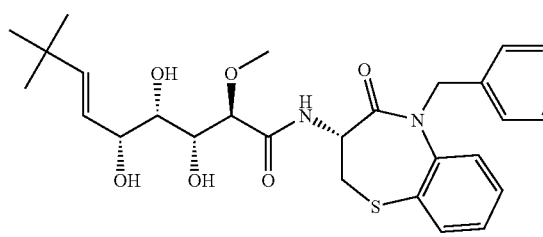

Ex3

Step 1: Preparation of tert-butyl (3R)-[5-benzyl-4-oxo-2,3,4,5-tetrahydro-1,5-benzothiazepin-3-yl]carbamate (7)

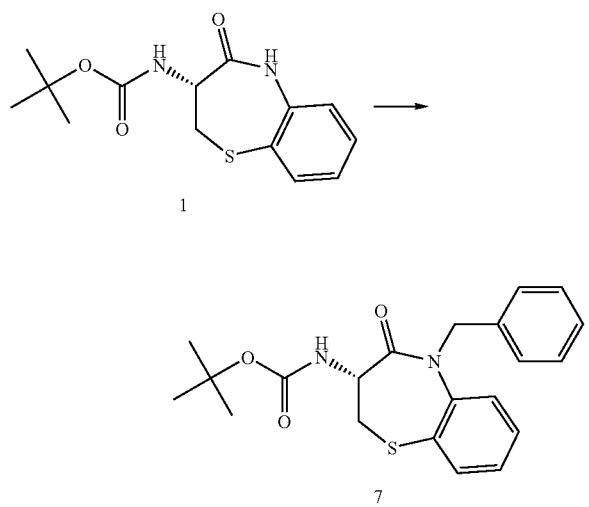

42 mg of sodium hydride as a 60% suspension in oil (1.07 mmol) are introduced at room temperature into a 50 mL round-bottomed flask, with stirring and under an argon atmosphere, containing 20 mL of THF and 315 mg of 1 (1.07 mmol). The medium is stirred for 1 hour and 183 mg (1.07 mmol) of benzyl bromide are then added. The medium is left stirring overnight, 30 mL of EtOAc are added and the organic phase is washed with 50 mL of water. The organic phase is dried over MgSO$_4$, filtered and then evaporated to dryness. 0.4 g of a translucent oil is obtained, which product gives, after chromatography on a silica cartridge (10 g) eluting with a mixture of CH$_2$Cl$_2$/MeOH (as a gradient: 1% to 10% MeOH), 0.28 g of product 7.

$^1$H NMR (300 MHz, DMSO-d$_6$), δ (ppm): 1.35 (s, 9H); 3.09 (t, J=11.5 Hz, 1H); 3.45 (dd, J=7.0 and 11.5 Hz, 1H) 4.15 (m, 1H); 4.97 (d, J=15.5 Hz, 1H); 5.20 (d, J=15.5 Hz, 1H); from 7.13 to 7.30 (m, 6H); 7.39 (d, J=8.0 Hz, 1H); 7.47 (m, 2H); 7.58 (d, J=7.5 Hz, 1H).

Step 2: Preparation of (3R)-amino-5-benzyl-2,3-dihydro-5H-1,5-benzothiazepin-4-one hydrochloride (8)

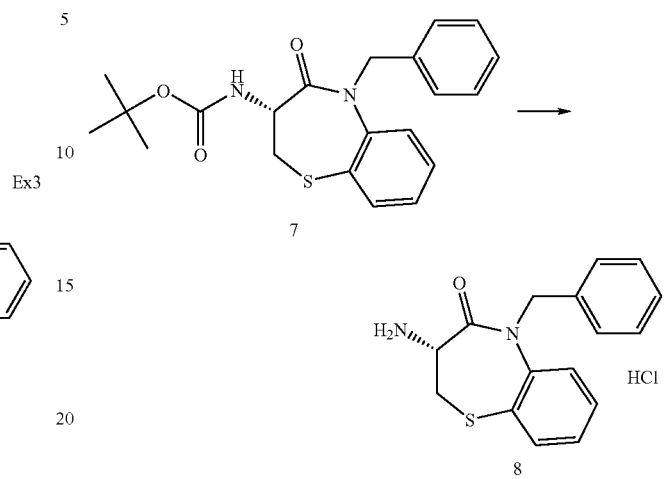

0.28 g of 7 (0.73 mmol) is taken up in a 50 mL round-bottomed flask and 6 mL of a solution of hydrogen chloride in dioxane (4 M) are added. The medium is stirred for 5 hours at room temperature under argon. After evaporating off the solvent and triturating with a mixture of CH$_2$Cl$_2$ and isopropyl ether, followed by drying, 0.24 g of amine 8 (yellow foam) is obtained in the form of the hydrochloride, which product is used directly in the following step.

$^1$H NMR (300 MHz, DMSO-d$_6$), δ (ppm): 3.22 (t, J=11.5 Hz, 1H); 3.73 (dd, J=7.0 and 11.5 Hz, 1H); 3.91 (dd, J=7.0 and 11.5 Hz, 1H); 4.97 (d, J=15.5 Hz, 1H); 5.33 (d, J=15.5 Hz, 1H); from 7.17 to 7.34 (m, 6H); from 7.48 to 7.59 (m, 2H); 7.62 (d, J=7.5 Hz, 1H); 8.60 (broad s, 3H).

IR (KBr): 2923; 2613; 1680; 1471; 1453; 1261; 1203; 774; 743; 698; 629 and 458 cm$^{-1}$ Step 3: Preparation of N-((3R)-5-benzyl-4-oxo-2,3,4,5-tetrahydro-1,5-benzothiazepin -3-yl)-(R)-2-[(4R,5S,6R)-6-((1E)-3,3-dimethylbut-1-enyl)-5-hydroxy-2,2-dimethyl-1,3-dioxinan-4-yl]-2-methoxyacetamide (9)

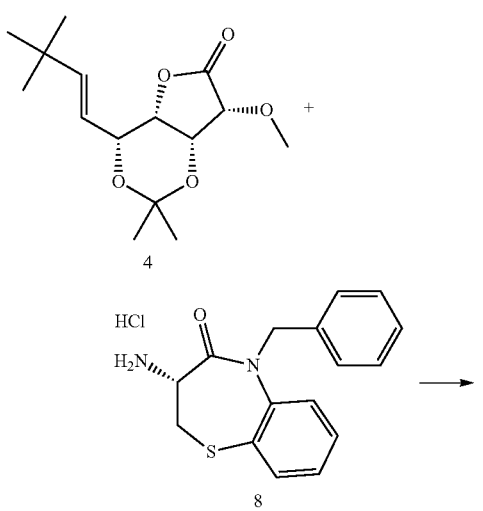

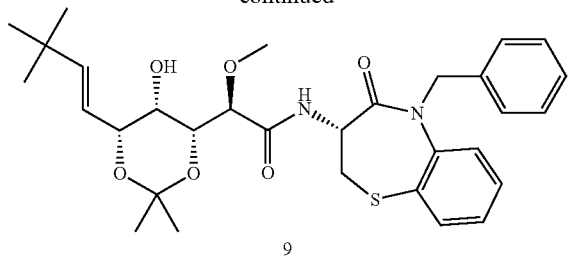

50 mg of 4 (176 μmol), 113 mg of 8 (0.35 mmol) and 73 mg of sodium 2-ethylhexanoate (0.44 mmol) in 1 mL of THF are successively introduced into a Wheaton tube, with stirring and under an argon atmosphere. Stirring is continued at room temperature for 24 hours. 3 mL of ethyl acetate are added to the reaction medium. The resulting mixture is washed successively with 3 mL of HCl solution (1N) and then with 3 mL of saturated NaHCO₃ solution and 3 mL of water. The organic phase is dried over anhydrous magnesium sulfate, filtered and then evaporated to dryness. The crude product is chromatographed on a silica cartridge (12 g, CH₂Cl₂/MeOH eluent—as a gradient: 1% to 10% MeOH) and 100 mg of expected product 9 are collected.

¹H NMR (400 MHz, DMSO-d₆), δ (ppm): 0.98 (s, 9H); 1.22 (s, 3H); 1.28 (s, 3H); 3.15 (t, J=11.5 Hz, 1H); from 3.22 to 3.34 (masked m, 1H); 3.23 (s, 3H); 3.47 (m, 1H); 3.80 (d, J=9.0 Hz, 1H); 3.90 (d, J=9.0 Hz, 1H); 4.25 (d, J=7.0 Hz, 1H); 4.36 (d, J=8.0 Hz, 1H); 4.47 (m, 1H); 4.96 (d, J=15.5 Hz, 1H); 5.24 (d, J=15.5 Hz, 1H); 5.44 (dd, J=7.0 and 16.0 Hz, 1H); 5.67 (d, J=16.0 Hz, 1H); from 7.14 to 7.30 (m, 6H); 7.52 (m, 2H); 7.61 (d, J=8.0 Hz, 1H); 8.52 (d, J=8.5 Hz, 1H).

Step 4: Preparation of N-[(3R)-5-benzyl-4-oxo-2,3,4,5-tetrahydro-1,5-benzothiazepin-3-yl]-(6E)-(2R,3R,4S,5R)-3,4,5-trihydroxy-2-methoxy-8,8-dimethylnon-6-enamide (Example 3)

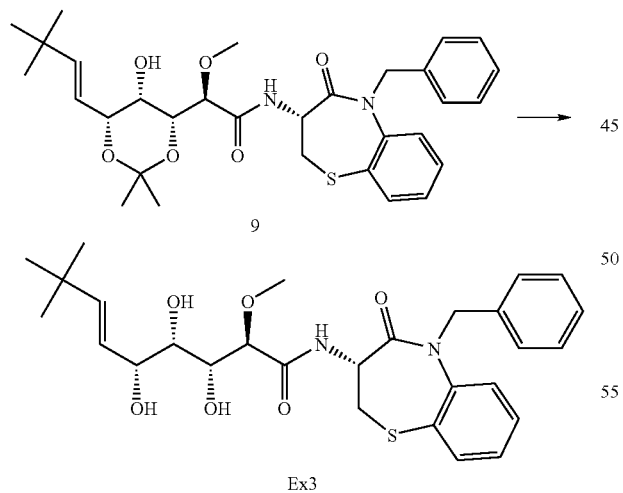

101 mg of 9 (178 μmol) in 0.85 mL of THF and 1.78 mL of 1N hydrochloric acid are mixed together, with stirring and under argon, in a 20 mL round-bottomed flask. Stirring is continued for 5 hours at room temperature. The solution is then cooled to 0° C. It is neutralized to pH 7.0 with 1N sodium hydroxide. The resulting mixture is extracted twice with 5 mL of EtOAc. The organic phases are combined, dried over magnesium sulfate and filtered and then brought to dryness. 66 mg of crude product are obtained, which product, after purification on a preparative silica plate (eluent: 90/10 CH₂Cl₂/MeOH), gives 16.5 mg of expected product Example 3.

IC: m/z=546 MNH₄⁺.; m/z=529 MH⁺.

¹H NMR (400 MHz, DMSO-d₆), δ (ppm): 0.95 (s, 9H); 3.17 (partially masked t, J=11.5 Hz, 1H); 3.21 (s, 3H); from 3.25 to 3.33 (masked m, 1H); from 3.40 to 3.53 (m, 2H); 3.69 (d, J=8.0 Hz, 1H); 3.93 (m, 1H); 4.32 (m, 2H); 4.47 (m, 1H); 4.54 (broad d, J=4.5 Hz, 1H); 4.94 (d, J=15.5 Hz, 1H); from 5.25 to 5.32 (m, 2H); 5.61 (d, J=16.0 Hz, 1H); from 7.14 to 7.30 (m, 6H); from 7.45 to 7.54 (m, 2H); 7.59 (d, J=7.5 Hz, 1H); 8.40 (d, J=8.5 Hz, 1H).

EXAMPLE 4

N-[(3R)-5-methyl-4-oxo-2,3,4,5-tetrahydro-1,5-benzothiazepin-3-yl]-(6E)-(2R,3R,4S,5R)-3,4,5-trihydroxy-2-methoxy-8,8-dimethylnon-6-enamide

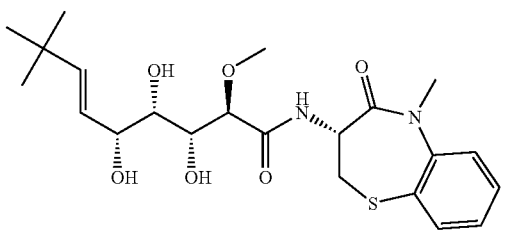

Step 1: Preparation of tert-butyl (3R)-[5-methyl-4-oxo-2,3,4,5-tetrahydro-1,5-benzothiazepin-3-yl]carbamate (10)

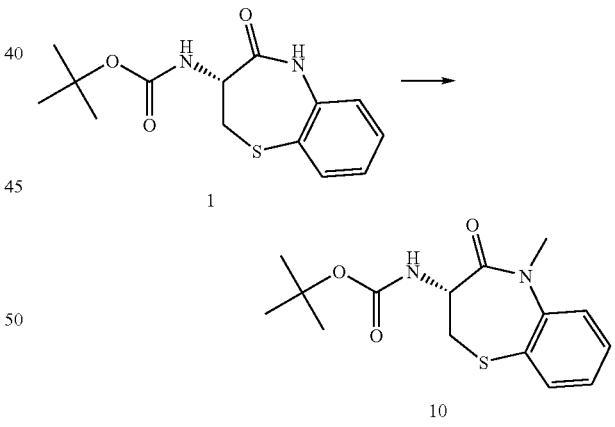

224 mg of sodium hydride as a 60% suspension in oil (5.6 mmol) are introduced at room temperature into a 100 mL round-bottomed flask, with stirring and under an argon atmosphere, containing 15 mL of THF and 1.5 g of 1 (5.1 mmol). The medium is stirred for 1 hour, followed by addition of 0.80 g (5.6 mmol) of methyl iodide. The medium is stirred for 1.5 hours, 50 mL of CH₂Cl₂ are added and the organic phase is washed with twice 30 mL of water and once 30 ml of saturated NaCl solution. The organic phase is dried over MgSO₄, filtered and then evaporated to dryness. The crude product is chromatographed on a silica cartridge (120 g) with a heptane/EtOAc mixture (75/25) to give 1.31 g of product 10.

m.p.: 118° C.±2° C.

ES: m/z=309 MH⁺.

¹H NMR (400 MHz, DMSO-d₆), δ (ppm): 1.32 (s, 9H); 3.01 (t, J=11.5 Hz, 1H); 3.29 (s, 3H); 3.41 (dd J=7.0 and 11.5 Hz, 1H); 4.07 (m, 1H) 7.25 (d, J=9.0 Hz, 1H); 7.30 (m, 2H); 7.57 (m, 2H); 7.63 (d, J=7.5 Hz, 1H).

Step 2: Preparation of (3R)-amino-5-methyl-2,3-dihydro-5H-1,5-benzothiazepin-4-one hydrochloride (11)

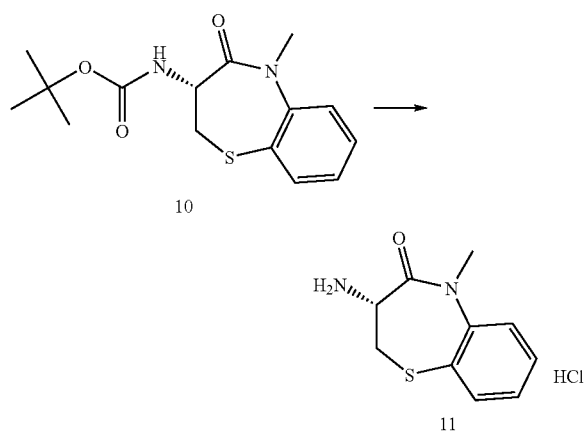

1.01 g of 10 (3.28 mmol) are taken up in a 100 mL round-bottomed flask and 20 mL of a solution of hydrogen chloride in dioxane (4 M) are added. The medium is stirred for 2 hours at room temperature under argon. After evaporating off the solvent, triturating with ether, and filtering off by suction, 0.83 g of amine 11 (pale yellow powder) is obtained in the form of the hydrochloride, which product is used directly in the following step.

IE: m/z=208 M⁺.

¹H NMR (400 MHz, DMSO-d₆), δ (ppm): 3.15 (t, J=11.5 Hz, 1H); 3.35 (s, 3H); 3.67 (dd, J=7.0 and 11.5 Hz, 1H); 3.85 (dd J=7.0 and 11.5 Hz, 1H); 7.36 (m, 1H); from 7.56 to 7.63 (m, 2H); 7.69 (m, 1H); 8.41 (broad s, 3H).

Step 3: Preparation of N-[(3R)-5-methyl-4-oxo-2,3,4,5-tetrahydro-1,5-benzothiazepin-3-yl]-(6E)-(2R,3R,4S,5R)-3,4,5-trihydroxy-2-methoxy-8,8-dimethylnon-6-enamide (Example 4)

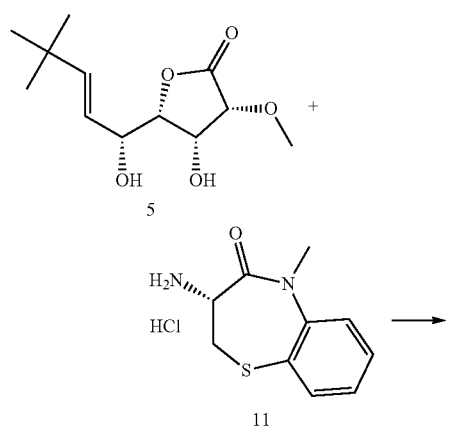

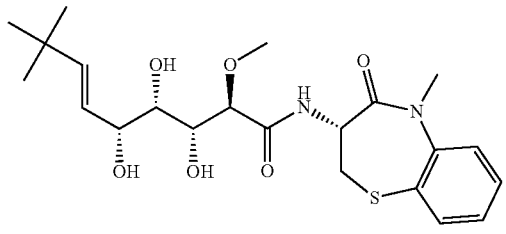

Ex4

293 mg of 5 (1.2 mmol), 441 mg of 11 (1.8 mmol) and 399 mg of sodium 2-ethylhexanoate (2.4 mmol) in 10 mL of THF are successively introduced into a 30 mL round-bottomed flask, with stirring and under an argon atmosphere. Stirring is continued at room temperature for 94 hours. 20 mL of CH₂Cl₂ are added to the reaction medium. The resulting mixture is washed with 15 mL of HCl solution (0.5 N) and then with 10 mL of water. The organic phase is dried over anhydrous magnesium sulfate, filtered and then evaporated to dryness. The crude product is chromatographed on a silica cartridge (25 g, eluent: 95/5 CH₂Cl₂/isopropanol). 345 mg of expected product Example 4 are collected.

ES: m/z=451 (M−H)⁻.

IR (KBr): 3396; 2958; 1659; 1585; 1517; 1475; 1394; 1110; 975 and 766 cm⁻¹

¹H NMR (300 MHz, DMSO-d₆), δ (ppm): 0.95 (s, 9H); 3.07 (t, J=11.5 Hz, 1H); 3.20 (s, 3H); 3.29 (partially masked m, 4H); 3.43 (dd, J=6.5 and 11.5 Hz, 1H); 3.49 (m, 1H); 3.66 (d, J=8.0 Hz, 1H); 3.91 (m, 1H); 4.32 (m, 2H); 4.41 (m, 1H); 4.52 (broad d, J=4.5 Hz, 1H); 5.28 (dd, J=7.0 and 16.0 Hz, 1H); 5.61 (broad d, J=16.0 Hz, 1H); 7.32 (m, 1H); 7.56 (m, 2H); 7.65 (d, J=7.5 Hz, 1H); 8.22 (d, J=8.0 Hz, 1H).

EXAMPLE 5

N-((3R)-9-chloro-4-oxo-7-trifluoromethyl-2,3,4,5-tetrahydro-1,5-benzothiazepin-3-yl)-(6E)-(2R,3R,4S,5R)-3,4,5-trihydroxy-2-methoxy-8,8-dimethylnon-6-enamide

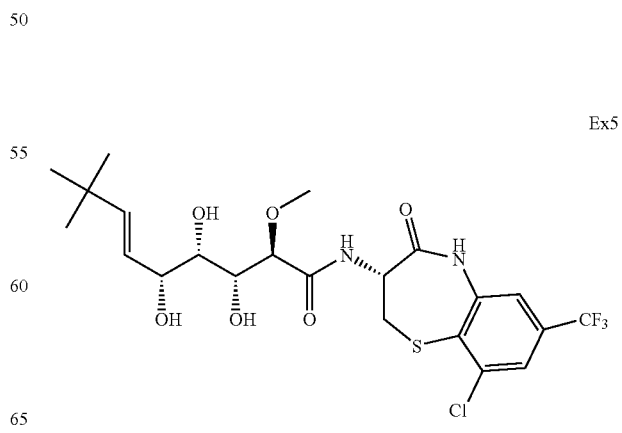

Ex5

Step 1: Preparation of (2R)-2-tert-butoxycarbonylamino-3-(2-chloro-6-nitro-4-trifluoromethylphenylsulfanyl)propionic acid (13)

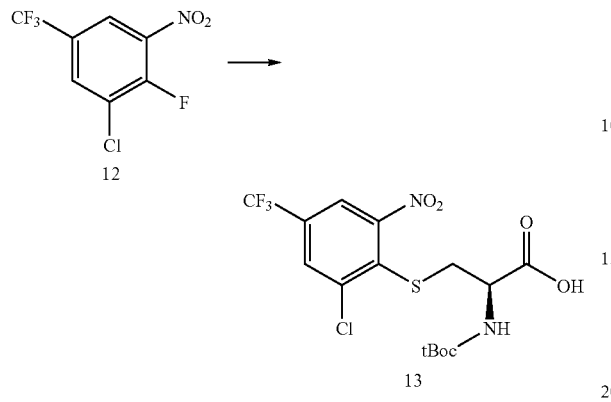

A solution of 12 (1.0 g, 4.1 mmol) in 8.6 mL of ethanol is introduced dropwise into a three-necked flask containing 0.91 g of L-Boc-Cys-OH (4.1 mmol), 7.2 mL of water and 1.0 g of NaHCO$_3$ (2.89 mmol). The medium is refluxed for 2 hours, and the ethanol is concentrated. The aqueous phase is washed with 25 mL of ether and, once the ether phase has been separated out by settling, 25 mL of EtOAc are added, and the aqueous phase is brought to pH 2-3 with HCl (1N). After stirring and separation of the phases by settling, the aqueous phase is again extracted with 25 mL of EtOAc. The organic phases are combined, dried over MgSO$_4$, filtered and then evaporated to dryness. 2.0 g of expected product 13 are obtained (yellow oil), which product is used directly in the following step.

Step 2: Preparation of (2R)-(2-amino-6-chloro-4-trifluoromethylphenylsulfanyl)-2-tert-butoxycarbonylaminopropionic acid (14)

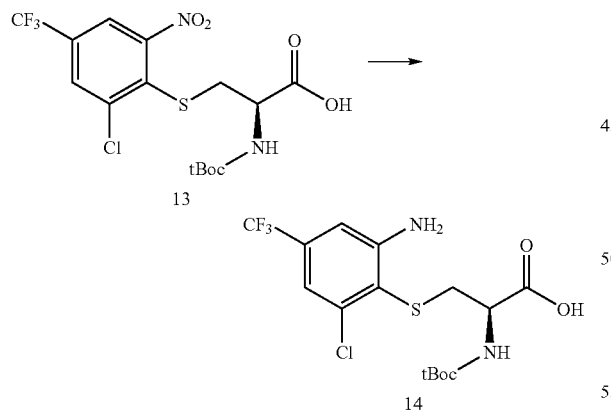

1.85 g of 13 (4.2 mmol), 186 mg of Pd/C (10%) and 45 mL of MeOH are hydrogenated at 5 bar for 5.5 hours at 20° C. in an autoclave. After filtering off the catalyst through Celite and evaporating off the solvent, 1.45 g of expected product 14 are obtained, which product is used directly in the following step.

$^1$H NMR (300 MHz, DMSO-d$_6$), δ (ppm): 1.36 (broad s, 9H); 3.01 (m, 1H); 3.10 (dd, J=4.5 and 13.5 Hz, 1H); 3.98 (m, 1H); 6.25 (broad s, 2H); 6.94 (d, J=2.0 Hz, 1H); 7.00 (d, J=2.0 Hz, 1H); 7.14 (broad d, J=8.0 Hz, 1H); 12.8 (very broad m, 1H).

Step 3: Preparation of tert-butyl ((3R)-9-chloro-4-oxo-7-trifluoromethyl-2,3,4,5-tetrahydro-1,5-benzothiazepin-3-yl)carbamate (15)

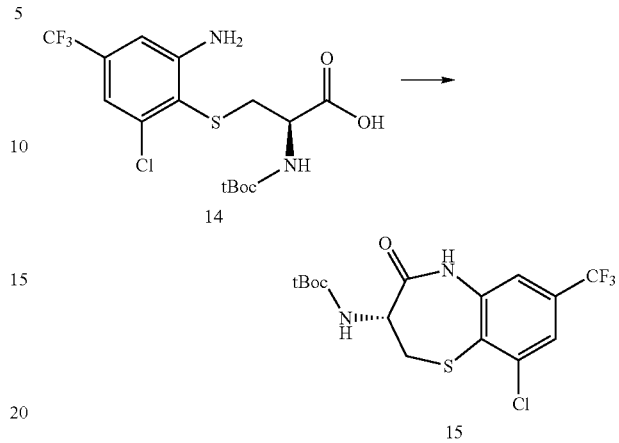

A solution of EDCI (0.624, 3.3 mmol, 1-(3-dimethylaminopropyl)-3-ethylcarbodiimide hydrochloride) and 1-hydroxybenzotriazole (0.44 g, 3.3 mmol) in 200 mL of CH$_2$Cl$_2$ is introduced into a 500 mL three-necked flask containing 1.35 g of 14 (3.3 mmol), 50 mL of CH$_2$Cl$_2$ and 0.325 g of TEA (3.3 mmol), at 0° C. The reaction medium is allowed to warm to room temperature, and is stirred for 24 hours. The medium is washed with twice 200 mL of water. The organic phase is dried over MgSO$_4$, filtered and evaporated to dryness. The crude product is chromatographed on a silica cartridge (70 g) eluting with CH$_2$Cl$_2$/MeOH (gradient: MeOH 0 to 5%). 0.44 g of expected product 15 is obtained (beige-coloured foam).

$^1$H NMR (300 MHz, DMSO-d$_6$), δ (ppm): 1.34 (s, 9H); 3.24 (t, J=11.5 Hz, 1H); 3.58 (dd, J=7.0 and 11.5 Hz, 1H); 4.12 (m, 1H); 7.34 (d, J=8.0 Hz, 1H); 7.43 (broad s, 1H); 7.84 (broad s, 1H); 10.3 (s, 1H).

Step 4: Preparation of (3R)-3-amino-9-chloro-7-trifluoromethyl-2,3-dihydro-5H-1,5-benzothiazepin-4-one hydrochloride (16)

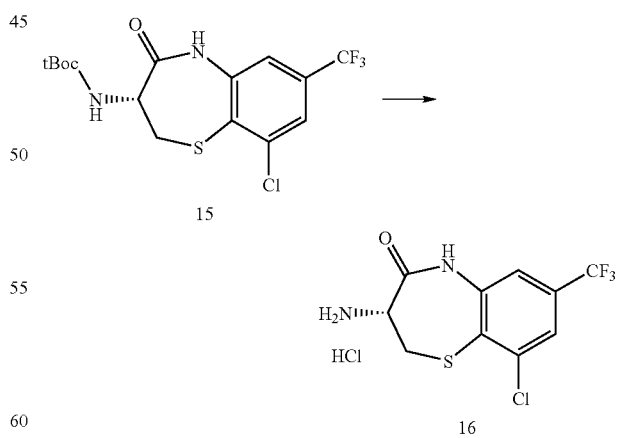

11 mL of a solution of hydrogen chloride in dioxane (4 M) are added to a 25 mL round-bottomed flask containing 582 mg of 15 (1.47 mmol). The mixture is stirred for 4 hours at room temperature under argon. A white precipitate forms, which is filtered off by suction and washed with 3 mL of dioxane and then 5 mL of isopropyl ether. 450 mg of amine 16 are thus obtained in the form of the hydrochloride.

$^1$H NMR (400 MHz, DMSO-d$_6$), δ (ppm): 3.39 (t, J=11.5 Hz, 1H); 3.79 (dd, J=7.0 and 11.5 Hz, 1H); 4.18 (dd, J=7.0 and 11.5 Hz, 1H); 7.43 (d, J=2.0 Hz, 1H); 7.91 (d, J=2.0 Hz, 1H); 8.57 (broad s, 3H); 10.9 (s, 1H).

Step 5: Preparation of N-((3R)-9-chloro-4-oxo-7-trifluoromethyl-2,3,4,5-tetrahydro-1,5-benzothiazepin-3-yl)-(6E)-(2R,3R,4S,5R)-3,4,5-trihydroxy-2-methoxy-8,8-dimethylnon-6-enamide (Example 5)

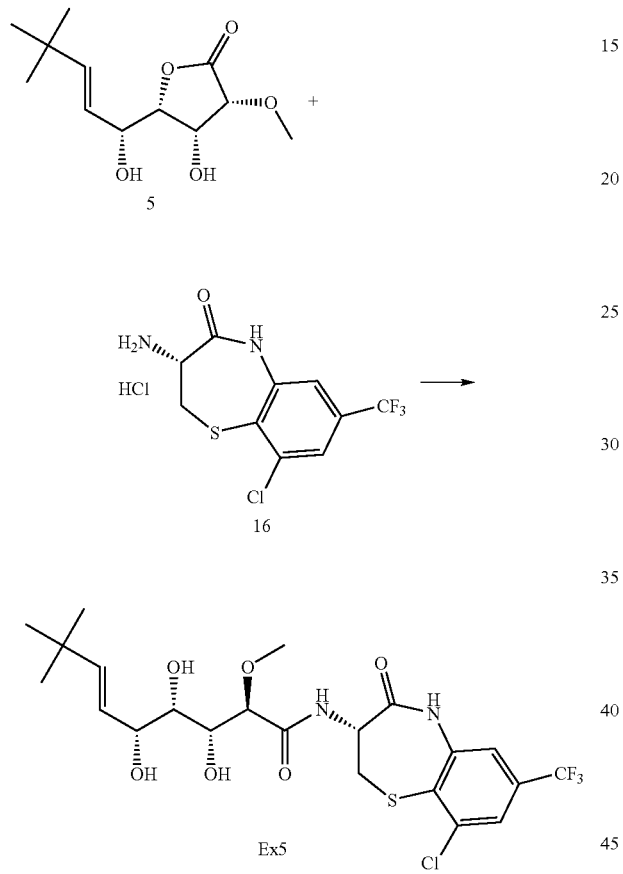

210 mg of 5 (0.43 mmol), 287 mg of 16 (0.86 mmol) and 179 mg of sodium 2-ethylhexanoate (1.1 mmol) in 2.5 mL of THF are successively introduced into a 25 mL round-bottomed flask, with stirring and under an argon atmosphere. Stirring is continued at room temperature for 24 hours. 10 mL of ethyl acetate are added to the reaction medium. The resulting mixture is washed successively with twice 10 mL of HCl solution (1N). The organic phase is dried over anhydrous magnesium sulfate, filtered and then evaporated to dryness. The crude product is chromatographed on a silica cartridge (20 g, CH$_2$Cl$_2$/MeOH eluent: as an MeOH gradient: 0 to 10%). 176 mg of expected product Example 5 are collected.

ES: m/z=539 (M−H)$^-$.

$^1$H NMR (400 MHz, DMSO-d$_6$), δ (ppm): 0.95 (s, 9H); 3.19 (s, 3H); from 3.27 to 3.38 (masked m, 2H); 3.49 (m, 1H); 3.58 (dd, J=7.0 and 11.5 Hz, 1H); 3.67 (d, J=8.0 Hz, 1H); 3.93 (m, 1H); 4.27 (d, J=7.5 Hz, 1H); 4.31 (d, J=5.5 Hz, 1H); 4.45 (m, 1H); 4.55 (d, J=4.5 Hz, 1H); 5.28 (dd, J=7.0 and 16.0 Hz, 1H); 5.62 (d, J=16.0 Hz, 1H); 7.42 (d, J=2.0 Hz, 1H); 7.86 (d, J=2.0 Hz, 1H); 8.35 (d, J=7.5 Hz, 1H); 10.45 (s, 1H).

EXAMPLE 6

N-((3R)-9-bromo-4-oxo-2,3,4,5-tetrahydro-1,5-benzothiazepin-3-yl)-(6E)-(2R,3R,4S,5R)-3,4,5-trihydroxy-2-methoxy-8,8-dimethylnon-6-enamide

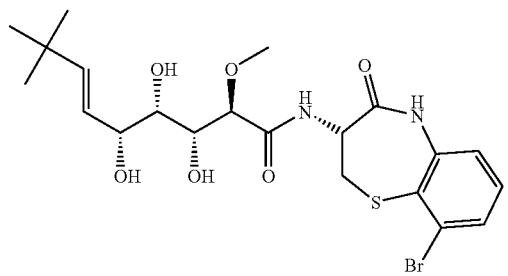

Step 1: Preparation of (3R)-(2-bromo-6-nitrophenylsulfanyl)-2-tert-butoxy-carbonylaminopropionic acid (18)

A solution of 17 (3.0 g, 13.6 mmol) in 28.5 mL of ethanol is introduced dropwise into a three-necked flask containing 3.02 g of L-Boc-Cys-OH (13.6 mmol), 24 mL of water and 3.31 g of NaHCO$_3$ (39.4 mmol). The medium is refluxed for 2 hours, and the ethanol is then evaporated off. The aqueous phase is then washed with 50 mL of ether, and once the ether phase has been separated out by settling, a further 25 mL of EtOAc are added and the aqueous phase is brought to pH 2-3 with HCl (1N). After stirring and separation of the phases by settling, the aqueous phase is again extracted with 50 mL of EtOAc. The organic phases are combined, dried over MgSO$_4$, filtered and finally evaporated to dryness. 5.92 g of expected product 18 are obtained, which product is used directly for the following step.

$^1$H NMR (400 MHz, DMSO-d$_6$), δ (ppm): 1.36 (s, 9H); 3.12 (dd, J=9.5 and 13.0 Hz, 1H); 3.32 (dd, J=4.5 and 13.0 Hz, 1H); 3.93 (m, 1H); 7.09 (d, J=8.5 Hz, 1H); 7.55 (t, J=7.5 Hz, 1H); 7.90 (broad d, J=7.5 Hz, 1H); 8.05 (broad d, J=7.5 Hz, 1H); 12.7 (broad m, 1H).

Step 2: Preparation of (3R)-3-(2-amino-6-bromophenylsulfanyl)-2-tert-butoxycarbonylaminopropionic acid (19)

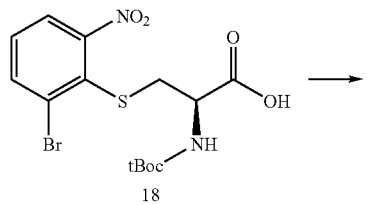
18

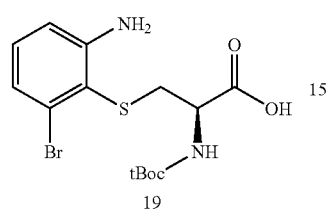
19

5.92 g of 18 (14.1 mmol), 882 mg of Pd/C (10%) and 100 mL of MeOH are hydrogenated under 5 bar for five hours at 20° C. in an autoclave. After filtering off the catalyst through Celite, the solvent is evaporated off to give 5.1 g of expected product 19, which product is used directly in the following step.

$^1$H NMR (400 MHz, DMSO-d$_6$), δ (ppm): 1.37 (s, 9H); 2.92 (dd, J=9.5 and 13.0 Hz, 1H); 3.02 (dd, J=4.5 and 13.0 Hz, 1H); 3.95 (m, 1H); 6.72 (broad d, J=8.0 Hz, 1H); 6.83 (broad d, J=8.0 Hz, 1H); 6.96 (t, J=8.0 Hz, 1H); 7.22 (masked m, 1H); 12.75 (broad m, 1H).

Step 3: Preparation of tert-butyl ((3R)-9-bromo-4-oxo-2,3,4,5-tetrahydro-1,5-benzothiazepin-3-yl)carbamate (20)

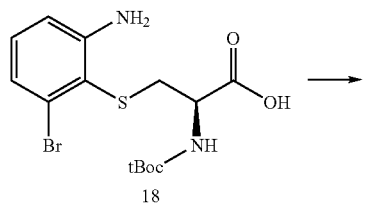
18

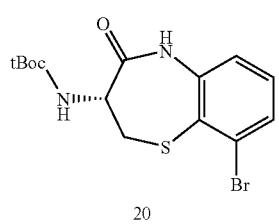
20

A solution of EDCI (2.46, 12.8 mmol, 1-(3-dimethylaminopropyl)-3-ethylcarbodiimide hydrochloride) and 1-hydroxybenzotriazole (1.73 g, 12.8 mmol) in 65 mL of CH$_2$Cl$_2$ is introduced, at 0° C., into a 500 mL three-necked flask containing 5.02 g of 19 (12.8 mmol), 150 mL of CH$_2$Cl$_2$ and 1.30 g of TEA (12.8 mmol). The reaction medium is allowed to warm to room temperature and stirring is continued for 24 hours. The medium is washed with twice 500 mL of water. The organic phase is dried over MgSO$_4$, filtered and then evaporated to dryness. The crude product is chromatographed on a silica cartridge (300 g) eluting with CH$_2$Cl$_2$/MeOH (as a gradient: 0 to 5% MeOH). 2.91 g of expected product 20 are obtained (beige-coloured foam).

$^1$H NMR (400 MHz, DMSO-d$_6$), δ (ppm): 1.33 (s, 9H); 3.13 (t, J=12.0 Hz, 1H); 3.52 (dd, J=7.0 and 12.0 Hz, 1H); 4.04 (m, 1H); 7.17 (broad d, J=8.0 Hz, 1H); 7.28 (d, J=8.0 Hz, 1H); 7.34 (t, J=8.0 Hz, 1H); 7.59 (broad d, J=8.0 Hz, 1H); 10.15 (s, 1H).

Step 4: Preparation of (3R)-3-amino-9-bromo-2,3-dihydro-5H-1,5-benzothiazepin-4-one hydrochloride (21)

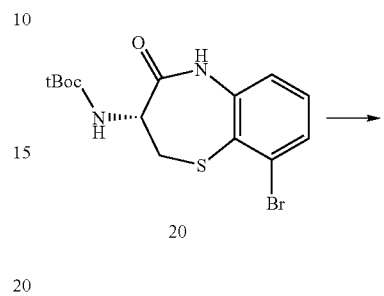
20

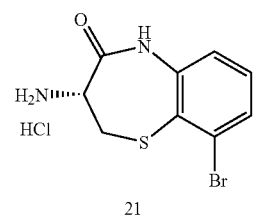
21

10 mL of a solution of hydrogen chloride in dioxane (4 M) are added to a 25 mL round-bottomed flask containing 500 mg of 20 (1.34 mmol). The mixture is stirred for 4 hours at room temperature under argon. A white precipitate forms, which is filtered off by suction and washed with 3 mL of dioxane and then 5 mL of isopropyl ether. 386 mg of amine 21 (beige-coloured solid) are thus obtained in the form of hydrochloride.

$^1$H NMR (300 MHz, DMSO-d$_6$), δ (ppm): 3.29 (t, J=11.5 Hz, 1H); 3.78 (dd, J=7.0 and 11.5 Hz, 1H); 3.96 (m, 1H); 7.19 (dd, J=1.5 and 8.0 Hz, 1H); 7.38 (t, J=8.0 Hz, 1H); 7.64 (dd, J=1.5 and 8.0 Hz, 1H); 8.53 (broad s, 3H); 10.75 (s, 1H).

Step 5: Preparation of N-((3R)-9-bromo-4-oxo-2,3,4,5-tetrahydro-1,5-benzothiazepin-3-yl)-(6E)-(2R,3R,4S,5R)-3,4,5-trihydroxy-2-methoxy-8,8-dimethylnon-6-enamide (Example 6)

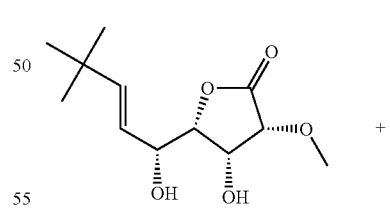
5

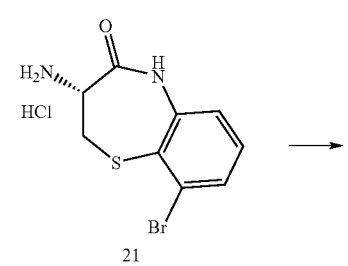
21

-continued

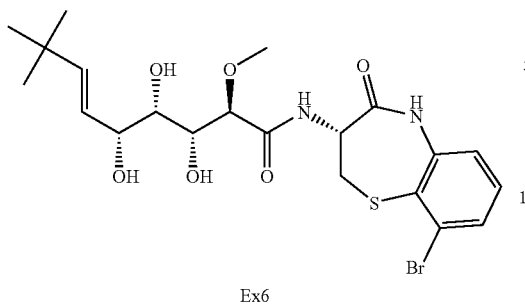

Ex6

80 mg of 5 (327 µmol), 101 mg of 21 (327 µmol) and 163 mg of sodium 2-ethylhexanoate (0.98 mmol) in 2.0 mL of THF are successively introduced into a 25 mL round-bottomed flask, with stirring and under an argon atmosphere. Stirring is continued at room temperature for 24 hours. 5 mL of ethyl acetate are added to the reaction medium. The resulting mixture is washed successively with 5 mL of HCl solution (1N), 5 mL of saturated NaHCO₃ and 5 mL of water. The organic phase is dried over anhydrous magnesium sulfate, filtered and then evaporated to dryness. The crude product is chromatographed on a silica cartridge (5 g, $CH_2Cl_2$/MeOH eluent as a gradient: 1% to 10% MeOH). 95 mg of expected product Example 6 are collected.

ES: m/z=515 (M-H)⁻.

¹H NMR (400 MHz, DMSO-d₆), δ (ppm): 0.96 (s, 9H); from 3.17 to 3.32 (partially masked m, 2H); 3.20 (s, 3H); 3.49 (m, 1H); 3.53 (partially masked dd, J=7.0 and 11.5 Hz, 1H); 3.68 (d, J=8.0 Hz, 1H); 3.93 (m, 1H); 4.30 (m, 2H); 4.38 (m, 1H); 4.57 (d, J=4.5 Hz, 1H); 5.29 (dd, J=7.0 and 16.0 Hz, 1H); 5.62 (d, J=16.0 Hz, 1H); 7.18 (broad d, J=7.5 Hz, 1H); 7.35 (t, J=7.5 Hz, 1H); 7.61 (broad d, J=7.5 Hz, 1H); 8.29 (d, J=7.5 Hz, 1H); 10.3 (s, 1H).

EXAMPLE 7

N-((3R)-8-chloro-4-oxo-2,3,4,5-tetrahydro-1,5-benzothiazepin-3-yl)-(6E)-(2R,3R,4S,5R)-3,4,5-trihydroxy-2-methoxy-8,8-dimethylnon-6-enamide

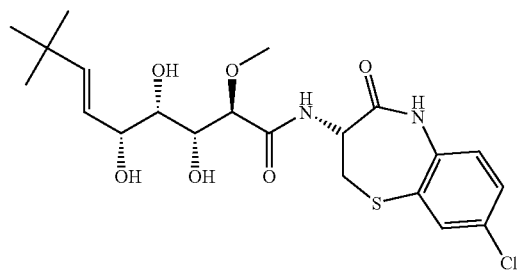

Ex7

Step 1: Preparation of (3R)-3-(3-chloro-6-nitrophenylsulfanyl)-2-tert-butoxy-carbonylaminopropionic acid (23)

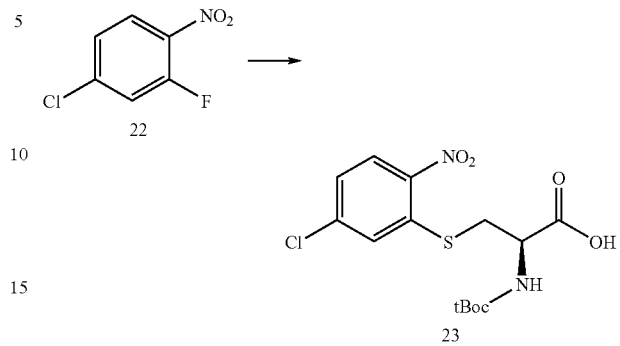

A solution of 22 (1.0 g, 5.7 mmol) in 12 mL of ethanol is introduced dropwise into a three-necked flask containing 1.26 g of L-Boc-Cys-OH (5.70 mmol), 10 mL of water and 1.38 g of NaHCO₃ (16.5 mmol). The medium is refluxed for 6 hours. The ethanol is evaporated off. The aqueous phase is then washed with 30 mL of ether, and once the ether phase has been separated out by settling, the aqueous phase is acidified to pH 2-3 with HCl (1N) and then extracted with twice 30 mL of CH₂Cl₂. The organic phases are combined, dried over MgSO₄, filtered and then evaporated to dryness. 2.1 g of expected product 23 (yellow foam) are obtained, which product is used for the following step.

¹H NMR (400 MHz, DMSO-d₆), δ (ppm): 1.35 (s, 9H); 3.24 (dd, J=10.0 and 13.5 Hz, 1H); 3.59 (dd, J=4.0 and 13.5 Hz, 1H); 4.13 (m, 1H); 7.29 (broad d, J=9.0 Hz, 1H); 7.48 (dd, J=2.0 and 9.0 Hz, 1H); 7.72 (d, J=2.0 Hz, 1H); 8.20 (d, J=9.0 Hz, 1H); 13.0 (broad m, 1H).

Step 2: Preparation of (3R)-3-(2-amino-4-chlorophenylsulfanyl)-2-tert-butoxy-carbonylaminopropionic acid (24)

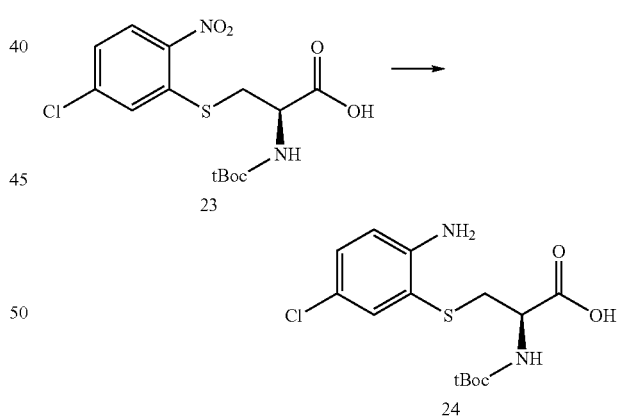

7.3 g of zinc (0.11 mol) are placed in a three-necked flask containing 2.1 g of 23 (5.55 mmol), 0.59 g of ammonium chloride and 70 mL of MeOH. The reaction medium is stirred at room temperature for 2 hours and then heated at 75° C. for 2 hours. The resulting mixture is filtered through Celite and washed with 20 mL of boiling MeOH. The mixture is evaporated to dryness and the crude residue is taken up in 50 mL of water and then extracted with twice 50 mL of CH₂Cl₂. The combined organic phases are dried over MgSO₄, filtered and evaporated to dryness to give 1.62 g of expected product 24 (cream-coloured foam), which product is used for the following step.

¹H NMR (400 MHz, DMSO-d₆), δ (ppm): 1.36 (s, 9H); 2.93 (dd, J=8.5 and 13.0 Hz, 1H); 3.12 (dd, J=4.0 and 13.0 Hz, 1H); 3.93 (m, 1H); 5.49 (broad s, 2H); 6.59 (broad d, J=8.0 Hz, 1H); 6.70 (d, J=8.5 Hz, 1H); 7.04 (dd, J=2.5 and 8.5 Hz, 1H); 7.26 (d, J=2.5 Hz, 1H).

Step 3: Preparation of tert-butyl (3R)-8-chloro-4-oxo-2,3,4,5-tetrahydro-1,5-benzothiazepin-3-yl)carbamate (25)

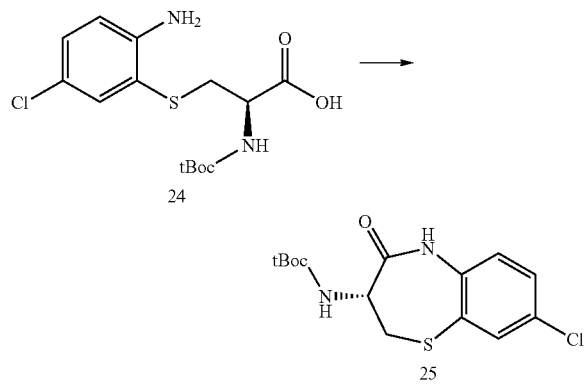

2.07 g of benzotriazol-1-yloxytris(dimethylamino)phosphonium hexafluoride (4.67 mmol) and 1.96 g of NaHCO₃ are placed in a 100 mL round-bottomed flask containing 1.62 g of 24 (4.67 mmol) and 30 mL of DMF. The reaction medium is stirred for 24 hours at room temperature. 70 mL of EtOAc are added and the mixture is then washed with 50 mL of HCl (1N), 50 mL of saturated NaHCO₃ solution and 50 mL of water. The organic phase is dried over MgSO₄, filtered and evaporated to dryness. The crude product is chromatographed on a silica cartridge (40 g) eluting with heptane/EtOAc (as an EtOAc gradient: 12% to 50%). 1.14 g of expected product 25 are obtained (pale yellow foam).

¹H NMR (400 MHz, DMSO-d₆), δ (ppm): 1.33 (s, 9H); 3.10 (t, J=11.5 Hz, 1H); 3.54 (dd, J=7.0 and 11.5 Hz, 1H); 4.08 (m, 1H); 7.16 (d, J=8.5 Hz, 1H); 7.27 (d, J=8.5 Hz, 1H); 7.51 (dd, J=2.5 and 8.5 Hz, 1H); 7.64 (d, J=2.5 Hz, 1H); 10.1 (s, 1H).

Step 4: Preparation of (3R)-3-amino-8-chloro-2,3-dihydro-5H-1,5-benzothiazepin-4-one hydrochloride (26)

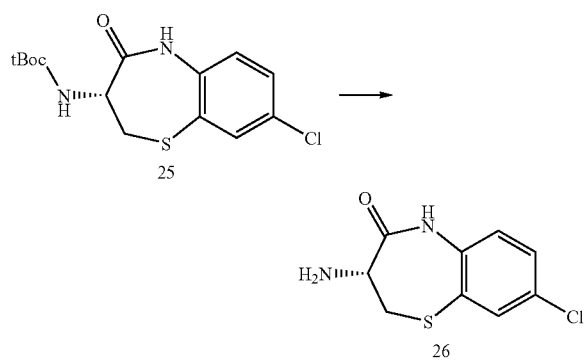

10 mL of a solution of hydrogen chloride in dioxane (4 M) are added to a 25 mL round-bottomed flask containing 500 mg of 25 (1.52 mmol). The mixture is stirred for 4 hours at room temperature under argon. A white precipitate forms, which is filtered off by suction and washed with 5 mL of dioxane and then 5 mL of isopropyl ether, to give, after drying under vacuum, 510 mg of amine 26 (in the form of the hydrochloride).

¹H NMR (400 MHz, DMSO-d₆), δ (ppm): 3.26 (t, J=11.5 Hz, 1H); 3.81 (dd, J=7.0 and 11.5 Hz, 1H); 3.97 (dd, J=7.0 and 11.5 Hz, 1H); 7.20 (d, J=8.5 Hz, 1H); 7.55 (dd, J=2.5 and 8.5 Hz, 1H); 7.70 (d, J=2.5 Hz, 1H); 8.55 (broad s, 3H); 10.65 (s, 1H).

Step 5: Preparation of N-((3R)-8-chloro-4-oxo-2,3,4,5-tetrahydro-1,5-benzothiazepin -3-yl)-(6E)-(2R,3R,4S,5R)-3,4,5-trihydroxy-2-methoxy-8,8-dimethylnon-6-enamide (Example 7)

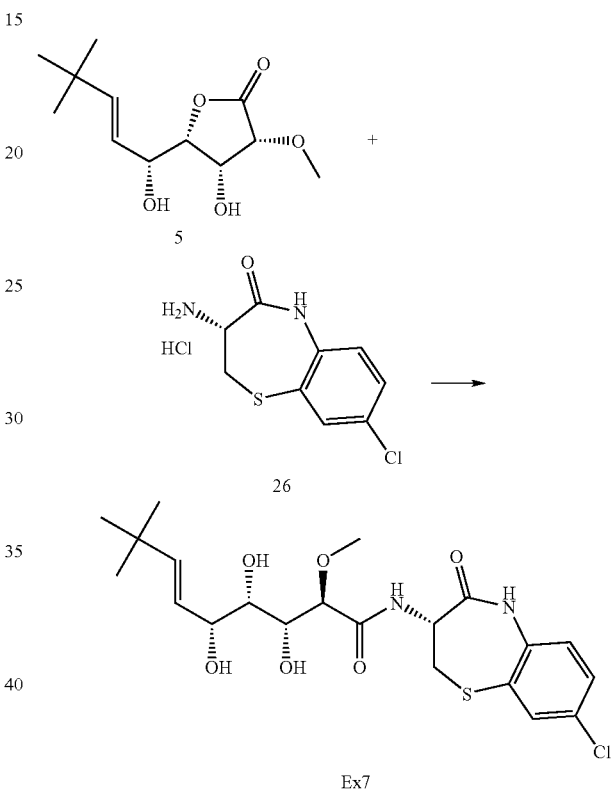

87 mg of 5 (352 μmol), 187 mg of 26 (704 μmol) and 146 mg of sodium 2-ethylhexanoate (0.88 mmol) in 2.0 mL of THF are successively introduced into a 25 mL round-bottomed flask, with stirring and under an argon atmosphere. Stirring is continued at room temperature for 24 hours. 5 mL of ethyl acetate are added to the reaction medium. The resulting mixture is washed successively with 5 mL of HCl solution (1N), 5 mL of saturated aqueous NaHCO₃ solution and 5 mL of water. The organic phase is dried over anhydrous magnesium sulfate, filtered and then evaporated to dryness. The crude product is chromatographed on a silica cartridge (25 g, CH₂Cl₂/MeOH eluent: as an MeOH gradient: 1% to 10%). 70 mg of expected product Example 7 are collected.

ES: m/z=495 MNa⁺; m/z=473 M H⁺.

¹H NMR (300 MHz, DMSO-d₆), δ (ppm): 0.96 (s, 9H); 3.18 (partially masked t, J=11.5 Hz, 1H); 3.21 (s, 3H); from 3.25 to 3.34 (masked m, 1H); 3.49 (m, 1H); 3.56 (dd, J=7.0 and 11.5 Hz, 1H); 3.67 (d, J=8.0 Hz, 1H); 3.91 (m, 1H); 4.29 (broad m, 2H); 4.41 (m, 1H); 4.53 (broad m, 1H); 5.28 (dd, J=7.0 and 16.0 Hz, 1H); 5.62 (d, J=16.0 Hz, 1H); 7.17 (d, J=8.5 Hz, 1H); 7.52 (dd, J=2.0 and 8.5 Hz, 1H); 7.67 (d, J=2.0 Hz, 1H); 8.24 (broad d, J=8.0 Hz, 1H); 10.2 (s, 1H).

EXAMPLE 8

(6E)-(2R,3R,4S,5R)-8-ethyl-3,4,5-trihydroxy-2-methoxy-N-((3R)-5-methyl-4-oxo-2,3,4,5-tetrahydro-1,5-benzothiazepin-3-yl)dec-6-enamide

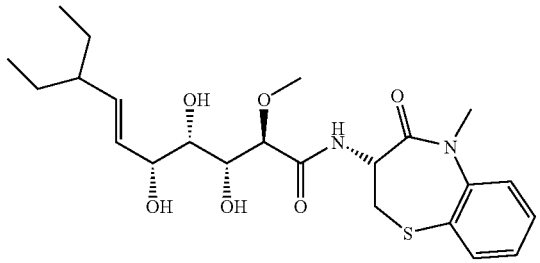

Step 1: Preparation of (4R,4aS,7R,7aR)-7-methoxy-2,2-dimethyl-4-vinyl-tetrahydrofuro[3,2-d]-1,3-dioxin-6-one (28)

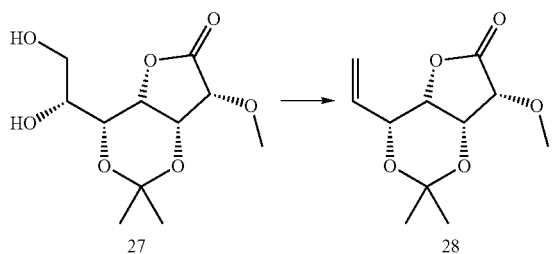

178.2 g of PPh₃ (0.679 mol), 84.1 g of imidazole (1.235 mol) and 2430 mL of anhydrous THF are placed in a 4000 mL round-bottomed flask under nitrogen, equipped with a mechanical stirrer. 156.8 g of bisublimed iodine (0.618 mol) are added cautiously, while maintaining the temperature of the reaction mixture at 30° C. This medium is refluxed (66° C.) for 1 hour, followed by gradual addition of 81 g of 27 (0.309 mol) (which may be prepared according to the procedures described in Org. Process Res. Dev. 2003, 7(6), 856-865) at 66° C.±2° C. The homogeneous medium thus obtained is refluxed for 3 hours. The medium is allowed to cool to 20° C.±5° C., followed by addition of 1000 mL of 10% NaHCO₃ solution (effervescence, athermic) (pH 8.0-8.5). 185.5 g of Na₂S₂O₃ are then added until the mixture has almost totally decolorized (appearance of a mineral precipitate). After stirring at 20° C.±5° C. for 30 minutes, the solid is filtered off and rinsed with THF. The THF/H₂O filtrate is partially concentrated on a rotary evaporator at a temperature below 35° C. The aqueous concentrate is saturated with NaCl and extracted with 1500 mL of CH₂Cl₂. The organic phase is dried over MgSO₄, filtered and evaporated to dryness. The residue is taken up in 2000 mL of an H₂O/acetone mixture (75/25), and the insoluble matter is filtered off and rinsed with the H₂O/acetone mixture (75/25). The filtrates are concentrated on a rotary evaporator at 50° C. and 20 mbar, and filtered again through a sinter funnel (porosity No. 4). The aqueous phase is saturated with NaCl and extracted three times with CH₂Cl₂ (1000 mL, 500 mL, and 250 mL). The organic phases are combined, dried over MgSO₄, filtered and evaporated to dryness to give 60 g of crude product, which is dissolved in 250 mL of CH₂Cl₂. 30 g of silica are then added to the solution. After stirring for 15 minutes, the silica is filtered off and rinsed twice with CH₂Cl₂ (250 mL and 100 mL). The filtrate is concentrated to dryness and dried at 1 mbar and 20° C. to give 54.8 g of expected product 28 (white solid)

¹H NMR (300 MHz, DMSO-d₆), δ (ppm): 5.85 (m, 1H); 5.35 (d, 1H); 5.25 (d, 1H); 4.80 (m, 1H); 4.69 (m, 1H); 4.43 (d, 1H); 4.22 (m, 1H); 3.40 (s, 3H); 1.49 (s, 3H); 1.30 (s, 3H).

Step 2: Preparation of (3R,4R,5S)-4-hydroxy-5-((1R)-hydroxyallyl)-3-methoxydihydrofuran-2-one (29)

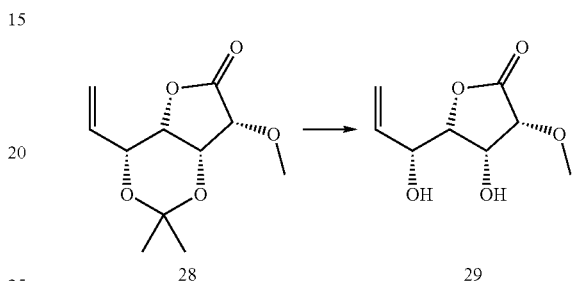

10 mL of TFA are added dropwise to a 100 mL round-bottomed flask containing 1.0 g of 28 (4.38 mmol), 10 mL of water and 14 mL of THF, at 0° C. The medium is allowed to warm to room temperature and is stirred overnight. The medium is then concentrated under reduced pressure at room temperature, followed by addition of 50 mL of water, freezing and freeze-drying. The lyophilizate is slurried in heptane in the presence of a minimum amount of methanol and, after evaporation of the solvents, 778 mg of the expected 29 are obtained (white solid).

MS: m/z=211 [M+Na]⁺, 189 [M+H]⁺

¹H NMR (400 MHz, DMSO-d₆), δ (ppm): 3.42 (s, 3H); 3.98 (dd, J=2.5 and 9.0 Hz, 1H); from 4.25 to 4.34 (m, 3H); 5.22 (dm, J=10.5 Hz, 1H); 5.29 (d, J=5.0 Hz, 1H); 5.44 (partially masked d, J=16.5 Hz, 1H); 5.46 (m, 1H); 5.97 (m, 1H).

Step 3: Preparation of ((3R,4R,5S)-5-((2E)-(1R)-4-ethyl-1-hydroxyhex-2-enyl)-4-hydroxy-3-methoxydihydrofuran-2-one (30)

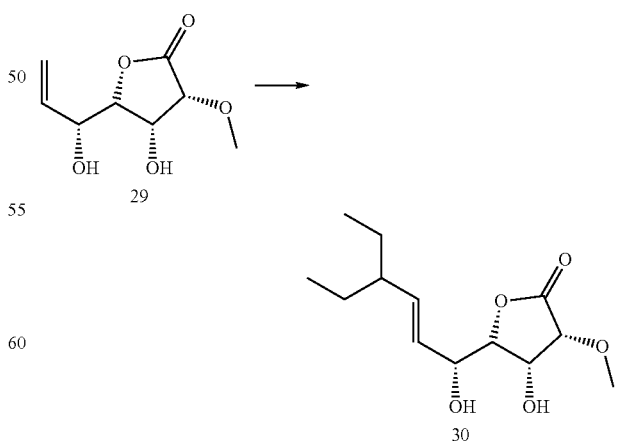

100 mg of 29 (0.53 mmol), 0.52 g of 3-ethyl-1-pentene (5.3 mmol), 4 mL of CH₂Cl₂ and 90 mg of Grubbs second-generation catalyst (C$_{46}$H$_{65}$Cl$_2$N$_2$PRu, MW 848.98, 0.11 mmol) are placed in a 5 mL vial. The encapsulated brick-red solution is heated for 10 minutes at 60° C. by microwave (Smithsynthesizer, 300 Watt). The solvent is evaporated off and the crude product is chromatographed on a silica cartridge (25 g) eluting with a mixture of heptane/EtOAc (55/45). 54 mg of expected product 30 are obtained (brown solid).

$^1$H NMR (300 MHz, DMSO-d$_6$), δ (ppm): 0.81 (t, J=7.5 Hz, 6H); 1.23 (m, 4H); from 1.32 to 1.49 (m, 2H); 1.78 (m, 1H); 3.42 (s, 3H); 3.97 (d, J=9.0 Hz, 1H); 4.20 to 4.31 (m, 3H); 5.11 to 5.75 (m, 4H).

Step 4: Preparation of (6E)-(2R,3R,4S,5R)-8-ethyl-3,4,5-trihydroxy-2-methoxy-N -((3R)-5-methyl-4-oxo-2,3,4,5-tetrahydro-1,5-benzothiazepin-3-yl)dec-6-enamide (Example 8)

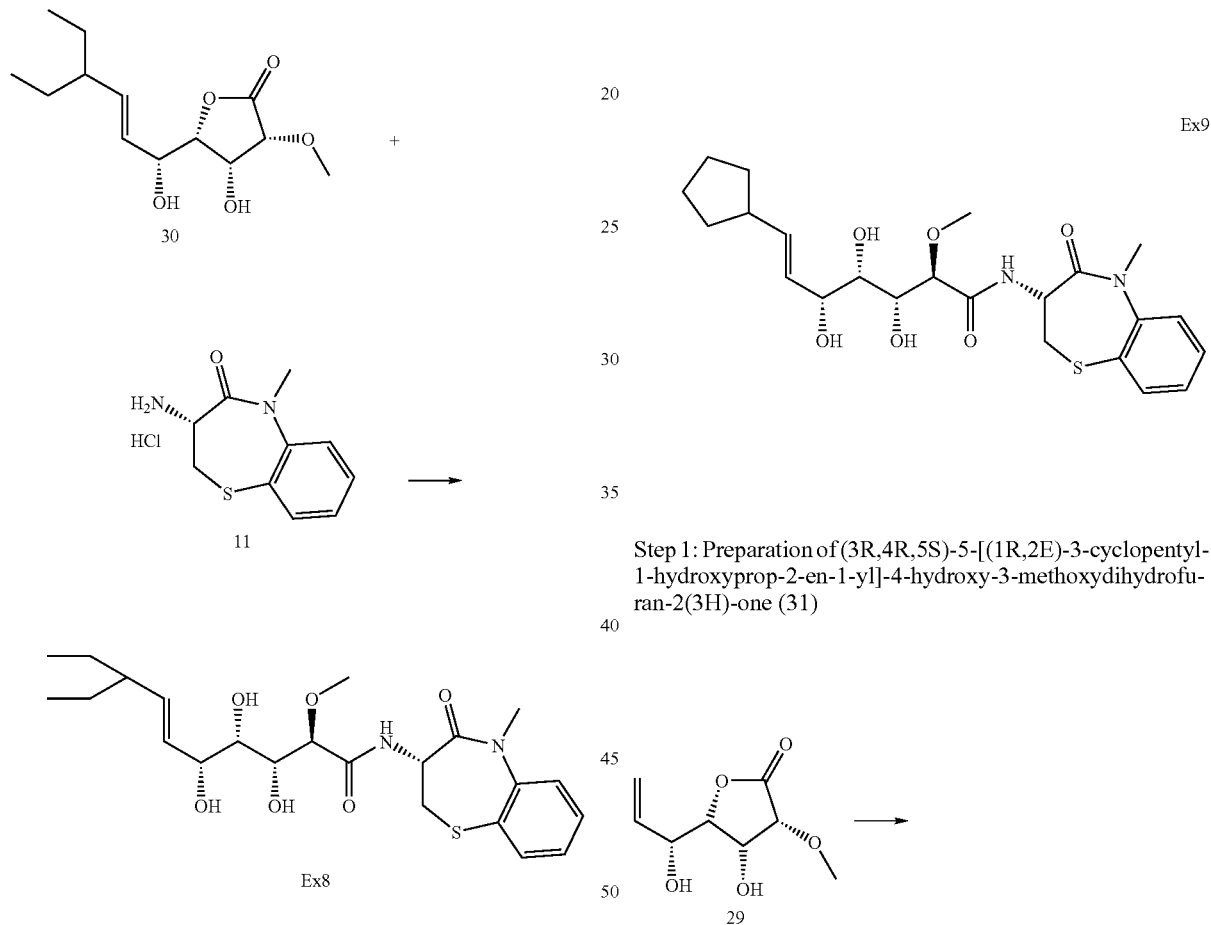

50 mg of 30 (0.19 mmol), 71 mg of 11 (0.29 mmol) and 64 mg of sodium 2-ethylhexanoate (0.39 mmol) in 2.0 mL of THF are successively introduced into a 30 mL round-bottomed flask, with stirring and under an argon atmosphere. Stirring is continued at room temperature for 96 hours. 4 mL of CH$_2$Cl$_2$ are added to the reaction medium. The resulting mixture is washed successively with 3 mL of HCl solution (0.5N) and 3 mL of water. The aqueous phase is re-extracted with twice 4 mL of CH$_2$Cl$_2$. The combined organic phases are dried over anhydrous magnesium sulfate, filtered and then evaporated to dryness. The crude product is chromatographed on a silica cartridge (12 g, eluent: 95/5 CH$_2$Cl$_2$/isopropanol). 63 mg of expected product Example 8 are collected.

ES: m/z=465 (M–H)$^-$.

$^1$H NMR (400 MHz, DMSO-d$_6$), δ (ppm): 0.75 to 0.82 (m, 6H); 1.10 to 1.37 (m, 4H); 1.70 (m, 1H); 3.06 (t, J=11.5 Hz, 1H); 3.20 (s, 3H); 3.25 to 3.3 (m, 4H); 3, 44 (dd, J=7.0 and 11, 5 Hz, 1H); 3.50 (m, 1H); 3.65 (d, J=8.0 Hz, 1H); 3.92 (m, 1H); 4.30 (br m, 2H); 4.41 (m, 1H); 4.51 (m, 1H); 5.26 to 5.37 (m, 2H); 7.32 (m, 1H); 7.57 (m, 1H); 7.66 (d, J=7.5 Hz, 1H); 8.20 (br d, J=8.0 Hz, 1H).

EXAMPLE 9

(2R,3R,4S,5R,6E)-7-cyclopentyl-3,4,5-trihydroxy-2-methoxy-N-[(3R)-5-methyl-4-oxo-2,3,4,5-tetrahydro-1,5-benzothiazepin-3-yl]hept-6-enamide Step 1: Preparation of (3R,4R,5S)-5-[(1R,2E)-3-cyclopentyl-1-hydroxyprop-2-en-1-yl]-4-hydroxy-3-methoxydihydrofuran-2(3H)-one (31)

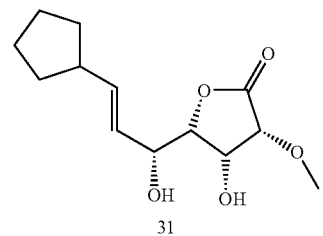

100 mg (0.53 mmol) of 22, 4 mL of $CH_2Cl_2$, 726 μL (5.3 mmol) of vinylcyclopentane and then 90.2 mg (106 μmol) of Grubbs second-generation catalyst are placed in a 5 mL vial. The solution is heated at 60° C. for 10 minutes by microwave. The solvent is then evaporated to dryness under reduced pressure and the residue is then purified on a Biotage 12-M silica column (eluent: 40/60 heptane/EtOAc). Product 31 (76.3 mg, Rf=0.35 under the elution conditions used) is obtained in the form of a brown solid.

MS: m/z=279 $[M+Na]^+$, 257 $[M+H]^+$ $^1$H NMR (300 MHz, DMSO-$d_6$), δ (ppm): 5.82 (dd, 1H, J=8 Hz and 16 Hz), 5.50 (dd, 1H, J=6 Hz and 16 Hz), 5.39 (d, 1H, J=4.5 Hz), 5.15 (d, 1H, J=6 Hz), 4.27 (m, 3H), 3.95 (dd, 1H, J=3 Hz and 8 Hz), 3.41 (s, 3H), 2.43 (m, 1H), 1.73 (m, 2H), 1.56 (m, 4H), 1.26 (m, 2H).

Step 2: Preparation of (2R,3R,4S,5R,6E)-7-cyclopentyl-3,4,5-trihydroxy-2-methoxy-N -[(3R)-5-methyl-4-oxo-2,3,4,5-tetrahydro-1,5-benzothiazepin-3-yl]hept-6-enamide (Example 9)

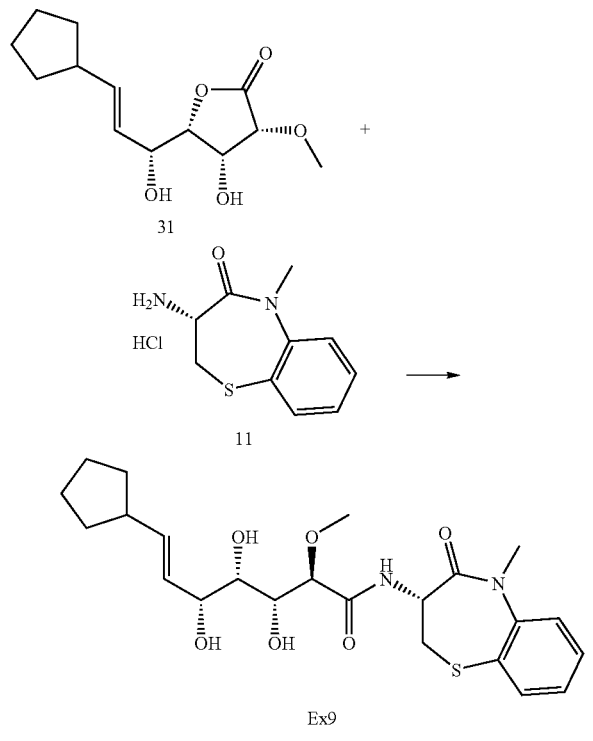

60 mg (234 μmol) of 31, 68.7 mg (281 μmol) of 11 and 58.3 mg (351 μmol) of sodium 2-ethylhexanoate in 2.5 mL of THF are placed in a 30 mL one-necked flask. The solution is stirred at room temperature for one week. The solution is then taken up in 5 mL of $CH_2Cl_2$ and washed with 4 mL of 0.5 N HCl and then 4 mL of water. The aqueous phase is then extracted with 2×5 mL of $CH_2Cl_2$ and the organic phases are combined, dried over sodium sulfate and then filtered. The solvent is then evaporated to dryness under reduced pressure and the residue is purified on a Biotage 12-M silica column (eluent: 97/3 $CH_2Cl_2$/isopropanol). The product Example 9 (91.7 mg, Rf=0.25 under the elution conditions used) is obtained in the form of a white solid.

MS: m/z=929 $[2M+H]^+$, 465 $[M+H]^+$, 447 $[(M-H_2O)+H]^+$, 429 $[(M-2H_2O)+H]^+$ $^1$H NMR (400 MHz, DMSO-$d_6$): δ (ppm)=8.24 (d, 1H, J=8 Hz), 7.67 (d, 1H, J=8 Hz), 7.57 (m, 2H), 7.33 (m, 1H), 5.57 (dd, 1H, J=6.5 Hz and 15 Hz), 5.34 (dd, 1H, J=6.5 Hz and 15 Hz), 4.53 (d, 1H, J=4.5 Hz), 4.41 (m, 1H), 4.33 (d, 1H, J=4.5 Hz), 4.30 (d, 1H, J=5 Hz), 3.91 (m, 1H), 3.66 (d, 1H, J=8 Hz), 3.47 (m, 1H), 3.41 (m, 1H), 3.31 (m, 1H), 3.29 (s, 3H), 3.20 (s, 3H), 3.07 (t, 1H, J=12 Hz), 2.38 (m, 1H), 1.70 (m, 2H), 1.54 (m, 4H), 1.22 (m, 2H).

EXAMPLE 10

(2R,3R,4S,5R,6E)-3,4,5-trihydroxy-2-methoxy-N-[(3R)-5-methyl-4-oxo-2,3,4,5-tetrahydro-1,5-benzothiazepin-3-yl]undec-6-enamide

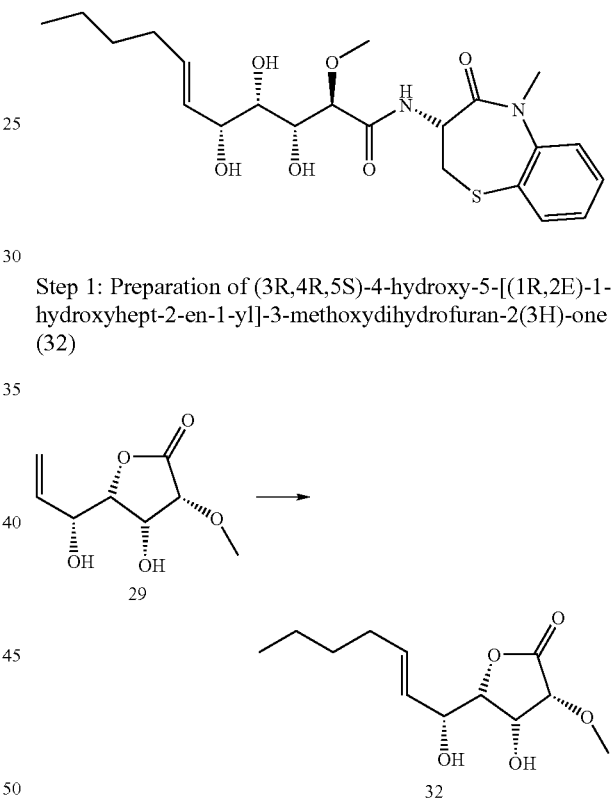

Step 1: Preparation of (3R,4R,5S)-4-hydroxy-5-[(1R,2E)-1-hydroxyhept-2-en-1-yl]-3-methoxydihydrofuran-2(3H)-one (32)

100 mg (0.53 mmol) of 29, 4 mL of $CH_2Cl_2$, 665 μL (5.3 mmol) of 1-hexene and then 90.2 mg (106 μmol) of Grubbs second-generation catalyst are placed in a 5 mL vial. The solution is heated for 10 minutes at 60° C. by microwave. The solvent is then evaporated to dryness under reduced pressure and the residue is purified on a Biotage 12-S silica column (eluent: 40/60 heptane/EtOAc). The product 32 (57.3 mg, Rf=0.29 under the elution conditions used) is obtained in the form of a beige-coloured solid.

$^1$H NMR (300 MHz, DMSO-$d_6$): δ (ppm)=5.81 (m, 1H), 5.51 (dd, 1H, J=5 Hz and 15.5 Hz), 5.38 (d, 1H, J=4.2 Hz), 5.14 (d, 1H, J=4.9 Hz), 4.26 (m, 3H), 3.96 (dd, 1H, J=2.2 Hz and 8.8 Hz), 3.41 (s, 3H), 2.03 (q, 2H, J=6 Hz), 1.32 (m, 4H), 0.87 (t, 3H, J=8 Hz)

Step 2: Preparation of (2R,3R,4S,5R,6E)-3,4,5-trihydroxy-2-methoxy-N-[(3R)-5-methyl-4-oxo-2,3,4,5-tetrahydro-1,5-benzothiazepin-3-yl]undec-6-enamide (Example 10)

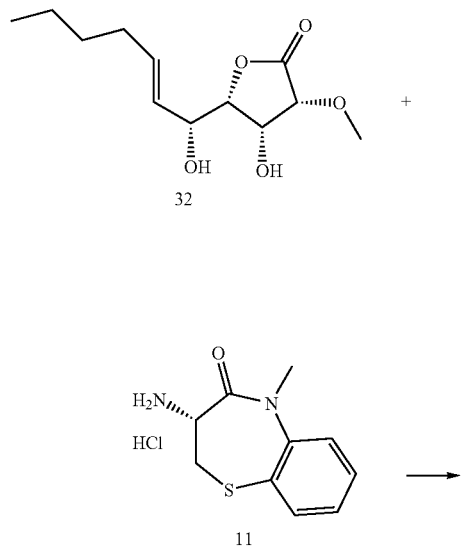

60 mg (246 µmol) of 32, 72.1 mg (294 µmol) of 11 and 61.2 mg (368 µmol) of sodium 2-ethylhexanoate in 2.5 mL of THF are placed in a 20 mL one-necked flask. The solution is stirred at room temperature for 48 hours. The solution is then taken up in 5 mL of CH$_2$Cl$_2$ and washed with 4 mL of 0.5 N HCl and then 3 mL of water. The aqueous phase is then extracted with 2×5 mL of CH$_2$Cl$_2$ and the organic phases are combined, dried over sodium sulfate and then filtered. The solvent is then evaporated to dryness under reduced pressure and the residue is then purified on a Biotage 12-M silica column (eluent: 98/2 CH$_2$Cl$_2$/isopropanol). The product Example 10 (30.2 mg, Rf=0.19 under the elution conditions used) is obtained in the form of a white solid.

MS: m/z (ES$^+$)=926 [2M+Na]$^+$, 474 [M+Na]$^+$, 453 [M+H]$^+$, 435 [(M–H$_2$O)+H]$^+$ $^1$H NMR (400 MHz, DMSO-d$_6$): δ (ppm)=8.24 (d, 1H, J=8 Hz), 7.66 (d, 1H, J=8 Hz), 7.56 (m, 2H), 7.33 (m, 1H), 5.55 (m, 1H), 5.36 (dd, 1H, J=7.5 Hz and 16 Hz), 4.52 (d, 1H, J=4 Hz), 4.40 (m, 1H), 4.31 (d, 1H, J=4.5 Hz), 4.28 (d, 1H, J=5 Hz), 3.91 (m, 1H), 3.65 (d, 1H, J=8 Hz), 3.48 (m, 1H), 3.43 (m, 1H), 3.34 (m, 1H), 3.32 (s, 3H), 3.19 (s, 3H), 3.06 (t, 1H, J=12 Hz), 1.95 (m, 2H), 1.26 (m, 4H), 0.86 (t, 3H, J=7.5 Hz)

EXAMPLE 11

(2R,3R,4S,5R,6E)-7-cyclohexyl-3,4,5-trihydroxy-2-methoxy-N-[(3R)-5-methyl-4-oxo-2,3,4,5-tetrahydro-1,5-benzothiazepin-3-yl]hept-6-enamide

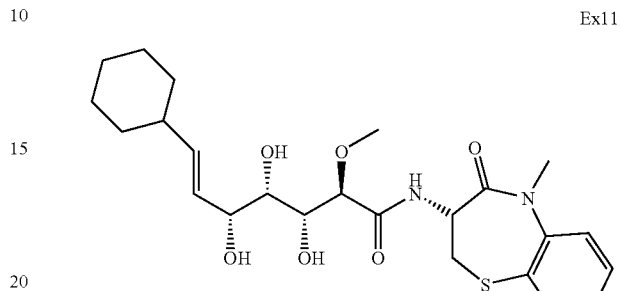

Step 1: Preparation of (3R,4R,5S)-5-[(1R,2E)-3-cyclohexyl-1-hydroxyprop-2-en-1-yl]-4-hydroxy-3-methoxydihydrofuran-2(3H)-one (33)

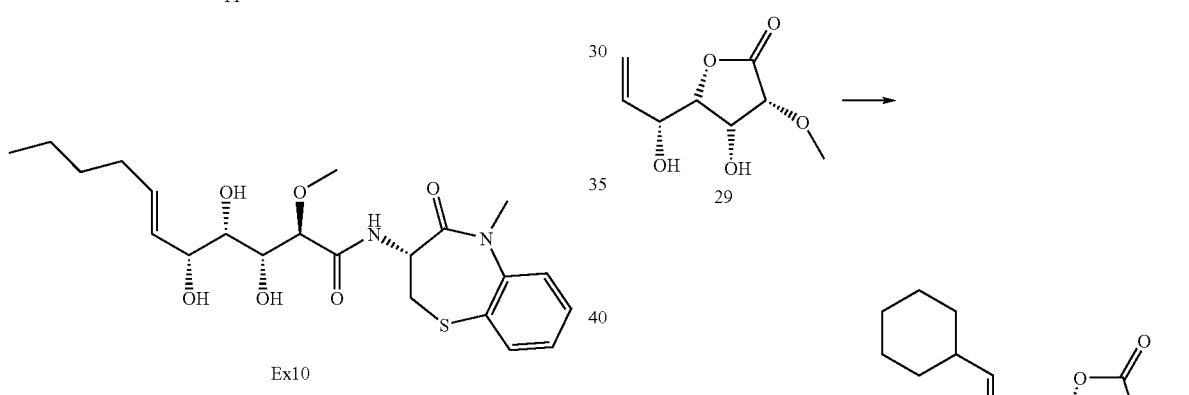

100 mg (0.53 mmol) of 29, 4 mL of CH$_2$Cl$_2$, 728 µL (5.3 mmol) of vinylcyclohexane and then 90.2 mg (106 µmol) of Grubbs second-generation catalyst are placed in a 5 mL vial. The solution is heated for 10 minutes at 60° C. by microwave. The solvent is then evaporated to dryness under reduced pressure and the residue is purified on a Biotage 25-M silica column (eluent: 45/55 heptane/EtOAc). The product 33 (130.4 mg, Rf=0.33 under the elution conditions used) is obtained in the form of a beige-coloured solid.

MS: m/z (ES$^+$)=293 [M+Na]$^+$ (ES$^-$)=315 [(M+HCOOH)—H]$^-$, 269 [M–H]$^-$ $^1$H NMR (300 MHz, DMSO-d$_6$): δ (ppm)=5.8 (dd, 1H, J=6 Hz and 16 Hz), 5.48 (dd, 1H, J=4.5 Hz and 16 Hz), 5.16 (br s, 2H), 4.29 (m, 2H), 4.25 (d, 1H, J=4.5 Hz), 3.95 (dd, 1H, J=3 Hz and 9 Hz), 3.42 (s, 3H), 1.96 (m, 1H), 1.66 (m, 4H), 1.15 (m, 6H)

Step 2: Preparation of (2R,3R,4S,5R,6E)-7-cyclohexyl-3,4,5-trihydroxy-2-methoxy-N -[(3R)-5-methyl-4-oxo-2,3,4,5-tetrahydro-1,5-benzothiazepin-3-yl]hept-6-enamide (Example 11)

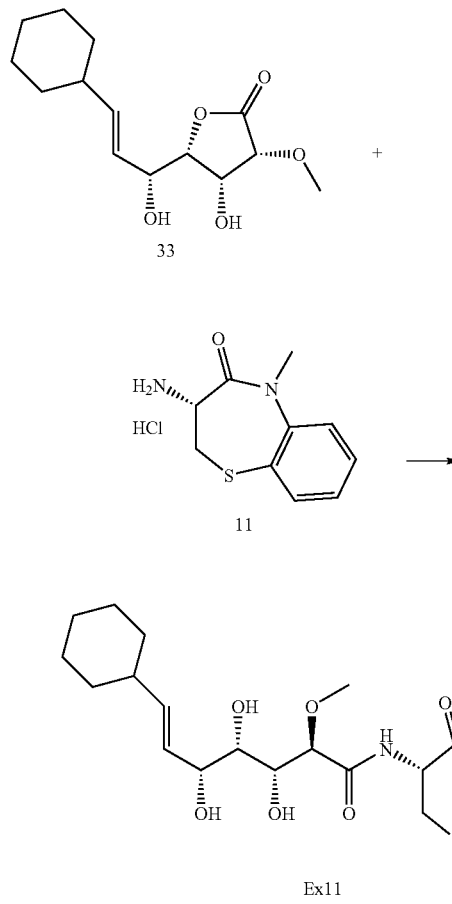

120 mg (444 μmol) of 33, 130.4 mg (533 μmol) of 11 and 177 mg (1.065 mmol) of sodium 2-ethylhexanoate in 6 mL of THF are placed in a 20 mL one-necked flask. The solution is stirred at room temperature for one week. The solution is then taken up in 6 mL of CH₂Cl₂ and washed with 2×5 mL of 0.5 N HCl and then 5 mL of water. The aqueous phase is then extracted with 2×5 mL of CH₂Cl₂ and the organic phases are combined, dried over sodium sulfate and then filtered. The solvent is then evaporated to dryness under reduced pressure and the residue is purified on a Biotage 12-S silica column (eluent: 15/85 heptane/EtOAc). The product Example 11 (91.1 mg, Rf=0.24 under the elution conditions used) is obtained in the form of a white solid.

MS: m/z (ES⁺)=979 [2M+Na]⁺, 501 [M+Na]⁺, 479 [M+H]⁺, 461 [(M−H₂O)+H]⁺

¹H NMR (400 MHz, DMSO-d₆): δ (ppm)=8.28 (d, 1H, J=8 Hz), 7.70 (d, 1H, J=8 Hz), 7.60 (m, 2H), 7.37 (m, 1H), 5.57 (dd, 1H, J=6.5 Hz and 15 Hz), 5.35 (dd, 1H, J=6.5 Hz and 15 Hz), 4.58 (br s, 1H), 4.44 (m, 1H), 4.35 (br s, 2H), 3.93 (t, 1H, J=6.5 Hz), 3.69 (d, 1H, J=8 Hz), 3.50 (m, 1H), 3.44 (m, 1H), 3.40 (m, 1H), 3.36 (s, 3H), 3.23 (s, 3H), 3.10 (t, 1H, J=12 Hz), 1.92 (m, 1H), 1.65 (m, 4H), 1.15 (m, 6H)

EXAMPLE 12

(2R,3R,4S,5R,6E)-7-(2-fluorophenyl)-3,4,5-trihydroxy-2-methoxy-N -[(3R)-5-methyl-4-oxo-2,3,4,5-tetrahydro-1,5-benzothiazepin-3-yl]hept-6-enamide

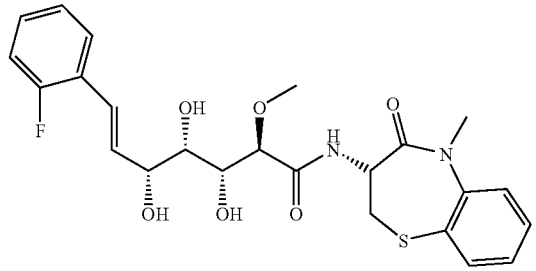

Step 1: Preparation of (3R,4R,5S)-5-[(1R,2E)-3-(2-fluorophenyl)-1-hydroxyprop-2-en -1-yl]-4-hydroxy-3-methoxydihydrofuran-2(3H)-one (34)

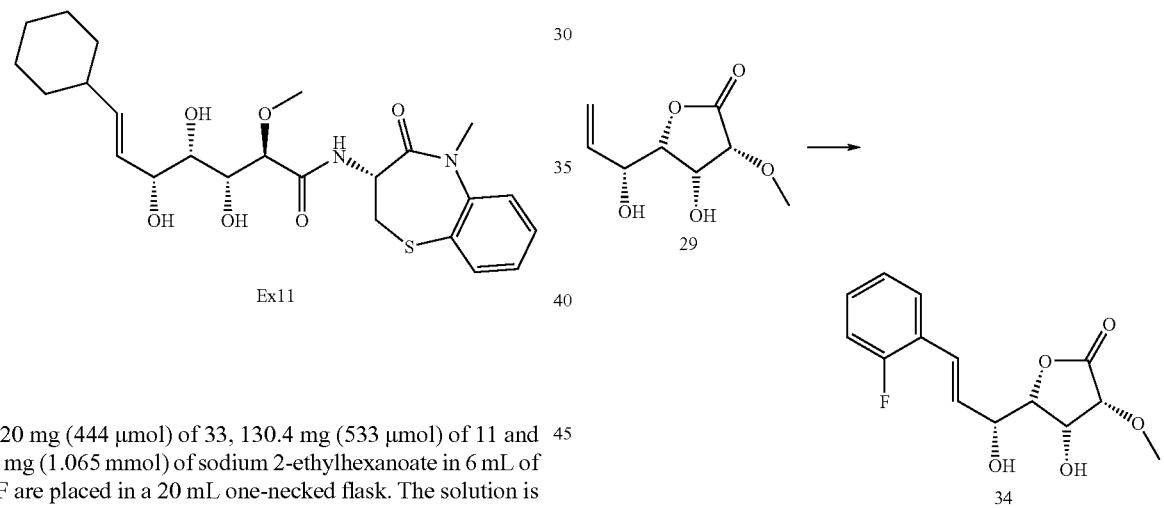

100 mg (0.53 mmol) of 29, 4 mL of CH₂Cl₂, 633 μL (5.3 mmol) of 2-fluorostyrene and then 90.2 mg (106 μmol) of Grubbs second-generation catalyst are placed in a 5 mL vial. The solution is heated for 10 minutes at 60° C. by microwave. The solvent is then evaporated to dryness under reduced pressure and the residue is purified on a Biotage 25-M silica column (eluent: 40/60 heptane/EtOAc). The product 34 (64.4 mg, Rf=0.24 under the elution conditions used) is obtained in the form of a white solid.

MS: m/z (ES⁺)=265 [(M−H₂O)+H]⁺

(ES⁻)=327 [(M+HCOOH)−H]⁻, 281 [M−H]⁻

¹H NMR (300 MHz, DMSO-d₆): δ (ppm)=7.61 (t, 1H, J=9 Hz), 7.31 (m, 1H), 7.19 (t, 2H, J=9 Hz), 6.89 (d, 1H, J=16.1 Hz), 6.50 (dd, 1H, J=4.9 Hz and 16.1 Hz), 5.55 (d, 2H, J=5.5 Hz), 4.49 (m, 1H), 4.42 (m, 1H), 4.28 (d, 1H, J=4.3 Hz), 4.09 (dd, 1H, J=2.8 Hz and 8.3 Hz), 3.43 (s, 3H)

Step 2: Preparation of (2R,3R,4S,5R,6E)-7-(2-fluorophenyl)-3,4,5-trihydroxy-2-methoxy-N-[(3R)-5-methyl-4-oxo-2,3,4,5-tetrahydro-1,5-benzothiazepin-3-yl]hept-6-enamide (Example 12)

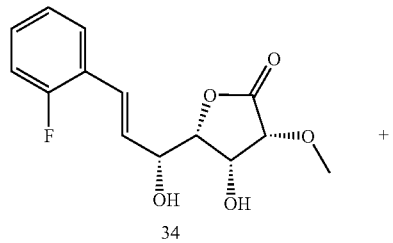
34

+

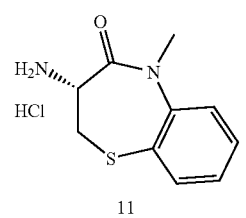
11

→

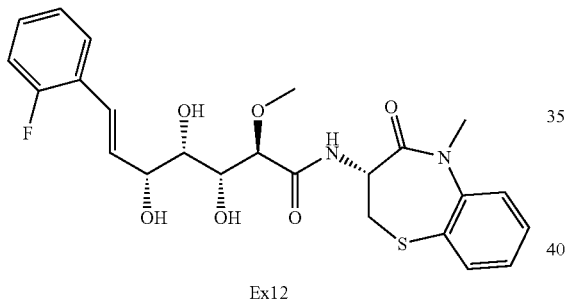
Ex12

60 mg (212 μmol) of 34, 62.4 mg (255 μmol) of 11 and 53 mg (319 μmol) of sodium 2-ethylhexanoate in 2.5 mL of THF are placed in a 30 mL one-necked flask. The solution is stirred at room temperature for 6 days. The solution is then taken up in 5 mL of $CH_2Cl_2$ and then washed with 4 mL of 0.5 N HCl and then 4 mL of water. The aqueous phase is then extracted with 2×5 mL of $CH_2Cl_2$ and the organic phases are combined, dried over sodium sulfate and then filtered. The solvent is then evaporated to dryness under reduced pressure and the residue is purified on a Biotage 12-M silica column (eluent: 98/2 $CH_2Cl_2$/isopropanol). The product Example 12 (45.7 mg, Rf=0.37 under the elution conditions used) is obtained in the form of a white solid.

MS: m/z $(ES^+)$=491 $[M+H]^+$, 473 $[(M-H_2O)+H]^+$
$(ES^-)$=535 $[(M+HCOOH)-H]^-$, 489 $[M-H]^-$ $^1$H NMR (400 MHz, DMSO-$d_6$): δ (ppm)=8.27 (d, 1H, J=8 Hz), 7.65 (d, 1H, J=8 Hz), 7.54 (m, 3H), 7.32 (m, 1H), 7.26 (m, 1H), 7.16 (m, 2H), 6.65 (d, 1H, J=16 Hz), 6.38 (dd, 1H, J=6 Hz and 16 Hz), 4.95 (d, 1H, J=4 Hz), 4.55 (d, 1H, J=6 Hz), 4.47 (d, 1H, J=6.5 Hz), 4.41 (m, 1H), 4.18 (m, 1H), 3.70 (d, 1H, J=8 Hz), 3.53 (m, 1H), 3.44 (m, 1H), 3.42 (m, 1H), 3.28 (s, 3H), 3.20 (s, 3H), 3.07 (t, 1H, J=12 Hz)

EXAMPLE 13

(2R,3R,4S,5R,6E)-7-(4-fluorophenyl)-3,4,5-trihydroxy-2-methoxy-N -[(3R)-5-methyl-4-oxo-2,3,4,5-tetrahydro-1,5-benzothiazepin-3-yl]hept-6-enamide

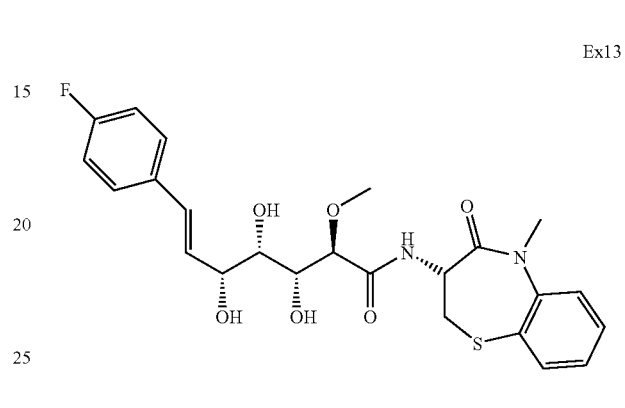
Ex13

Step 1: Preparation of (3R,4R,5S)-5-[(1R,2E)-3-(4-fluorophenyl)-1-hydroxyprop-2-en -1-yl]-4-hydroxy-3-methoxydihydrofuran-2(3H)-one (35)

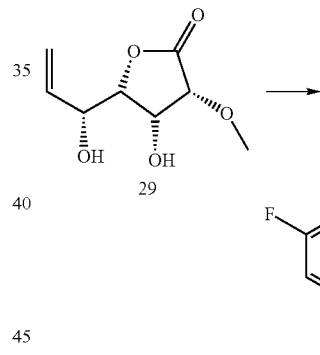
29

→

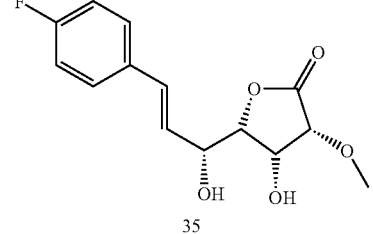
35

100 mg (0.53 mmol) of 29, 4 mL of $CH_2Cl_2$, 636 μL (5.3 mmol) of 4-fluorostyrene and then 90.2 mg (106 μmol) of Grubbs second-generation catalyst are placed in a 5 mL vial. The solution is heated for 10 minutes at 60° C. by microwave. The solvent is then evaporated to dryness under reduced pressure and the residue is purified on a Biotage 25-M silica column (eluent: 9/1 $CH_2Cl_2$/isopropanol). The product 35 (99.2 mg, Rf=0.15 under the elution conditions used) is obtained in the form of a white solid.

MS: m/z (%)=282 $[MH^+]$, 152 (100)

$^1$H NMR (300 MHz, DMSO-$d_6$): δ (ppm)=7.5 (dd, 2H, J=6 Hz and 9 Hz), 7.17 (t, 2H, J=9 Hz), 6.76 (d, 1H, J=16 Hz), 6.33 (dd, 1H, J=6 Hz and 15 Hz), 5.52 (br s, 1H), 5.46 (d, 1H, J=5.5 Hz), 4.46 (m, 1H), 4.42 (m, 1H), 4.28 (d, 1H, J=4.5 Hz), 4.08 (dd, 1H, J=3 Hz and 9 Hz), 3.42 (s, 3H)

Step 2: Preparation of (2R,3R,4S,5R,6E)-7-(4-fluorophenyl)-3,4,5-trihydroxy-2-methoxy-N-[(3R)-5-methyl-4-oxo-2,3,4,5-tetrahydro-1,5-benzothiazepin-3-yl]hept-6-enamide (Example 13)

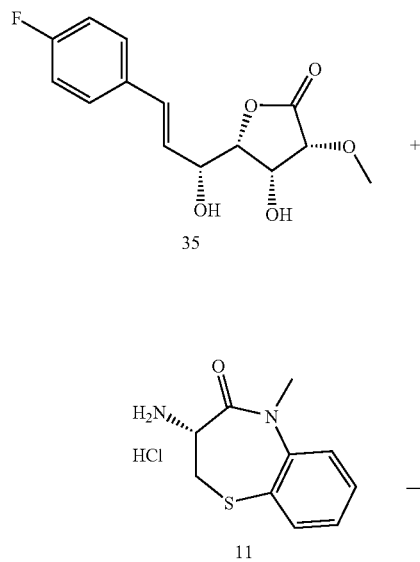

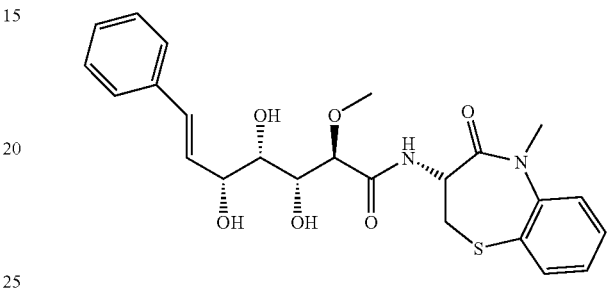

90 mg (319 µmol) of 35, 93.6 mg (383 µmol) of 11 and 127.2 mg (765 µmol) of sodium 2-ethylhexanoate in 4 mL of THF are placed in a 30 mL one-necked flask. The solution is stirred at room temperature for 28 hours. The solution is then taken up in 6 mL of CH$_2$Cl$_2$ and washed with 5 mL of 0.5 N HCl and then with 5 mL of water. The aqueous phase is then extracted with 2×5 mL of CH$_2$Cl$_2$ and the organic phases are combined, dried over sodium sulfate and then filtered. The solvent is then evaporated to dryness under reduced pressure and the residue is then purified on a Biotage 12-M silica column (eluent: 15/85 heptane/EtOAc). The product Example 13 (55.5 mg, Rf=0.17 under the elution conditions used) is obtained in the form of a white solid.

MS: m/z (ES$^+$)=513 [M+Na]$^+$, 491 [M+H]$^+$ (ES$^-$)=535 [(M+HCOOH)–H]$^-$, 489 [M–H]$^-$ $^1$H NMR (300 MHz, DMSO-d$_6$): δ (ppm)=8.26 (d, 1H, J=8 Hz), 7.65 (d, 1H, J=8 Hz), 7.56 (m, 2H), 7.43 (dd, 2H, J=6 Hz and 9 Hz), 7.32 (m, 1H), 7.13 (t, 2H, J=9 Hz), 6.52 (d, 1H, J=16 Hz), 6.20 (dd, 1H, J=6 Hz and 16 Hz), 4.86 (d, 1H, J=4 Hz), 4.49 (d, 1H, J=6 Hz), 4.44 (d, 1H, J=6.5 Hz), 4.40 (m, 1H), 4.15 (m, 1H), 3.70 (d, 1H, J=8 Hz), 3.53 (m, 1H), 3.47 (m, 1H), 3.45 (m, 1H), 3.28 (s, 3H), 3.19 (s, 3H), 3.07 (t, 1H, J=12 Hz)

EXAMPLE 14

(2R,3R,4S,5R,6E)-3,4,5-trihydroxy-2-methoxy-N-[(3R)-5-methyl-4-oxo-2,3,4,5-tetrahydro-1,5-benzothiazepin-3-yl]-7-phenylhept-6-enamide

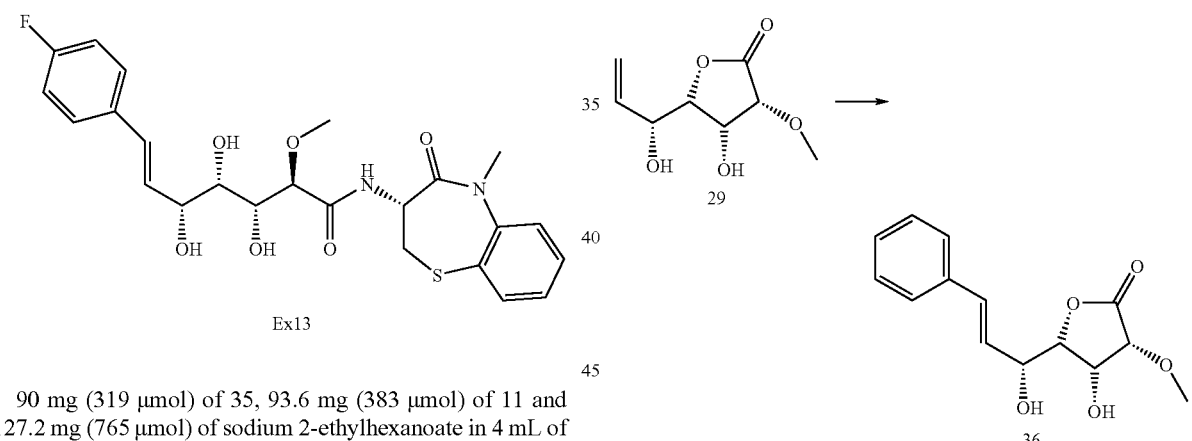

Step 1: Preparation of (3R,4R,5S)-4-hydroxy-5-[(1R,2E)-1-hydroxy-3-phenylprop-2-en-1-yl]-3-methoxydihydrofuran-2(3H)-one) (36)

100 mg (0.53 mmol) 29, 4 mL of CH$_2$Cl$_2$, 615 µL (5.3 mmol) of styrene and then 90.2 mg (106 µmol) of Grubbs second-generation catalyst are placed in a 5 mL vial. The solution is heated for 10 minutes at 60° C. by microwave. The solvent is then evaporated to dryness under reduced pressure and the residue is then purified on a Biotage 25-M silica column (eluent: 98/2 CH$_2$Cl$_2$/isopropanol). The product 36 (79.6 mg, Rf=0.24 under the elution conditions used) is obtained in the form of a brown solid.

MS: m/z (ES$^-$)=527 [2M–H]$^-$, 309 [(M+HCOOH)–H]$^-$, 263 [M–H]$^-$ $^1$H NMR (300 MHz, DMSO-d$_6$): δ (ppm)=7.45 (d, 2H, J=7.5 Hz), 7.35 (t, 2H, J=7.5 Hz), 7.25 (t, 1H, J=7.5 Hz), 6.77 (d, 1H, J=16 Hz), 5.88 (d, 1H, J=5.5 Hz and 16 Hz), 5.54 (d, 1H, J=3 Hz), 5.46 (d, 1H, J=5 Hz), 4.48 (m, 1H), 4.42 (m, 1H), 4.48 (d, 1H, J=4 Hz), 4.09 (dd, 1H, J=3 Hz and 9 Hz), 3.41 (s, 3H)

Step 2: Preparation of (2R,3R,4S,5R,6E)-3,4,5-trihydroxy-2-methoxy-N-[(3R)-5-methyl-4-oxo-2,3,4,5-tetrahydro-1,5-benzothiazepin-3-yl]-7-phenylhept-6-enamide (Example 14)

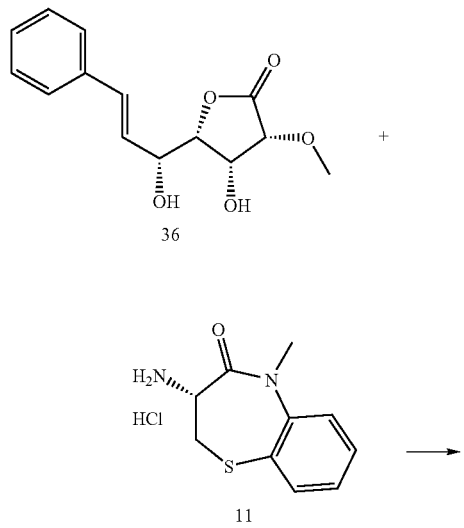

70 mg (265 µmol) of 36, 77.8 mg (318 µmol) of 11 and 106 mg (636 µmol) of sodium 2-ethylhexanoate in 4 mL of THF are placed in a 20 mL one-necked flask. The solution is stirred at room temperature for 43 hours. The solution is then taken up in 6 mL of CH$_2$Cl$_2$ and washed with 2×5 mL of 0.5 N HCl and then 5 mL of water. The aqueous phase is then extracted with 2×5 mL of CH$_2$Cl$_2$ and the organic phases are combined, dried over sodium sulfate and then filtered. The solvent is then evaporated to dryness under reduced pressure and the residue is purified on a Biotage 12-S silica column (eluent: 15/85 heptane/EtOAc). The product Example 14 (62.4 mg, Rf=0.3 under the elution conditions used) is obtained in the form of a white solid.

MS: m/z (ES$^+$)=495 [M+Na]$^+$, 473 [M+H]$^+$ (ES$^+$)=517 [(M+HCOOH)−H]$^−$, 471 [M−H]$^−$ $^1$H NMR (300 MHz, DMSO-d$_6$): δ (ppm)=8.26 (d, 1H, J=8 Hz), 7.65 (d, 1H, J=8 Hz), 7.55 (m, 2H), 7.39 (d, 2H, J=6.5 Hz), 7.33 (m, 2H), 7.29 (m, 1H), 7.21 (t, 1H), 6.53 (d, 1H, J=16 Hz), 6.25 (dd, 1H, J=6 Hz and 16 Hz), 5.34 (d, 1H, J=4.5 Hz), 4.48 (d, 1H, J=6 Hz), 4.44 (d, 1H, J=6.5 Hz), 4.38 (m, 1H), 4.15 (m, 1H), 3.70 (d, 1H, J=7.5 Hz), 3.53 (m, 1H), 3.46 (m, 1H), 3.42 (m, 1H), 3.32 (s, 3H), 3.20 (s, 3H), 3.06 (t, 1H, J=12 Hz)

EXAMPLE 15

(2R,3R,4S,5R,6E)-3,4,5-trihydroxy-2-methoxy-8,8-dimethyl-N-[(3R)-4-oxo-9-phenyl-2,3,4,5-tetrahydro-1,5-benzothiazepin-3-yl]non-6-enamide

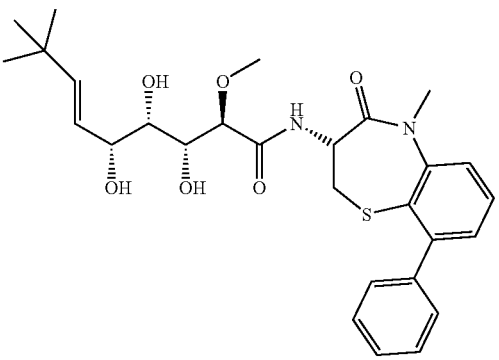

Step 1: Preparation of 2-fluoro-3-nitrobiphenyl (37)

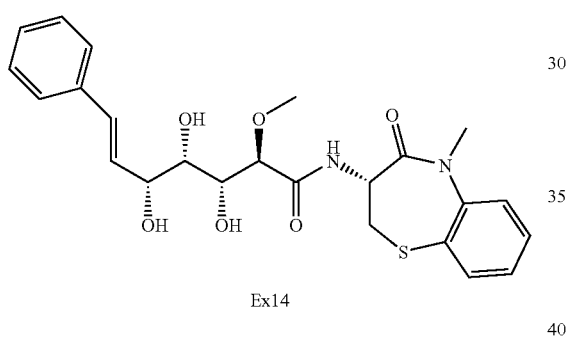

277 mg of phenylboronic acid (2.273 mmol), 46.41 mg of 1,1'-bis(diphenyl-phosphino)ferrocenepalladium chloride (C$_{35}$H$_{30}$Cl$_4$FeP$_2$Pd, MW 816.65, 0.057 mmol) and 2.96 g of caesium carbonate (9.09 mmol) are placed in a 50 mL round-bottomed flask, with stirring and under an argon atmosphere, containing 10 mL of water, 3 mL of dioxane and 500 mg of 17 (2.273 mmol). The medium is heated at 100° C. with stirring for 3 hours. 20 mL of EtOAc are then added and the mixture is washed with twice 20 mL of water. The organic phase is dried over MgSO$_4$, filtered and evaporated to dryness. The crude product is chromatographed on a silica cartridge (30 g) eluting with heptane/EtOAc (as an EtOAc gradient: 10% to 50%). 360 mg of expected product 37 are collected (yellow oil).

EI: 217$^+$ $^1$H NMR (400 MHz, DMSO-d$_6$), δ (ppm): from 7.45 to 7.63 (m, 6H); 7.91 (dt, J=2.0 and 9.0 Hz, 1H); 8.14 (dt, J=2.0 and 9.0 Hz, 1H).

Step 2: Preparation of N-[(2,2-dimethylpropanoyl)oxy]-S-(3-nitrobiphenyl-2-yl)-L-cysteine (38)

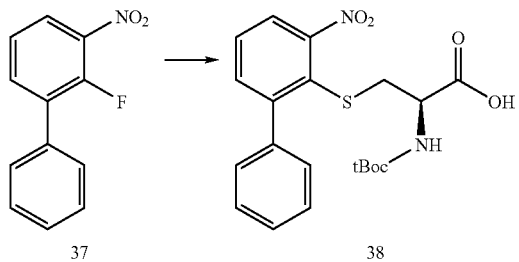

A solution of 37 (360 mg, 1.657 mmol) in 2.8 mL of ethanol is introduced dropwise into a 25 mL three-necked flask containing 367 mg of L-Boc-Cys-OH (1.657 mmol), 2.5 mL of water and 402 mg of NaHCO$_3$ (4.789 mmol). The medium is refluxed for 6 hours, the ethanol is then evaporated off and 5 mL of distilled water are added. The aqueous phase is then washed twice with 5 mL of ether, and once the ether phase has been separated out by settling, the aqueous phase is brought to pH 2-3 with HCl (1N) and extracted twice with 5 mL of EtOAc. The organic phases are combined, dried over MgSO$_4$, filtered and finally evaporated to dryness. 0.81 g of crude product 38 is obtained, which product is used directly in the following step.

$^1$H NMR (400 MHz, DMSO-d$_6$), δ (ppm): 1.32 (s, 9H); from 2.39 to 2.57 (partially masked m, 2H); 3.57 (m, 1H); 6.77 (d, J=8.0 Hz, 1H); from 7.40 to 7.55 (m, 5H); 7.59 (broad d, J=8.0 Hz, 1H); 7.65 (t, J=8.0 Hz, 1H); 7.86 (broad d, J=8.0 Hz, 1H); 12.15 (broad m, 1H).

Step 3: Preparation of S-(3-aminobiphenyl-2-yl)-N-[(2,2-dimethylpropanoyl)oxy]-L-cysteine (39)

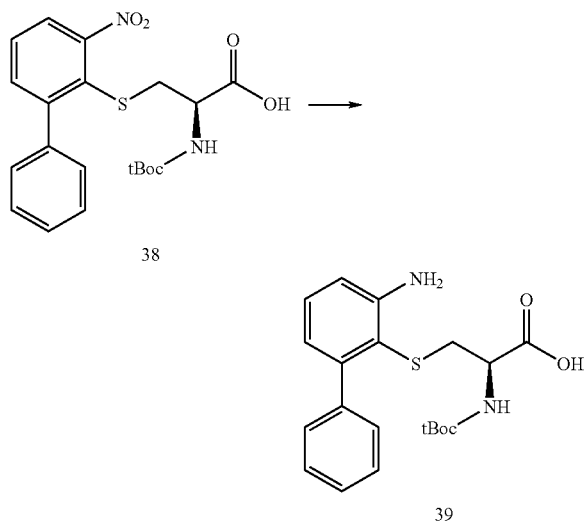

810 mg of 38 (1.936 mmol), 69.84 mg of Pd/C (10%) and 20 mL of MeOH are hydrogenated at 5 bar for 10 hours at 20° C. in an autoclave. After filtering off the catalyst through Celite, the solvent is evaporated off and 580 mg of expected product 39 are obtained, which product is used directly in the following step.

$^1$H NMR (400 MHz, DMSO-d$_6$), δ (ppm): 1.33 (s, 9H); from 2.60 to 2.75 (m, 2H); 3.81 (m, 1H); 5.60 (very broad m, 2H); 6.47 (d, J=8.0 Hz, 1H); 6.78 (d, J=8.0 Hz, 1H); 6.89 (d, J=8.0 Hz, 1H); 7.09 (t, J=8.0 Hz, 1H); from 7.24 to 7.41 (m, 5H); 12.2 (very broad m, 1H).

Step 4: Preparation of (3R)-3-{[(2,2-dimethylpropanoyl)oxy]amino}-9-phenyl-2,3-dihydro-1,5-benzothiazepin-4(5H)-one (40)

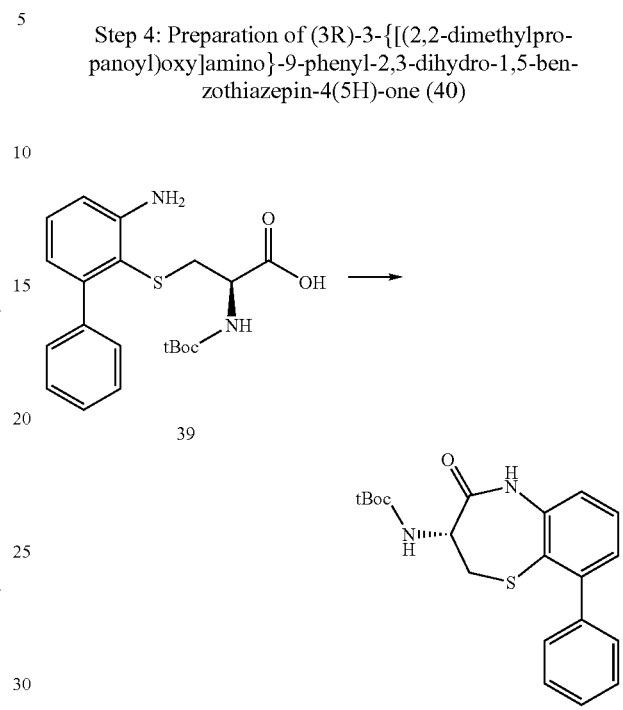

0.269 mL of diethyl cyanophosphonate (289.4 mg, 1.774 mmol) are placed in a 25 mL three-necked flask containing 580 mg of 39 (1.493 mmol) and 7 mL of DMF, at 0° C., followed, 10 minutes later, by addition of 0.201 mL of TEA (1.43 mmol). The reaction medium is stirred at 0° C. for 2 hours. 20 mL of EtOAc are added and the mixture is then washed with twice 20 mL of distilled water. The organic phase is dried over MgSO$_4$, filtered and then evaporated to dryness. The crude product (600 mg of yellow oil) is chromatographed on a silica cartridge (30 g) with a heptane/EtOAc eluent (as an EtOAc gradient: 10% to 50%). 410 mg of expected product 40 are obtained (white solid).

$^1$H NMR (400 MHz, DMSO-d$_6$), δ (ppm): 1.35 (s, 9H); 3.02 (t, J=12.0 Hz, 1H); 3.45 (dd, J=7.5 and 12.0 Hz, 1H); 4.20 (m, 1H); from 7.12 to 7.25 (m, 3H); from 7.33 to 7.51 (m, 6H); 10.05 (s, 1H).

Step 4: Preparation of (3R)-3-amino-9-phenyl-2,3-dihydro-1,5-benzothiazepin-4(5H)-one hydrochloride (41)

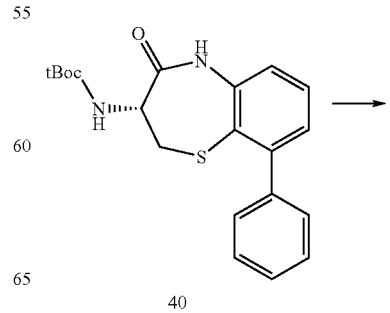

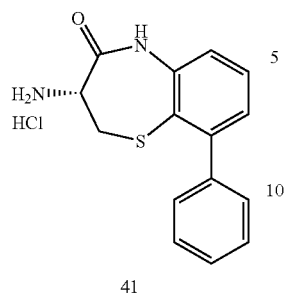

41

8 mL of a solution of hydrogen chloride in dioxane (4 M) are placed in a 50 mL round-bottomed flask containing 410 mg of 40 (1.107 mmol). The mixture is stirred for 4 hours at room temperature under argon. A white precipitate forms, which is filtered off by suction and washed with 3 mL of dioxane and then 5 mL of isopropyl ether. 260 mg of amine 41 (white solid) are thus obtained in the form of the hydrochloride.

$^1$H NMR (300 MHz, DMSO-$d_6$), δ (ppm): 3.17 (t, J=12.0 Hz, 1H); 3.65 (dd, J=8.0 and 12.0 Hz, 1H); 4.08 (dd, J=8.0 and 12.0 Hz, 1H); 7.21 (dd, J=1.5 and 8.0 Hz, 1H); 7.28 (dd, J=1.5 and 8.0 Hz, 1H); from 7.35 to 7.49 (m, 5H); 7.52 (t, J=8.0 Hz, 1H); 8.39 (broad s, 3H); 10.65 (s, 1H).

Step 5: Preparation of (2R,3R,4S,5R,6E)-3,4,5-trihydroxy-2-methoxy-8,8-dimethyl-N-[(3R)-4-oxo-9-phenyl-2,3,4,5-tetrahydro-1,5-benzothiazepin-3-yl]non-6-enamide (Example 15)

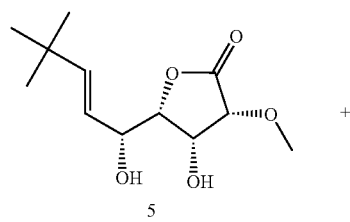

5

+

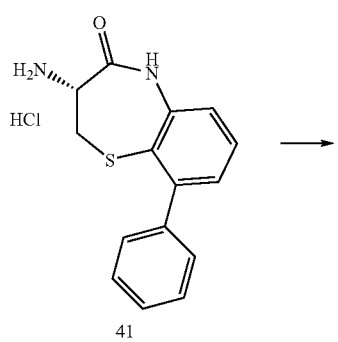

41

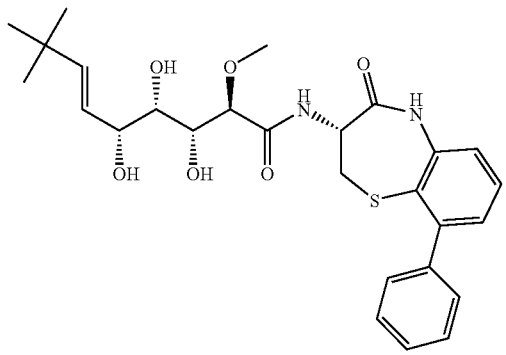

Ex15

100 mg of 5 (409 μmol), 151 mg of 41 (491 μmol) and 102 mg of sodium 2-ethylhexanoate (0.61 mmol) in 2.3 mL of THF are successively introduced into a 25 mL round-bottomed flask, with stirring and under an argon atmosphere. Stirring is continued at room temperature for 24 hours. The reaction medium is concentrated to dryness. The residues are chromatographed on a silica cartridge (15 g, CH$_2$Cl$_2$/MeOH eluent as a gradient: 1% to 10% MeOH). 145 mg of expected product Example 15 are collected.

ES: m/z=513 (M−H$^+$)

$^1$H NMR (400 MHz, DMSO-$d_6$), δ (ppm): 0.96 (s, 9H); 3.10 (t, J=12.0 Hz, 1H); 3.22 (s, 3H); 3.30 (masked m, 1H); from 3.40 to 3.55 (m, 2H); 3.69 (d, J=8.0 Hz, 1H); 3.94 (m, 1H); 4.29 (m, 2H); 4.54 (m, 2H); 5.30 (dd, J=7.0 and 16.0 Hz, 1H); 5.63 (d, J=16.0 Hz, 1H); 7.19 (broad d, J=7.5 Hz, 1H); 7.23 (broad d, J=7.5 Hz, 1H); from 7.35 to 7.46 (m, 5H); 7.49 (t, J=7.5 Hz, 1H); 8.25 (d, J=8.0 Hz, 1H); 10.2 (s, 1H)

EXAMPLE 16

(2R,3R,4S,5R,6E)-N-[(3R)-9-(3-cyanophenyl)-4-oxo-2,3,4,5-tetrahydro-1,5-benzothiazepin-3-yl]-3,4,5-trihydroxy-2-methoxy-8,8-dimethylnon-6-enamide

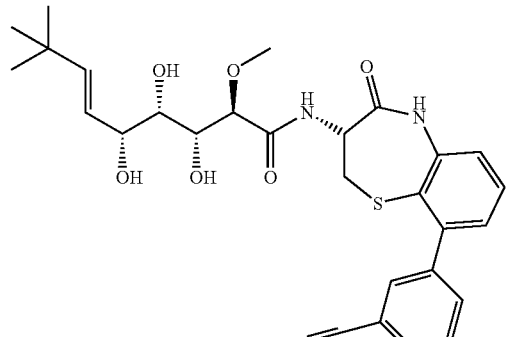

Ex 16

Step 1: Preparation of 2'-fluoro-3'-nitrobiphenyl-3-carbonitrile (42)

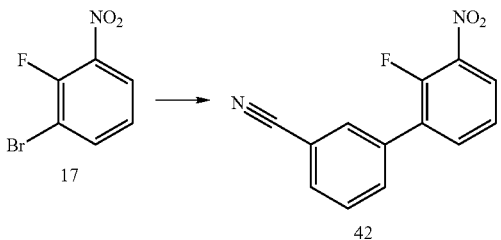

334 mg of 3-cyanophenylboronic acid (2.273 mmol), 46.41 mg of 1,1'-bis(diphenylphosphino)ferrocenepalladium chloride (C$_{35}$H$_{30}$Cl$_4$FeP$_2$Pd, MW 816.65, 0.057 mmol) and 2.96 g of caesium carbonate (9.09 mmol) are placed in a 50 mL round-bottomed flask, with stirring and under an argon atmosphere, containing 10 mL of water, 3 mL of dioxane and 500 mg of 17 (2.273 mmol). The medium is heated at 100° C. with stirring for 3 hours. 20 mL of EtOAc are then added and the mixture is washed with twice 20 mL of water. The organic phase is dried over MgSO$_4$, filtered and evaporated to dryness. The crude product is chromatographed on a silica cartridge (30 g) eluting with heptane/EtOAc (as an EtOAc gradient: 10% to 50%). 230 mg of expected product 42 are collected (white solid).

$^1$H NMR (500 MHz, DMSO-d$_6$), δ (ppm): 7.59 (t, J=8.0 Hz, 1H); 7.77 (t, J=8.0 Hz, 1H); from 7.93 to 8.04 (m, 3H); 8.12 (broad s, 1H); 8.22 (dt, J=2.0 and 8.0 Hz, 1H).

Step 2: Preparation of S-(3'-cyano-3-nitrobiphenyl-2-yl)-N-[(2,2-dimethyl-propanoyl)oxy]-L-cysteine (43)

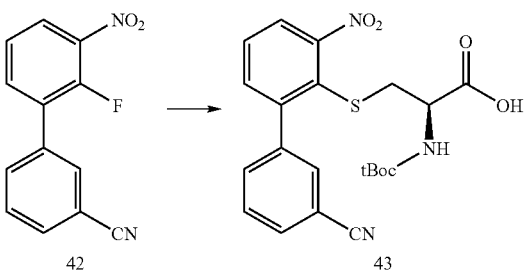

A solution of 42 (360 mg, 1.657 mmol) in 3.0 mL of ethanol is introduced dropwise into a 25 mL three-necked flask containing 210 mg of L-Boc-Cys-OH (0.950 mmol), 2.5 mL of water and 231 mg of NaHCO$_3$ (2.746 mmol). The medium is refluxed for 2 hours, the ethanol is then evaporated off and 5 mL of distilled water are added. The aqueous phase is then washed twice with 10 mL of ether, and once the ether phase has been separated out by settling, the aqueous phase is brought to pH 2-3 with HCl (1N) and extracted twice with 10 mL of EtOAc. The organic phases are combined, dried over MgSO$_4$, filtered and finally evaporated to dryness. 0.41 g of crude product 43 is obtained, which product is used directly in the following step.

$^1$H NMR (400 MHz, DMSO-d$_6$), δ (ppm): 1.33 (s, 9H); from 2.47 to 2.60 (partially masked m, 2H); 3.54 (m, 1H); 6.79 (d, J=8.0 Hz, 1H); from 7.63 to 7.73 (m, 3H); from 7.84 to 7.95 (m, 3H); 7.98 (broad s, 1H); 12.55 (broad m, 1H).

Step 3: Preparation of S-(3-amino-3'-cyanobiphenyl-2-yl)-N-[(2,2-dimethyl-propanoyl)oxy]-L-cysteine (44)

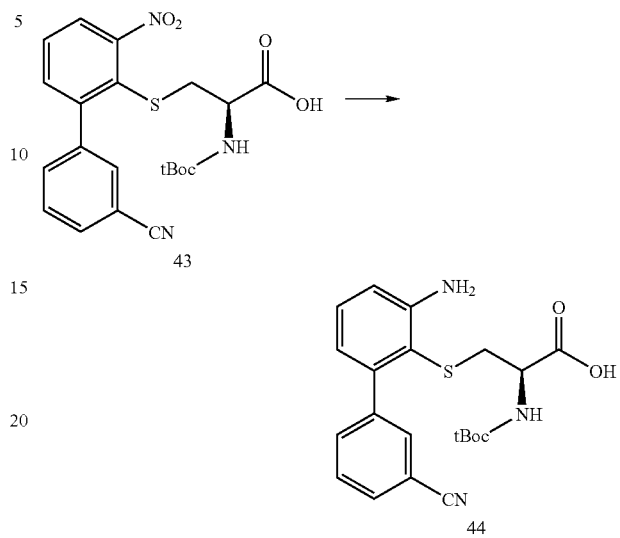

410 mg of 43 (0.925 mmol), 41 mg of Pd/C (10%) and 20 mL of MeOH are hydrogenated at 7 bar for 10 hours at 20° C. in an autoclave. After filtering off the catalyst through Celite, the solvent is evaporated off to give 350 mg of expected product 44, which product is used directly in the following step.

$^1$H NMR (400 MHz, DMSO-d$_6$), δ (ppm): 1.32 (s, 9H); from 2.60 to 2.79 (m, 2H); 3.72 (m, 1H); 5.70 (very broad m, 2H); 6.48 (broad d, J=8.0 Hz, 1H); 6.70 (broad d, J=8.0 Hz, 1H); 6.80 (broad d, J=8.0 Hz, 1H); 7.11 (t, J=8.0 Hz, 1H); from 7.52 to 7.83 (m, 4H); 12.5 (very broad m, 1H).

Step 4: Preparation of 3-[(3R)-3-{[(2,2-dimethylpropanoyl)oxy]amino}-4-oxo-2,3,4,5-tetrahydro-1,5-benzothiazepin-9-yl]benzonitrile (45)

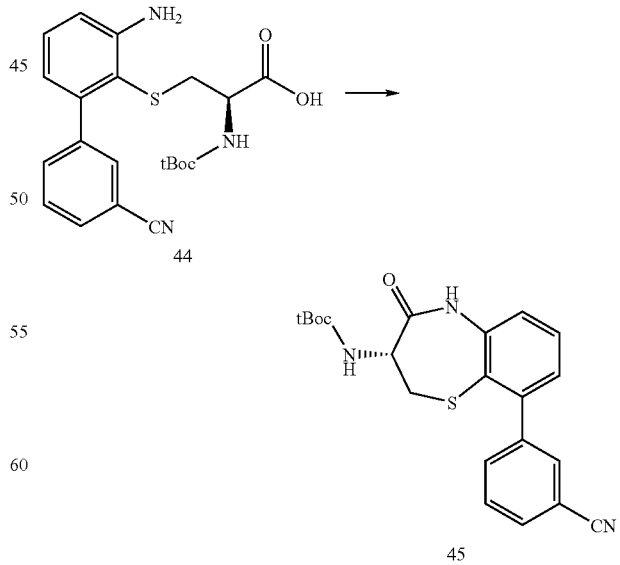

0.153 mL of diethyl cyanophosphonate (0.164 mg, 1.01 mmol) is placed in a 25 mL three-necked flask containing 350 mg of 41 (0.846 mmol) and 4.1 mL of DMF, at 0° C., followed by addition, after 10 minutes, of 0.114 mL of TEA (0.811 mmol). The reaction medium is stirred at 0° C. for 2 hours. 20 mL of EtOAc are added and the mixture is then washed with twice 20 mL of distilled water. The organic phase is dried over MgSO$_4$, filtered and then evaporated to dryness. The crude product is chromatographed on a silica cartridge (15 g) eluting with CH$_2$Cl$_2$/MeOH (as an MeOH gradient: 0 to 3%). 139 mg of expected product 45 are obtained (orange-yellow solid).

$^1$H NMR (400 MHz, DMSO-d$_6$), δ (ppm): 1.34 (s, 9H); 3.02 (t, J=12.0 Hz, 1H); 3.54 (dd, J=7.5 and 12.0 Hz, 1H); 4.21 (m, 1H); from 7.19 to 7.30 (m, 3H); 7.50 (t, J=8.0 Hz, 1H); 7.63 (t, J=8.0 Hz, 1H); 7.79 (broad d, J=8.0 Hz, 1H); 7.83 (broad d, J=8.0 Hz, 1H); 7.98 (broad s, 1H); 10.05 (s, 1H).

Step 4: Preparation of 3-[(3R)-3-amino-4-oxo-2,3,4,5-tetrahydro-1,5-benzothiazepin-9-yl]benzonitrile hydrochloride (46)

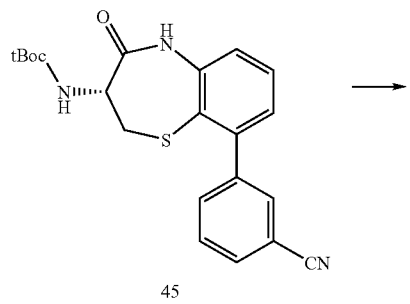

45

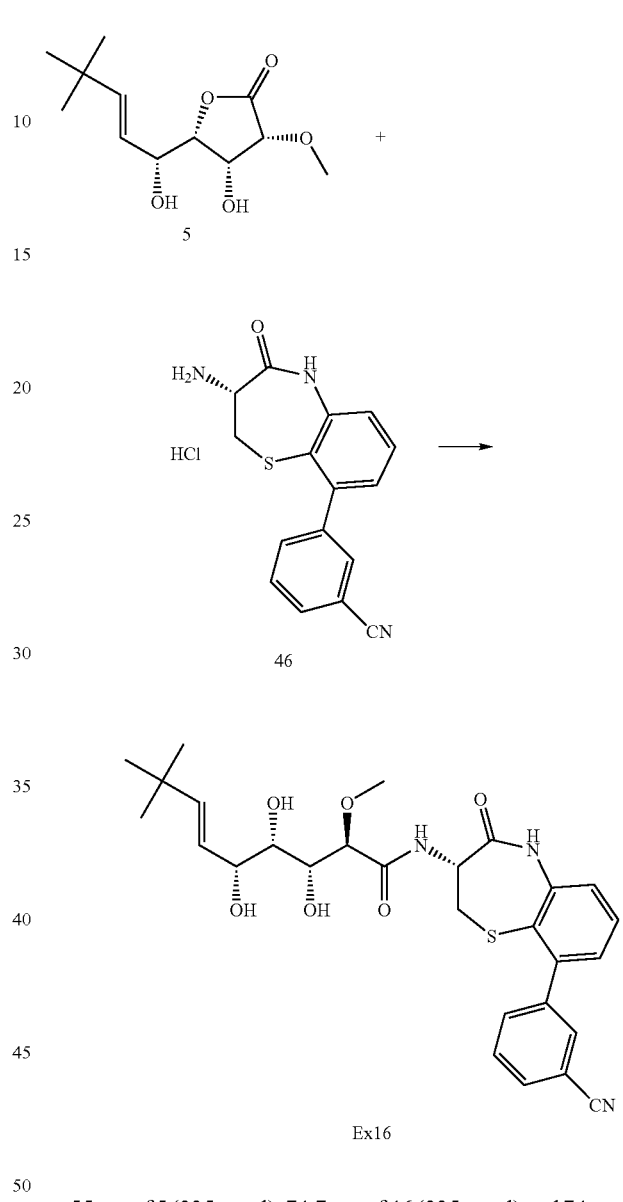

2.6 mL of a solution of hydrogen chloride in dioxane (4 M) are added to a 25 mL round-bottomed flask containing 139 mg of 45 (0.352 mmol). The mixture is stirred for 4 hours at room temperature under argon. A white precipitate forms, which is filtered off by suction and washed with 3 mL of dioxane and then 5 mL of isopropyl ether. 72 mg of amine 46 (white solid) are thus obtained in the form of the hydrochloride.

$^1$H NMR (300 MHz, DMSO-d$_6$), δ (ppm): 3.19 (t, J=12.0 Hz, 1H); 3.68 (dd, J=7.5 and 12.0 Hz, 1H); 4.15 (dd, J=7.5 and 12.0 Hz, 1H); 7.25 (broad d, J=8.0 Hz, 1H); 7.32 (broad d, J=8.0 Hz, 1H); 7.57 (t, J=8.0 Hz, 1H); 7.69 (t, J=8.0 Hz, 1H); 7.77 (broad d, J=8.0 Hz, 1H); 7.89 (broad d, J=8.0 Hz, 1H); 7.92 (broad s, 1H); 8.31 (broad s, 3H); 10.7 (s, 1H).

Step 5: Preparation of (2R,3R,4S,5R,6E)-N-[(3R)-9-(3-cyanophenyl)-4-oxo-2,3,4,5-tetrahydro-1,5-benzothiazepin-3-yl]-3,4,5-trihydroxy-2-methoxy-8,8-dimethylnon-6-enamide (Example 16)

55 mg of 5 (225 μmol), 74.7 mg of 46 (225 μmol) and 74 mg of sodium 2-ethylhexanoate (0.44 mmol) in 1.3 mL of THF are successively introduced into a Wheaton tube, with stirring and under an argon atmosphere. Stirring is continued at room temperature for 48 hours. The reaction medium is concentrated to dryness. The residues are chromatographed on a silica cartridge (5 g, CH$_2$Cl$_2$/MeOH eluent as a gradient: 1% to 10% MeOH). 100 mg of expected product Example 16 are collected (white solid).

$^1$H NMR (400 MHz, DMSO-d$_6$), δ (ppm): 0.96 (s, 9H); 3.12 (t, J=12.0 Hz, 1H); 3.22 (s, 3H); 3.30 (masked m, 1H); from 3.53 to 3.57 (m, 2H); 3.69 (d, J=8.0 Hz, 1H); 3.94 (m, 1H); 4.24 (d, J=7.0 Hz, 1H); 4.29 (broad d, J=6.5 Hz, 1H); 4.53 (m, 2H); 5.30 (dd, J=7.0 and 16.0 Hz, 1H); 5.63 (d, J=16.0 Hz, 1H); 7.23 (broad d, J=7.5 Hz, 1H); 7.30 (broad d, J=7.5 Hz, 1H); 7.52 (t, J=7.5 Hz, 1H); 7.65 (t, J=7.5 Hz, 1H);

7.75 (broad d, J=7.5 Hz, 1H); 7.85 (broad d, J=7.5 Hz, 1H); 7.91 (broad s, 1H); 8.29 (d, J=8.0 Hz, 1H); 10.2 (s, 1H).

EXAMPLE 17

(2R,3R,4S,5R,6E)-N-[(3R)-6-fluoro-4-oxo-2,3,4,5-tetrahydro-1,5-benzothiazepin-3-yl]-3,4,5-trihydroxy-2-methoxy-8,8-dimethylnon-6-enamide

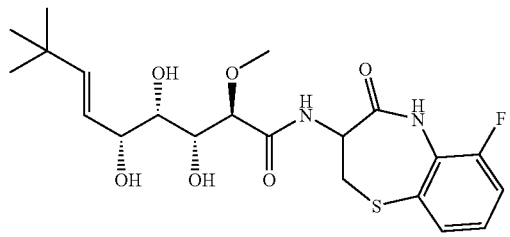

Step 1: Preparation N-[(2,2-dimethylpropanoyl)oxy]-S-(3-fluoro-2-nitrophenyl)-L-cysteine (48)

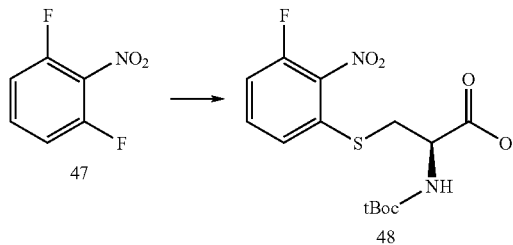

A solution of 2,6-difluoronitrobenzene 47 (2.0 g, 12.57 mmol) in 26 mL of ethanol is introduced into a 50 mL three-necked flask containing 2.78 g of L-Boc-Cys-OH (12.57 mmol), 22 mL of water and 3.05 g of NaHCO₃ (36.33 mmol). The reaction medium is left at room temperature overnight and the medium is then maintained at 75° C. for 1 hour. The ethanol is evaporated off, the aqueous phase is then washed with 20 mL of ether, and once the ether phase has been separated out by settling, the aqueous phase is brought to pH 2-3 with HCl (1N) and extracted twice with 25 mL of EtOAc. The organic phases are combined, dried over MgSO₄, filtered and finally evaporated to dryness. 1.29 g of crude product 48 are obtained (yellow oil), which product is used directly in the following step.

¹H NMR (400 MHz, DMSO-d₆), δ (ppm): 1.36 (s, 9H); 3.24 (dd, J=10.0 and 13.5 Hz, 1H); 3.53 (dd, J=5.0 and 13.5 Hz, 1H); 4.08 (m, 1H); 7.20 (d, J=8.0 Hz, 1H); 7.44 (t, J=8.0 Hz, 1H); 7.57 (t, J=8.0 Hz, 1H); 7.69 (dt, J=6.0 and 8.0 Hz, 1H); 12.8 (broad m, 1H).

Step 2: Preparation of S-(2-amino-3-fluorophenyl)-N-[(2,2-dimethylpropanoyl)oxy]-L-cysteine (49)

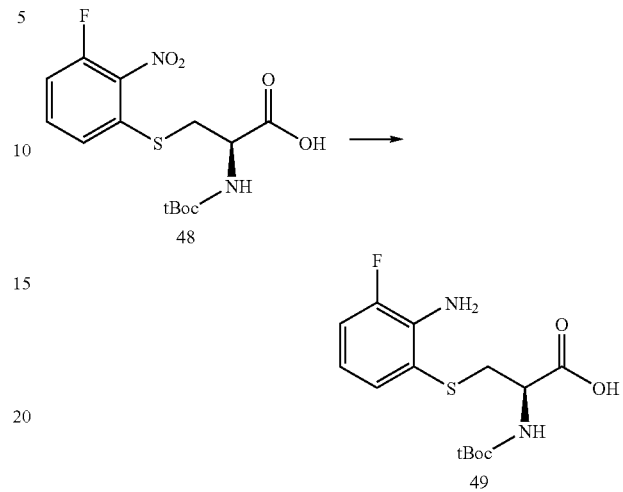

790 mg of 48 (2.192 mmol), 79 mg of Pd/C (10%) and 20 mL of ethanol are hydrogenated at 7 bar for 10 hours at 20° C. in an autoclave. After filtering off the catalyst through Celite, the solvent is evaporated off and 670 mg of expected product 49 are obtained (yellow oil), which product is used directly in the following step.

ES: m/z=329 (M–H⁺)

¹H NMR (400 MHz, DMSO-d₆), δ (ppm): 1.38 (s, 9H); 2.94 (dd, J=10.0 and 13.5 Hz, 1H); 3.09 (dd, J=5.0 and 13.5 Hz, 1H); 3.94 (m, 1H); 5.30 (broad s, 2H); 6.52 (dt, J=6.0 and 8.0 Hz, 1H); from 6.99 to 7.15 (m, 4H).

Step 3 Preparation of (3R)-3-{[(2,2-dimethylpropanoyl)oxy]amino}-6-fluoro-2,3-dihydro-1,5-benzothiazepin-4(5H)-one (50)

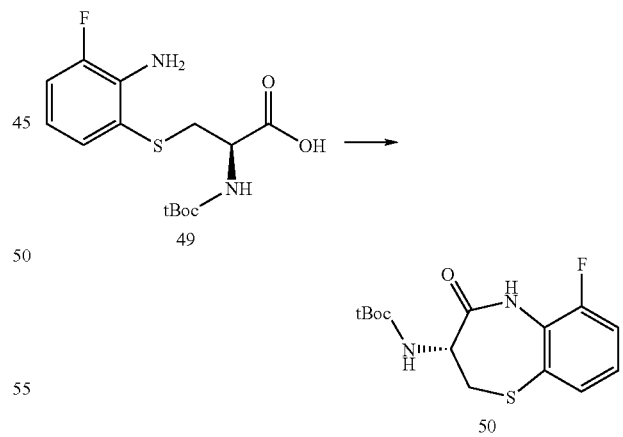

0.366 mL of diethyl cyanophosphonate (0.393 mg, 2.41 mmol) is placed in a 25 mL three-necked flask containing 670 mg of 49 (2.028 mmol) and 10 mL of DMF, at 0° C., followed by addition, after 10 minutes, of 0.273 mL of TEA (1.943 mmol). The reaction medium is stirred at 0° C. for 2 hours. 30 mL of EtOAc are added and the mixture is then washed with twice 30 mL of distilled water. The organic phase is dried over MgSO₄, filtered and then evaporated to dryness. The crude product is chromatographed on a silica cartridge (70 g) with a heptane/EtOAc eluent (as an EtOAc gradient: 8% to 50%). 68.4 mg of expected product 50 are obtained (white solid).

ES: m/z=311 (M−H⁺)

¹H NMR (400 MHz, DMSO-d₆), δ (ppm): 1.33 (s, 9H); 3.09 (t, J=12.0 Hz, 1H); 3.52 (dd, J=8.0 and 12.0 Hz, 1H); 4.09 (m, 1H); 7.27 (m, 2H); 7.39 (t, J=9.0 Hz, 1H); 7.44 (d, J=8.0 Hz, 1H); 9.96 (s, 1H).

Step 4: Preparation of (3R)-3-amino-6-fluoro-2,3-dihydro-1,5-benzothiazepin-4(5H)-one hydrochloride (51)

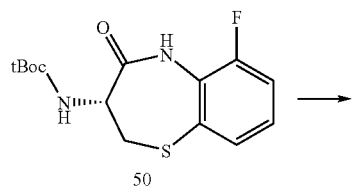

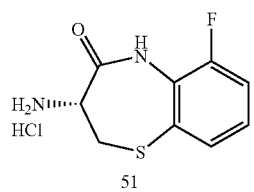

1.6 mL of a solution of hydrogen chloride in dioxane (4 M) are added to a 25 mL round-bottomed flask containing 68.4 mg of 50 (0.219 mmol). The mixture is stirred for 4 hours at room temperature under argon. After concentrating the reaction medium to dryness, 51 mg of amine 51 (yellow solid) are thus obtained in the form of the hydrochloride.

¹H NMR (300 MHz, DMSO-d₆), δ (ppm): 3.23 (t, J=12.0 Hz, 1H); 3.75 (dd, J=7.5 and 12.0 Hz, 1H); 4.03 (dd, J=7.5 and 12.0 Hz, 1H); 7.32 (dt, J=6.0 and 8.0 Hz, 1H); 7.43 (t, J=8.0 Hz, 1H); 7.50 (d, J=8.0 Hz, 1H); 8.42 (broad s, 3H); 10.55 (s, 1H).

Step 5: Preparation of (2R,3R,4S,5R,6E)-N-[(3R)-6-fluoro-4-oxo-2,3,4,5-tetrahydro-1,5-benzothiazepin-3-yl]-3,4,5-trihydroxy-2-methoxy-8,8-dimethynon-6-enamide (Example 17)

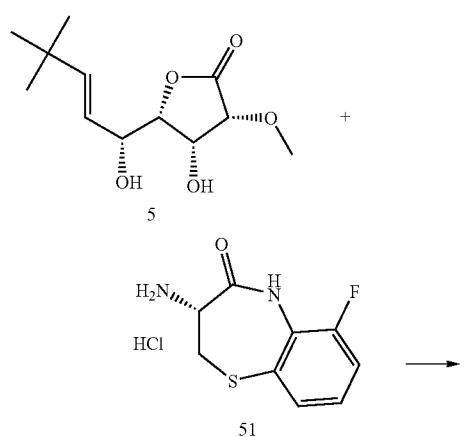

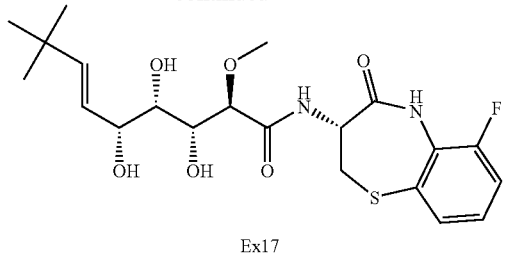

50 mg of 5 (204 μmol), 51 mg of 51 (204 μmol) and 69 mg of sodium 2-ethylhexanoate (0.42 mmol) in 1.2 mL of THF are successively introduced into a Wheaton tube, with stirring and under an argon atmosphere. Stirring is continued at room temperature for 48 hours. The reaction medium is concentrated to dryness. The residues are chromatographed on a silica cartridge (5 g, CH₂Cl₂/MeOH eluent as a gradient: 1% to 10% MeOH). 70 mg of expected product Example 17 are collected (white solid).

ES: m/z=457 (MH⁺)

¹H NMR (400 MHz, DMSO-d₆), δ (ppm): 0.96 (s, 9H); 3.18 (t, J=12.0 Hz, 1H); 3.21 (s, 3H); 3.30 (masked m, 1H); from 3.45 to 3.59 (m, 2H); 3.68 (d, J=8.0 Hz, 1H); 3.92 (m, 1H); 4.29 (d, J=7.5 Hz, 2H); 4.42 (m, 1H); 4.52 (d, J=5.0 Hz, 1H); 5.29 (dd, J=7.5 and 16.0 Hz, 1H); 5.62 (d, J=16.0 Hz, 1H); 7.29 (m, 1H); 7.40 (t, J=7.5 Hz, 1H); 7.48 (d, J=7.5 Hz, 1H); 8.23 (d, J=8.0 Hz, 1H); 10.1 (s, 1H).

EXAMPLE 18

(2R,3R,4S,5R,6E)-3,4,5-trihydroxy-2-methoxy-N-[(3R)-6-methoxy-4-oxo-2,3,4,5-tetrahydro-1,5-benzothiazepin-3-yl]-8,8-dimethylnon-6-enamide

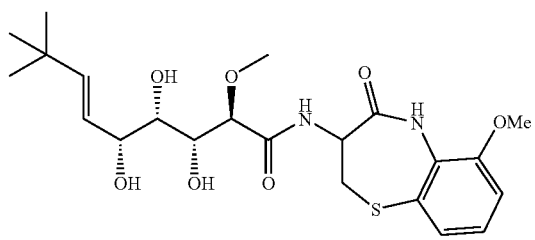

Step 1: Preparation of 1-fluoro-3-methoxy-2-nitrobenzene (52)

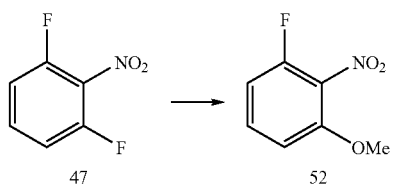

252 mg of sodium hydride as a 60% suspension in oil (6.29 mmol) are placed in a 100 mL three-necked flask containing 10 mL of THF and 0.255 mL of MeOH. The mixture is stirred at room temperature for 1 hour, and a solution of 2,6-difluoronitrobenzene 47 (1.0 g, 6.29 mmol) in 10 mL of THF is added. The reaction medium is left at room temperature for 16 hours. 10 mL of EtOAc are added and the resulting mixture is washed twice with 20 mL of distilled water. The organic phase is dried over MgSO$_4$, filtered and finally evaporated to dryness. 0.93 g of product 52 is obtained (cream-coloured solid).

$^1$H NMR (400 MHz, DMSO-d$_6$), δ (ppm): 3.95 (s, 3H); 7.15 (broad t, J=8.0 Hz, 1H); 7.21 (broad d, J=8.0 Hz, 1H); 7.65 (dt, J=6.0 and 8.0 Hz, 1H).

Step 2: Preparation of the acid N-[(2,2-dimethylpropanoyl) oxy]-S-(3-methoxy-2-nitrophenyl)-L-cysteine (53)

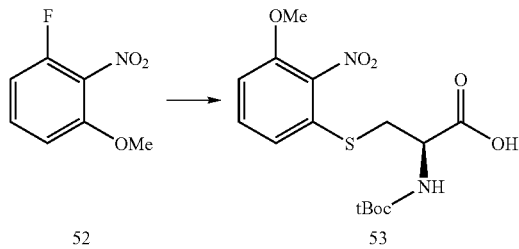

A solution of 52 (1.1 g, 6.428 mmol) in 17 mL of ethanol is placed in a 100 mL three-necked flask containing 1.422 g of L-Boc-Cys-OH (6.428 mmol), 13 mL of water and 1.561 g of NaHCO$_3$ (18.58 mmol). The medium is heated at 100° C. for 6 hours. The ethanol is evaporated off, the aqueous phase is then washed with 20 mL of ether, and once the ether phase has been separated out by settling, the aqueous phase is brought to pH 2-3 with HCl (1N) and extracted twice with 25 mL of EtOAc. The organic phases are combined, dried over MgSO$_4$, filtered and finally evaporated to dryness. The residues are chromatographed on a silica cartridge (25 g, CH$_2$Cl$_2$/MeOH eluent as a gradient: 1% to 10% MeOH), 2.43 g of product 53 are obtained (cream-coloured solid).

$^1$H NMR (400 MHz, DMSO-d$_6$), δ (ppm): 1.39 (s, 9H); 3.17 (dd, J=10.0 and 14.0 Hz, 1H); 3.40 (dd, J=4.0 and 14.0 Hz, 1H); 3.89 (s, 3H); 4.03 (m, 1H); 7.20 (d, J=8.0 Hz, 1H); 7.23 (m, 2H); 7.54 (t, J=8.0 Hz, 1H); 12.8 (broad m, 1H).

Step 3: Preparation of S-(2-amino-3-methoxyphenyl)-N-[(2,2-dimethylpropanoyl)oxy]-L-cysteine (54)

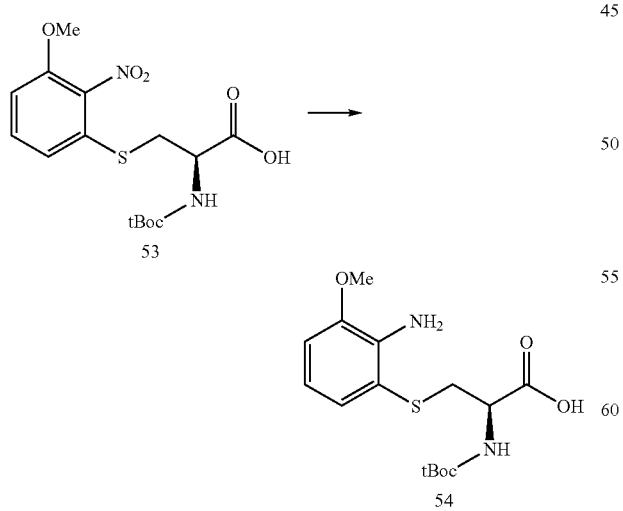

2.43 g of 53 (6.53 mmol), 285 mg of Pd/C (10%) and 174 mL of methanol are hydrogenated at 5 bar for 10 hours at 20° C. in an autoclave. After filtering off the catalyst through Celite, the solvent is evaporated off and 1.8 g of expected product 54 are obtained (brown oil), which product is used directly in the following step.

Step 4: Preparation of (3R)-3-{[(2,2-dimethylpropanoyl) oxy]amino}-6-methoxy-2,3-dihydro-1,5-benzothiazepin-4 (5H)-one (55)

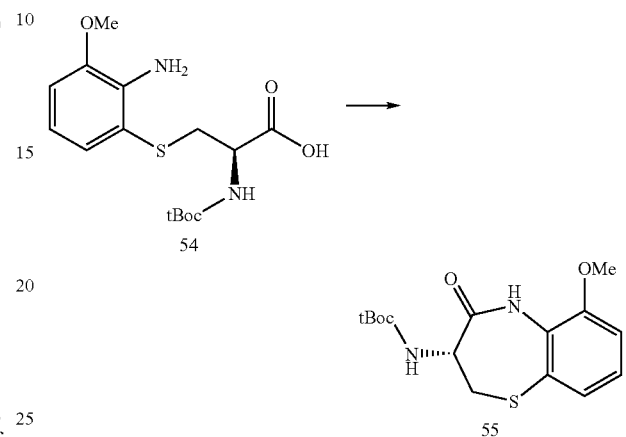

0.948 mL of diethyl cyanophosphonate (1.019 g, 6.245 mmol) is placed in a 100 mL three-necked flask containing 1.80 g of 54 (5.26 mmol) and 25 mL of DMF, at 0° C., followed by addition, after 10 minutes, of 0.708 mL of TEA (5.04 mmol). The reaction medium is stirred at 0° C. for 2 hours. 50 mL of EtOAc are added and the mixture is then washed with twice 50 mL of distilled water. The organic phase is dried over MgSO$_4$, filtered and then evaporated to dryness. The crude product is chromatographed on a silica cartridge (150 g) eluting with heptane/EtOAc (as an EtOAc gradient: 10% to 50%). 450 mg of expected product 55 are obtained (white solid).

$^1$H NMR (400 MHz, DMSO-d$_6$), δ (ppm): 1.32 (s, 9H); 3.05 (t, J=12.0 Hz, 1H); 3.48 (dd, J=7.0 and 12.0 Hz, 1H); 3.82 (s, 3H); 4.04 (m, 1H); from 7.10 to 7.12 (m, 4H); 9.40 (s, 1H).

Step 5: Preparation of (3R)-3-amino-6-methoxy-2,3-dihydro-1,5-benzothiazepin-4(5H)-one hydrochloride (56)

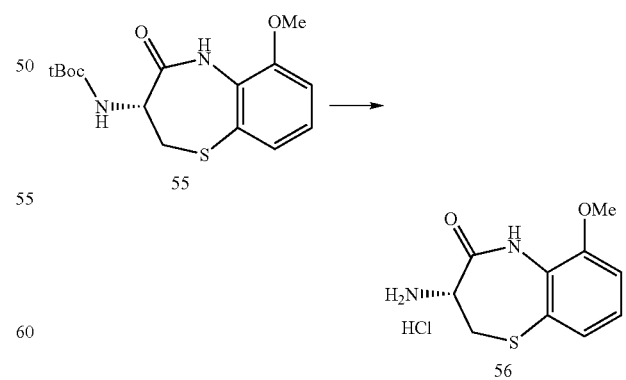

10.4 mL of a solution of hydrogen chloride in dioxane (4 M) are placed in a 100 mL round-bottomed flask containing 450 mg of 55 (1.387 mmol). The mixture is stirred for 3 hours at room temperature under argon. A white precipitate forms, which is filtered off by suction and washed with 3 mL of dioxane and then 5 mL of isopropyl ether. 259 mg of amine 56 (cream-coloured solid) are thus obtained in the form of the hydrochloride.

$^1$H NMR (300 MHz, DMSO-d$_6$), δ (ppm): 3.19 (t, J=12.0 Hz, 1H); 3.71 (m, 1H); 3.82 (s, 3H); 3.83 (m, 1H); from 7.17 to 7.30 (m, 3H); 8.39 (s, 3H); 10.05 (s, 1H).

Step 6: Preparation of (2R,3R,4S,5R,6E)-3,4,5-trihydroxy-2-methoxy-N-[(3R)-6-methoxy-4-oxo-2,3,4,5-tetrahydro-1,5-benzothiazepin-3-yl]-8,8-dimethylnon-6-enamide (Example 18)

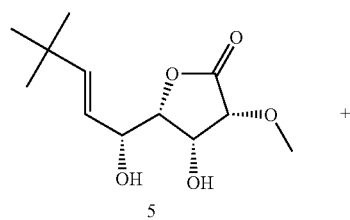

5

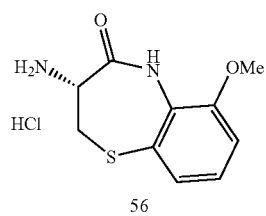

56

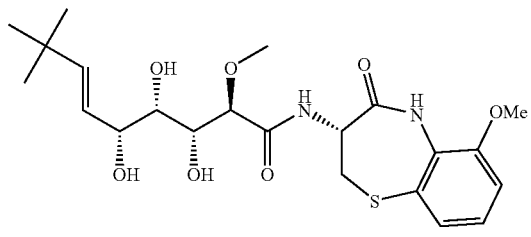

Ex18

100 mg of 5 (409 μmol), 107 mg of 56 (409 μmol) and 170 mg of sodium 2-ethylhexanoate (1.02 mmol) in 2 mL of THF are successively introduced into a Wheaton tube, with stirring and under an argon atmosphere. Stirring is continued at room temperature for 24 hours. The reaction medium is concentrated to dryness. The residues are chromatographed on a silica cartridge (12 g, eluent: EtOAc). 175 mg of expected product Example 18 are collected (white foam).

ES: m/z=467 (M−H$^+$)

$^1$H NMR (400 MHz, DMSO-d$_6$), δ (ppm): 0.96 (s, 9H); 3.09 (t, J=12.0 Hz, 1H); 3.20 (s, 3H); 3.30 (masked m, 1H); from 3.45 to 3.55 (m, 2H); 3.68 (d, J=8.0 Hz, 1H); 3.82 (s, 3H); 3.92 (m, 1H); from 4.30 to 4.45 (m, 3H); 4.55 (broad s, 1H); 5.29 (dd, J=7.0 and 16.0 Hz, 1H); 5.62 (d, J=16.0 Hz, 1H); from 7.12 to 7.26 (m, 3H); 8.10 (d, J=8.0 Hz, 1H); 9.58 (s, 1H).

EXAMPLE 19

(2R,3R,4S,5R,6E)-3,4,5-trihydroxy-2-methoxy-8,8-dimethyl-N-[(3R)-4-oxo-6-phenoxy-2,3,4,5-tetrahydro-1,5-benzothiazepin-3-yl]non-6-enamide

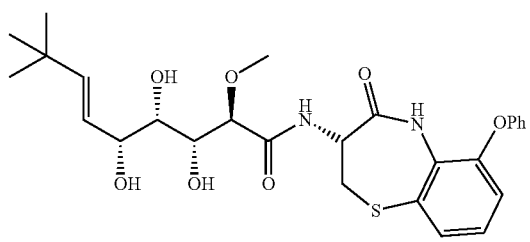

Ex19

Step 1: Preparation of 1-fluoro-2-nitro-3-phenoxybenzene (57)

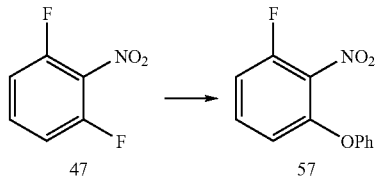

252 mg of sodium hydride as a 60% suspension in oil (6.29 mmol) are placed in a 50 mL three-necked flask containing 10 mL of DMF and 0.592 g of phenol. The mixture is stirred at room temperature for 1 hour and a solution of 2,6-difluoronitrobenzene 47 (1.0 g, 6.29 mmol) in 10 mL of DMF is added. The reaction medium is left at room temperature for 24 hours. 50 mL of EtOAc are added and the mixture is washed twice with 20 mL of distilled water. The organic phase is dried over MgSO$_4$, filtered and finally evaporated to dryness. The crude product is chromatographed on a silica cartridge (120 g) eluting with heptane/EtOAc (as an EtOAc gradient: 0 to 50%). 1.07 g of expected product 57 are obtained (yellow oil).

$^1$H NMR (400 MHz, DMSO-d$_6$), δ (ppm): 6.92 (broad d, J=8.0 Hz, 1H); 7.17 (broad d, J=7.5 Hz, 2H); 7.29 (t, J=7.5 Hz, 1H); 7.36 (broad t, J=8.0 Hz, 1H); 7.48 (t, J=7.5 Hz, 2H); 7.65 (dt, J=6.0 and 8.0 Hz, 1H).

Step 2: Preparation N-[(2,2-dimethylpropanoyl)oxy]-S-(2-nitro-3-phenoxyphenyl)-L-cysteine (58)

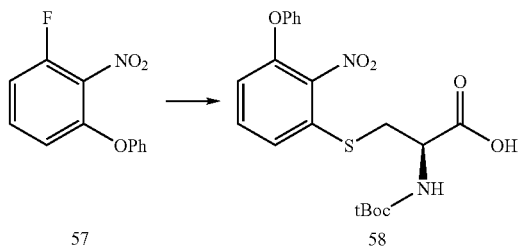

A solution of 57 (0.73 g, 3.13 mmol) in 8 mL of ethanol is placed in a 25 mL three-necked flask containing 0.693 g of L-Boc-Cys-OH (3.13 mmol), 6.3 mL of water and 0.76 g of NaHCO$_3$ (9.05 mmol). The medium is heated at 75° C. for 6 hours. The ethanol is evaporated off, 10 mL of distilled water are added, the aqueous phase is then washed twice with 10 mL of ether, and once the ether phase has been separated out by settling, the aqueous phase is brought to pH 2-3 with HCl (1N) and extracted twice with 10 mL of EtOAc. The organic phases are combined, dried over MgSO$_4$, filtered and finally evaporated to dryness. The residues are chromatographed on a silica cartridge (50 g, CH$_2$Cl$_2$/MeOH eluent as a gradient: 1% to 10% MeOH) to give 760 mg of product 58 (yellow oil).

$^1$H NMR (400 MHz, DMSO-d$_6$), δ (ppm): 1.38 (s, 9H); 3.22 (dd, J=9.0 and 14.0 Hz, 1H); 3.50 (dd, J=5.0 and 14.0 Hz, 1H); 4.08 (m, 1H); 6.96 (d, J=8.0 Hz, 1H); 7.10 (d, J=8.0 Hz, 2H); from 7.18 to 7.28 (m, 2H); from 7.39 to 7.49 (m, 3H); 7.56 (t, J=8.0 Hz, 1H); 12.85 (broad m, 1H).

Step 3: Preparation of S-(2-amino-3-phenoxyphenyl)-N-[(2,2-dimethylpropanoyl)oxy]-L-cysteine (59)

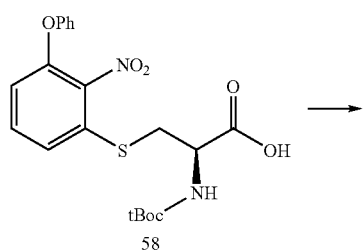

0.76 g of 58 (1.75 mmol), 76 mg of Pd/C (10%) and 34.5 mL of methanol are hydrogenated at 5 bar for 10 hours at 20° C. in an autoclave. After filtering off the catalyst through Celite, the solvent is evaporated off and 0.63 g of expected product 59 is obtained (brown oil), which product is used directly in the following step.

$^1$H NMR (400 MHz, DMSO-d$_6$), δ (ppm): 1.39 (s, 9H); 2.96 (m, 1H); 3.11 (m, 1H); 3.98 (m, 1H); 5.10 (broad m, 2H); 6.58 (t, J=8.0 Hz, 1H); 6.80 (d, J=8.0 Hz, 1H); 6.92 (d, J=7.5 Hz, 2H); from 7.00 to 7.20 (m, 3H); 7.34 (t, J=7.5 Hz, 2H); 12.5 (very broad m, 1H).

Step 4: Preparation of (3R)-3-{[(2,2-dimethylpropanoyl)oxy]amino}-6-phenoxy-2,3-dihydro-1,5-benzothiazepin-4(5H)-one (60)

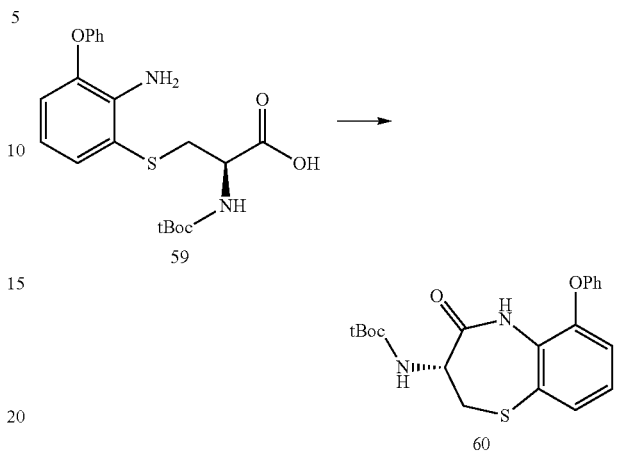

0.281 mL of diethyl cyanophosphonate (0.302 g, 1.85 mmol) is placed in a 25 mL three-necked flask containing 0.63 g of 59 (1.56 mmol) and 7.5 mL of DMF, at 0° C., followed by addition, after 10 minutes, of 0.21 mL of TEA (1.49 mmol). The reaction medium is stirred at 0° C. for 2 hours. 15 mL of EtOAc are added and the mixture is then washed with twice 15 mL of distilled water. The organic phase is dried over MgSO$_4$, filtered and then evaporated to dryness. The crude product is chromatographed on a silica cartridge (120 g) with a heptane/EtOAc eluent (as an EtOAc gradient: 0 to 30%). 188 mg of expected product 60 are obtained (white solid).

$^1$H NMR (400 MHz, DMSO-d$_6$), δ (ppm): 1.35 (s, 9H); 3.09 (t, J=12.0 Hz, 1H); 3.52 (dd, J=7.0 and 12.0 Hz, 1H); 4.21 (m, 1H); from 6.97 to 7.05 (m, 3H); from 7.08 to 7.18 (m, 2H); 7.21 (t, J=7.5 Hz, 1H); 7.37 (t, J=7.5 Hz, 2H); 7.42 (d, J=7.5 Hz, 1H); 9.81 (s, 1H).

Step 5: Preparation of (3R)-3-amino-6-phenoxy-2,3-dihydro-1,5-benzothiazepin-4(5H)-one hydrochloride (61)

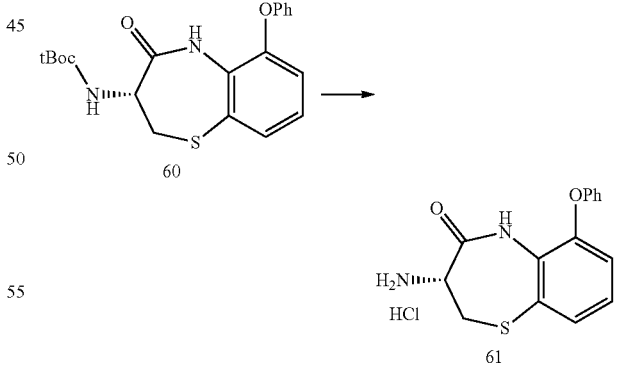

3.65 mL of a solution of hydrogen chloride in dioxane (4 M) are placed in a 100 mL round-bottomed flask containing 188 mg of 60 (0.487 mmol). The reaction medium is concentrated to dryness and the residue is taken up in 10 mL of isopropyl ether. After filtering, 100 mg of amine 61 (white solid) are obtained in the form of the hydrochloride.

$^1$H NMR (400 MHz, DMSO-d$_6$), δ (ppm): 3.22 (t, J=12.0 Hz, 1H); 3.79 (dd, J=7.0 and 12.0 Hz, 1H); 4.08 (dd, J=6.0 and 12.0 Hz, 1H); 6.97 (broad d, J=7.5 Hz, 1H); 7.04 (d, J=7.5 Hz, 2H); 7.19 (t, J=7.5 Hz, 1H); 7.23 (t, J=8.0 Hz, 1H); 7.42 (m, 3H); 8.44 (broad s, 3H); 10.45 (s, 1H).

Step 6: Preparation of (2R,3R,4S,5R,6E)-3,4,5-trihydroxy-2-methoxy-8,8-dimethyl-N -[(3R)-4-oxo-6-phenoxy-2,3,4,5-tetrahydro-1,5-benzothiazepin-3-yl]non-6-enamide (Example 19)

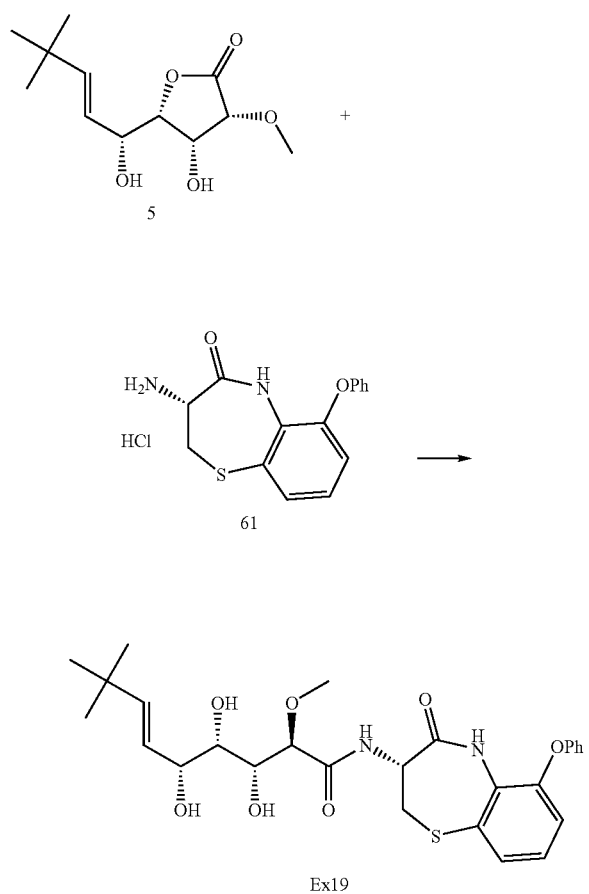

75 mg of 5 (307 μmol), 99.1 mg of 61 (307 μmol) and 127 mg of sodium 2-ethylhexanoate (0.77 mmol) in 1.6 mL of THF are successively introduced into a Wheaton tube, with stirring and under an argon atmosphere. Stirring is continued at room temperature for 24 hours. The reaction medium is concentrated to dryness. The residues are chromatographed on a silica cartridge (5 g, eluent: EtOAc). 56 mg of expected product Example 19 are collected (white foam).

ES: m/z=529 (M−H$^+$)

$^1$H NMR (400 MHz, DMSO-d$_6$), δ (ppm): 0.95 (s, 9H); 3.12 (t, J=12.0 Hz, 1H); 3.19 (s, 3H); 3.30 (masked m, 1H); 3.50 (m, 1H); 3.54 (dd, J=6.5 and 12.0 Hz, 1H); 3.69 (d, J=8.0 Hz, 1H); 3.94 (m, 1H); 4.32 (m, 2H); 4.52 (m, 1H); 4.58 (d, J=4.5 Hz, 1H); 5.30 (dd, J=6.5 and 16.0 Hz, 1H); 5.62 (d, J=16.0 Hz, 1H); 7.00 (m, 3H); 7.12 (t, J=7.5 Hz, 1H); 7.22 (t, J=7.5 Hz, 1H); 7.38 (t, J=7.5 Hz, 2H); 7.42 (broad d, J=7.5 Hz, 1H); 8.19 (d, J=8.0 Hz, 1H); 9.97 (s, 1H).

EXAMPLE 20

(2R,3R,4S,5R,6Z)-3,4,5-trihydroxy-2-methoxy-8,8-dimethyl-N-[(3R)-5-methyl-4-oxo-2,3,4,5-tetrahydro-1,5-benzothiazepin-3-yl]non-6-enamide

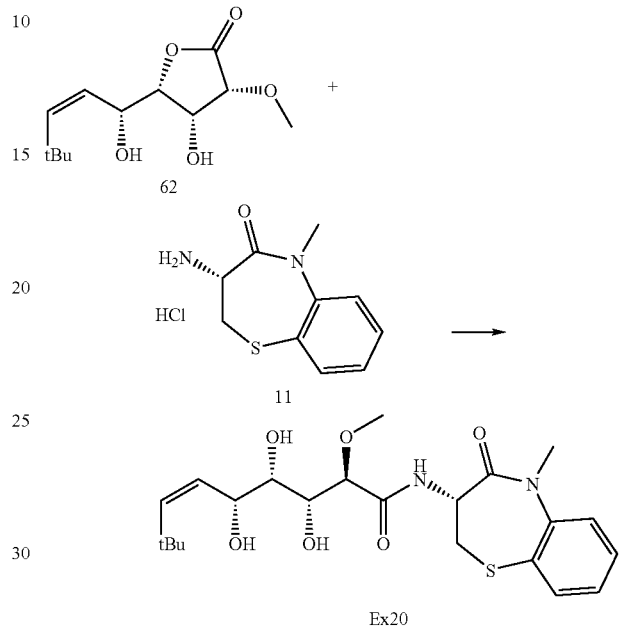

50 mg of 62 (205 μmol) (prepared according to the procedure described in step three of Example 1, starting with (4S,4aS,7R,7aR)-4-((Z)-3,3-dimethylbut-1-enyl)-7-methoxy-2,2-dimethyltetrahydrofuro[3,2-d]-1,3-dioxin-6-one, obtained in minor amount during the preparation of 4, according to the procedure described in Org. Process Res. Dev. 2003, 7(6), 856-865), 61 mg of 11 (246 μmol) and 51 mg of sodium 2-ethylhexanoate (0.31 mmol) in 1 mL of THF are successively introduced into a 5 mL round-bottomed flask, with stirring and under an argon atmosphere. Stirring is continued at room temperature for 24 hours. 10 mL of CH$_2$Cl$_2$ are added to the reaction medium. The resulting mixture is washed with 5 mL of HCl solution (1N). The organic phase is dried over anhydrous magnesium sulfate, filtered and then evaporated to dryness. The crude product (0.15 g) is chromatographed on a silica cartridge (5 g, eluent: 10/90 heptane/EtOAc). 68 mg of expected product Example 20 are collected.

ES: m/z=451 (M−H)$^-$.

$^1$H NMR (300 MHz, DMSO-d$_6$), δ (ppm): 0.95 (s, 9H); 3.12 (t, J=12.0 Hz, 1H); 3.19 (s, 3H); 3.30 (masked m, 1H); 3.50 (m, 1H); 3.54 (dd, J=6.5 and 12.0 Hz, 1H); 3.69 (d, J=8.0 Hz, 1H); 3.94 (m, 1H); 4.32 (m, 2H); 4.52 (m, 1H); 4.58 (d, J=4.5 Hz, 1H); 5.30 (dd, J=6.5 and 16.0 Hz, 1H); 5.62 (d, J=16.0 Hz, 1H); 7.00 (m, 3H); 7.12 (t, J=7.5 Hz, 1H); 7.22 (t, J=7.5 Hz, 1H); 7.38 (t, J=7.5 Hz, 2H); 7.42 (broad d, J=7.5 Hz, 1H); 8.19 (d, J=8.0 Hz, 1H); 9.97 (s, 1H).

Biological Activity of the Prepared Products:

On the day of filing of the patent application, it was measured that Caco2-TC7 of the product of Example 5 is Papp single point=23×10$^{-7}$ cm·sec$^{-1}$. This compound has better total metabolic stability (11% metabolization in mice) than the product of Example 20 (99%) described in patent application WO 2006/056 696.

The antiproliferative activity of the products of the examples of Table 1 was determined by measuring the inhibition of cell proliferation of HCT116 cells. The cells are inoculated in a cell culture medium at a concentration of 10 000 cells per well, in 0.17 mL of medium, and 20 μL of test product, at various concentrations, and 10 μL of thymidine [methyl-14C] (100 μCi/ml—specific activity 47.90 mCi/mmol; NEN Technologies reference NEC568 batch 3550-001) are added, and the cells are then incubated at 37° C. and 5% $CO_2$.

Medium used for the HCT116 cell culturing: DMEM medium 2 mM L-glutamine, 200 IU/ml penicillin, 200 μg/mL streptomycin and 10% (V/V) foetal calf serum (Life Technologies).

After 96 hours, the incorporation of $^{14}C$-thymidine is counted in a 1450 Microbeta Wallac Trilux liquid scintillation counter. The results R are expressed in cpm (counts per minute) and converted to a percentage of growth inhibition GI % by first subtracting the average number of cpm for the wells without B cells and then dividing the number of cpm for the wells of the untreated cells C comprising 20 μL of product dilution medium containing 1% ethanol. (GI %=(R−B)× 100/C %).

The IC50 values are calculated by means of equation 205 of the XLFit software (IDBS company, UK) via non-linear regression analysis using the Marquardt algorithm (Donald W. Marquardt, J. Soc. Industry. Appl., vol. 11, No. 2, June, 1963).

The products of Table 1 have an IC50 on HCT116 cells generally of less than 30 μM and preferably less than 100 nM. For example, the product of Example 3 has an $IC_{50}$ of 10 nM and the product of Example 5 has an IC50 of 14 nM. The product of Example 1 has an IC50 of 9 nM, the product of Example 2 has an IC50 of 20 nM, the product of Example 4 has an IC50 of 19 nM and the product of Example 9 has an IC50 of 7 nM.

TABLE 1

| Example | Structure |
|---------|-----------|
| Example 1 | 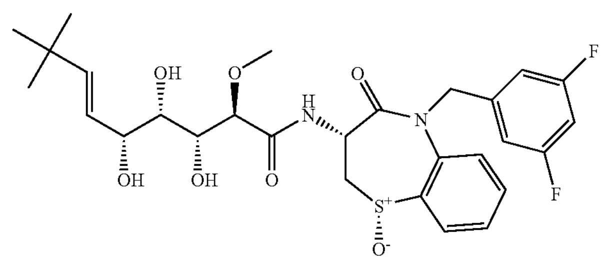 |
| Example 2 | 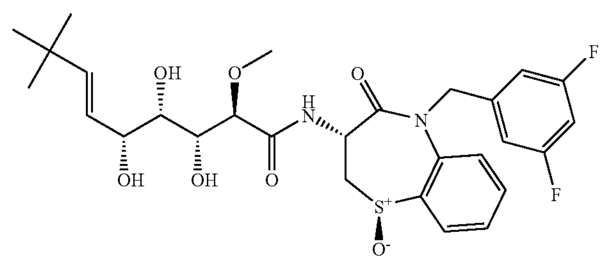 |
| Example 3 | 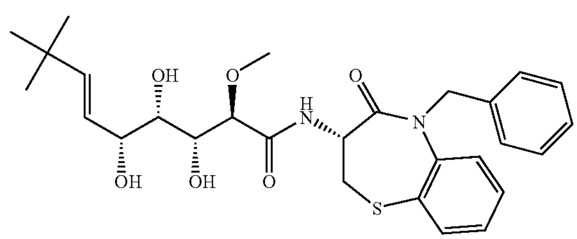 |
| Example 4 | 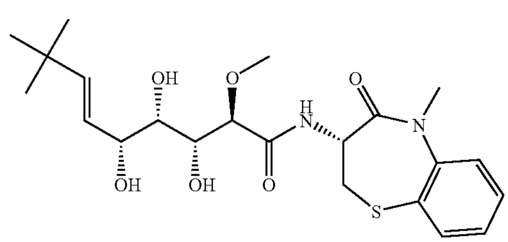 |

TABLE 1-continued
| Example | Structure |
|---|---|
| Example 5 | 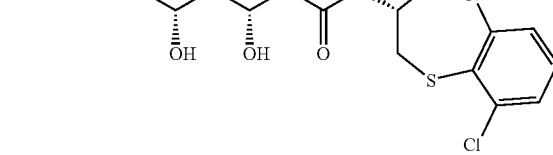 |
| Example 6 | 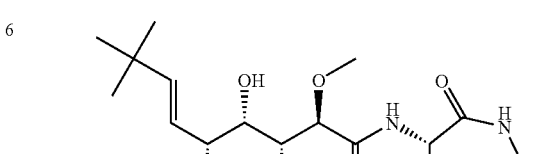 |
| Example 7 | 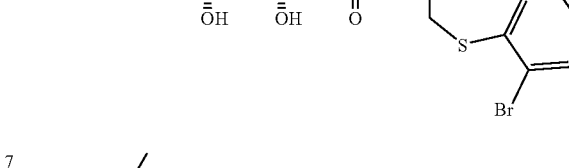 |
| Example 8 | 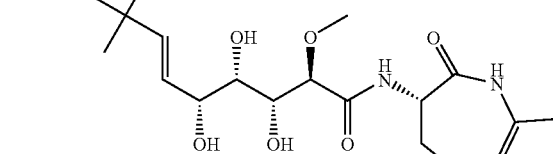 |
| Example 9 | 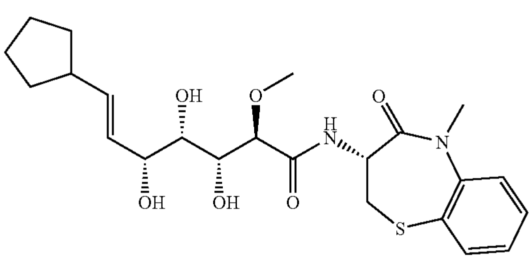 |
| Example 10 | 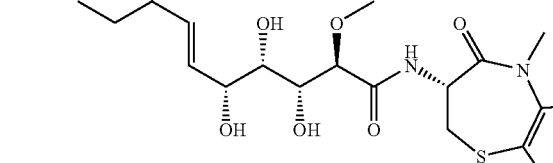 |

TABLE 1-continued
| Example | Structure |
|---|---|
| Example 11 | 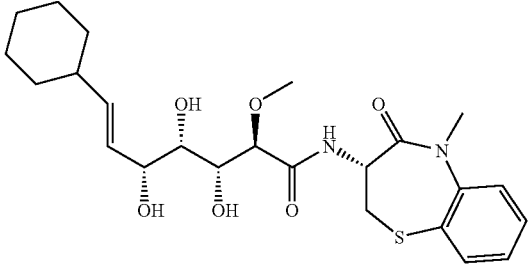 |
| Example 12 | 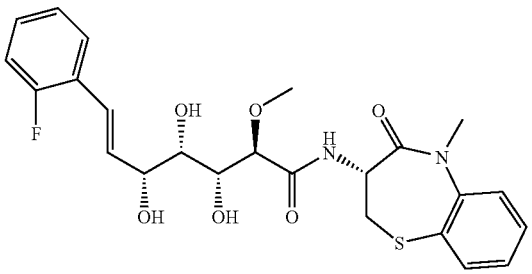 |
| Example 13 | 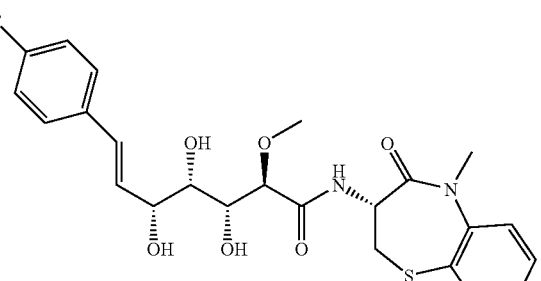 |
| Example 14 | 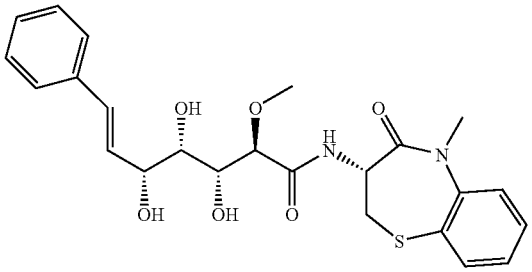 |
| Example 15 | 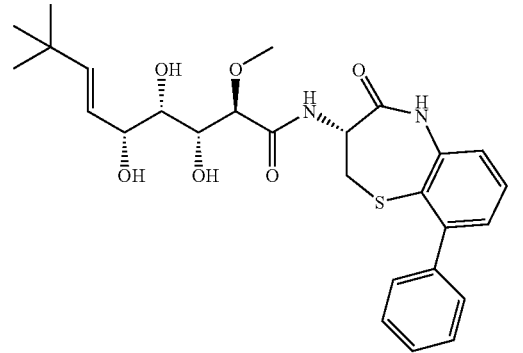 |

TABLE 1-continued

| Example | Structure |
|---|---|
| Example 16 | 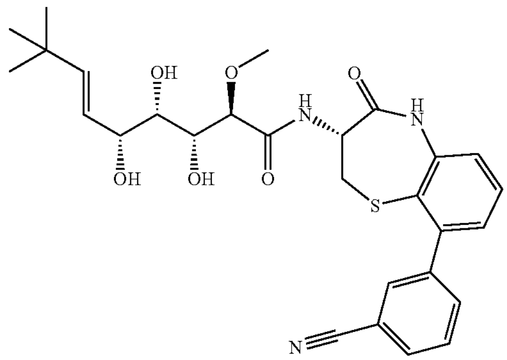 |
| Example 17 | 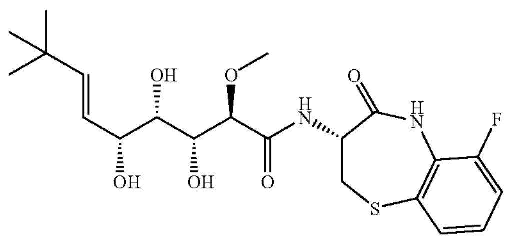 |
| Example 18 | 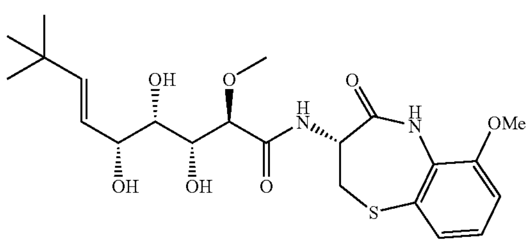 |
| Example 19 | 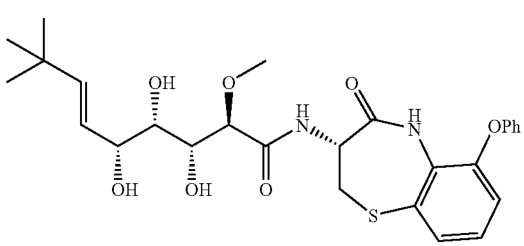 |
| Example 20 | 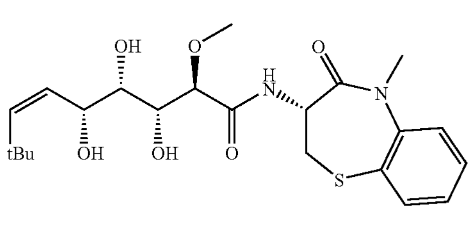 |

What is claimed is:

1. A compound of formula (I)

$$\text{(I)}$$

[Structure: R_1 with OH, OR_2, OH, OH substituents on chain, connected to C(=O)NH- to bicyclic system containing N-R_3, C=O, X, and phenyl ring with (R_4)_m]

wherein:
a) $R_1$ is independently selected from the group consisting of (C1-C12)alkyl, (C2-C12)alkenyl, (C2-C12)alkynyl, cycloalkyl, heterocyclyl, aryl, heteroaryl, cycloalkyl(C1-C12)alkyl, cycloalkyl(C2-C12)alkenyl, cycloalkyl(C2-C12)alkynyl, heterocyclyl(C1-C12)alkyl, heterocyclyl(C2-C12)alkenyl, heterocyclyl(C2-C12)alkynyl, aryl(C1-C12)alkyl, aryl(C2-C12)alkenyl, aryl(C2-C12)alkynyl, heteroaryl(C1-C12)alkyl, heteroaryl(C2-C12)alkenyl and heteroaryl(C2-C12)alkynyl, the aryl group of each $R_1$ being optionally substituted with one or more halogens;
b) $R_2$ is selected from the group consisting of (C1-C6)alkyl, aryl(C1-C6)alkyl, heteroaryl(C1-C6)alkyl, aryl, heteroaryl, (C1-C6)alkylthio(C1-C6)alkyl, di(C1-C6)alkylamino(C1-C6)alkyl, aryloxy(C1-C6)alkyl and (C1-C6)alkoxy(C1-C6)alkyl;
c) $R_3$ is selected from the group consisting of H, COO($R_5$), CONH($R_5$), CO($R_5$), O($R_5$) and $R_5$;
d) $R_4$ is independently selected from the group consisting of H, F, Cl, Br, N($R_5$)$_2$, NO$_2$, CN, COO($R_5$), CON($R_5$)$_2$, NHCO($R_5$), NHCOO($R_5$), OCONH($R_5$), O($R_5$) and $R_5$, or alternatively two substituents $R_4$, linked to two adjacent carbons of the phenyl, together form a ring chosen from cycloalkyl, heterocyclyl, aryl and heteroaryl, optionally substituted with one or more $R_4$;
e) m has the value 0, 1, 2, 3 or 4;
f) X is chosen from S, SO and SO$_2$;
g) $R_5$ is independently chosen from a non-bonding lone pair of electrons, H, (C1-C12)alkyl, (C2-C12)alkenyl, (C2-C12)alkynyl, halo(C1-C12)alkyl, aryl(C1-C12)alkyl, heteroaryl(C1-C12)alkyl, heteroarylaryl(C1-C12)alkyl, aryl, heteroaryl and cycloalkyl, in which each $R_5$ is optionally substituted with at least one substituent chosen from OH, halogen, (C1-C4)alkyl, (C1-C4)alkoxy, aryl(C1-C4)alkyl, aryl, heteroaryl(C1-C4)alkyl, heteroaryl, —N(CH$_3$)$_2$, —NH$_2$, CONH$_2$,

[Structures: morpholine, piperazine-Rz, pyrrolidine, diethylamine groups]

each of the Rz is independently selected from the group consisting of H, COO($R_5$), CONH($R_5$), CON($R_5$)$_2$, CO($R_5$) and $R_5$, in which each $R_5$ is independently chosen from (C1-C4)alkyl, halo(C1-C4)alkyl, aryl (C1-C4)alkyl and heteroaryl(C1-C4)alkyl, in which each $R_5$ is optionally substituted with a substituent chosen from OH, halogen, (C1-C4)alkyl, (C1-C4)alkoxy, aryl(C1-C4)alkyl, aryl, heteroaryl(C1-C4)alkyl and heteroaryl; or a pharmaceutically acceptable salt of such compound,
wherein heteroaryl is a monocyclic or polycyclic heteroaromatic substituent containing from 1 to 13 carbon atoms and from 1 to 4 heteroatoms selected from oxygen, sulphur, nitrogen and selenium, and
heterocyclyl is a saturated or partially unsaturated cyclic hydrocarbon based substituent containing from 1 to 13 carbon atoms and from 1 to 4 heteroatoms selected from oxygen, sulphur, nitrogen and selenium provided that when $R_1$ is (E) —CH=CH—C(CH$_3$)$_3$, $R_2$ is methyl, X is S and m is 0, then $R_3$ is other than a hydrogen atom, a (3,5-difluorophenyl)methyl group or a —CH$_2$—CH=CH$_2$ group.

2. A compound according to claim 1, wherein $R_1$ is chosen from —C($R_6$)=C($R_7$)($R_8$) in which $R_6$, $R_7$, and $R_8$ are independently selected from H, (C1-C6)alkyl, cycloalkyl, heterocyclyl, aryl and heteroaryl.

3. A compound according to claim 2 wherein $R_1$ is chosen from (E) —CH=CH—CH(CH$_3$)(C$_2$H$_5$), (E) —CH=CH—CH(CH$_3$)$_2$, and (E) —CH=CH—C(CH$_3$)$_3$.

4. A compound according to claim 2 wherein $R_1$ is chosen from (E) —C(CH$_3$)=CH—CH(CH$_3$)(C$_2$H$_5$), (E) —C(CH$_3$)=CH—CH(CH$_3$)$_2$, and (E) —C(CH$_3$)=CH—C(CH$_3$)$_3$.

5. A compound according to claim 1 wherein $R_2$ is methyl.

6. A compound according to claim 2 wherein $R_2$ is methyl.

7. A compound according to claim 1 wherein X is S.

8. A compound according to claim 2 wherein X is S.

9. A compound according to claim 1 wherein X is SO.

10. A compound according to claim 2 wherein X is SO.

11. A compound according to claim 1 wherein X is SO$_2$.

12. A compound according to claim 2 wherein X is SO$_2$.

13. A compound according to claim 1 wherein $R_3$ is independently chosen from methyl, a phenylmethyl group and a (3,5-difluorophenyl)methyl group.

14. A compound according to claim 1 wherein $R_3$ is H.

15. A compound according to claim 1 wherein $R_4$ is independently chosen from: F, Cl, Br, phenyl, cyanophenyl, trifluoromethyl, methoxy and phenoxy, or alternatively two substituents $R_4$, linked to two adjacent carbons of the phenyl, together form a pyrazine ring.

16. A compound according to claim 1 wherein m is 0.

17. A compound according to claim 1 which is
N-[(1R,3R)-5-(3,5-difluorobenzyl)-1,4-dioxo-2,3,4,5-tetrahydro-1,5-benzothiazepin-3-yl]-((6E)-(2R,3R,4S,5R)-3,4,5-trihydroxy-2-methoxy-8,8-dimethylnon-6-enamide;
N-[(1S,3R)-5-(3,5-difluorobenzyl)-1,4-dioxo-2,3,4,5-tetrahydro-1,5-benzothiazepin-3-yl]-((6E)-(2R,3R,4S,5R)-3,4,5-trihydroxy-2-methoxy-8,8-dimethylnon-6-enamide;
N-[(3R)-5-benzyl-4-oxo-2,3,4,5-tetrahydro-1,5-benzothiazepin-3-yl]-(6E) -(2R,3R,4S,5R)-3,4,5-trihydroxy-2-methoxy-8,8-dimethylnon-6-enamide;
N-[(3R)-5-methyl-4-oxo-2,3,4,5-tetrahydro-1,5-benzothiazepin-3-yl]-(6E) -(2R,3R,4S,5R)-3,4,5-trihydroxy-2-methoxy-8,8-dimethylnon-6-enamide;
N-((3R)-9-chloro-4-oxo-7-trifluoromethyl-2,3,4,5-tetrahydro-1,5-benzothiazepin-3-yl)-(6E) -(2R,3R,4S,5R)-3,4,5-trihydroxy-2-methoxy-8,8-dimethylnon-6-enamide;
N-((3R)-9-bromo-4-oxo-2,3,4,5-tetrahydro-1,5-benzothiazepin-3-yl)-(6E) -(2R,3R,4S,5R)-3,4,5-trihydroxy-2-methoxy-8,8-dimethylnon-6-enamide;

N-((3R)-8-chloro-4-oxo-2,3,4,5-tetrahydro-1,5-benzothiazepin-3-yl)-(6E) -(2R,3R,4S,5R)-3,4,5-trihydroxy-2-methoxy-8,8-dimethylnon-6-enamide; or (6E)-(2R,3R,4S,5R)-8-ethyl-3,4,5-trihydroxy-2-methoxy-N-((3R)-5-methyl-4-oxo -2,3,4,5-tetrahydro-1,5-benzothiazepin-3-yl)dec-6-enamide; or a pharmaceutically acceptable salt of such compound, or a hydrate or solvate of such compound or salt.

18. A compound according to claim 1 which is (2R,3R,4S,5R,6E)-7-cyclopentyl-3,4,5-trihydroxy-2-methoxy-N-[(3R)-5-methyl-4-oxo -2,3,4,5-tetrahydro-1,5-benzothiazepin-3-yl]hept-6-enamide;

(2R,3R,4S,5R,6E)-3,4,5-trihydroxy-2-methoxy-N-[(3R)-5-methyl-4-oxo-2,3,4,5-tetrahydro-1,5-benzothiazepin-3-yl]undec-6-enamide;

(2R,3R,4S,5R,6E)-7-cyclohexyl-3,4,5-trihydroxy-2-methoxy-N-[(3R)-5-methyl-4-oxo -2,3,4,5-tetrahydro-1,5-benzothiazepin-3-yl]hept-6-enamide;

(2R,3R,4S,5R,6E)-7-(2-fluorophenyl)-3,4,5-trihydroxy-2-methoxy-N-[(3R)-5-methyl-4-oxo-2,3,4,5-tetrahydro-1,5-benzothiazepin-3-yl]hept-6-enamide;

(2R,3R,4S,5R,6E)-7-(4-fluorophenyl)-3,4,5-trihydroxy-2-methoxy-N-[(3R)-5-methyl-4-oxo-2,3,4,5-tetrahydro-1,5-benzothiazepin-3-yl]hept-6-enamide;

(2R,3R,4S,5R,6E)-3,4,5-trihydroxy-2-methoxy-N-[(3R)-5-methyl-4-oxo-2,3,4,5-tetrahydro-1,5-benzothiazepin-3-yl]-7-phenylhept-6-enamide;

(2R,3R,4S,5R,6E)-3,4,5-trihydroxy-2-methoxy-8,8-dimethyl-N-[(3R)-4-oxo-9-phenyl -2,3,4,5-tetrahydro-1,5-benzothiazepin-3-yl]non-6-enamide;

(2R,3R,4S,5R,6E)-N-[(3R)-9-(3-cyanophenyl)-4-oxo-2,3,4,5-tetrahydro-1,5-benzothiazepin-3-yl]-3,4,5-trihydroxy-2-methoxy-8,8-dimethylnon-6-enamide;

(2R,3R,4S,5R,6E)-N-[(3R)-6-fluoro-4-oxo-2,3,4,5-tetrahydro-1,5-benzothiazepin-3-yl]-3,4,5-trihydroxy-2-methoxy-8,8-dimethylnon-6-enamide;

(2R,3R,4S,5R,6E)-3,4,5-trihydroxy-2-methoxy-N-[(3R)-6-methoxy-4-oxo-2,3,4,5-tetrahydro-1,5-benzothiazepin-3-yl]-8,8-dimethylnon-6-enamide;

(2R,3R,4S,5R,6E)-3,4,5-trihydroxy-2-methoxy-8,8-dimethyl-N-[(3R)-4-oxo-6-phenoxy -2,3,4,5-tetrahydro-1,5-benzothiazepin-3-yl]non-6-enamide; or (2R,3R,4S,5R,6Z)-3,4,5-trihydroxy-2-methoxy-8,8-dimethyl-N-[(3R)-5-methyl-4-oxo -2,3,4,5-tetrahydro-1,5-benzothiazepin-3-yl]non-6-enamide; or a pharmaceutically acceptable salt of such compound, or a hydrate or solvate of such compound or salt.

19. A compound according to claim 1 which is a) in non-chiral form, or b) in racemic form, or c) enriched in one stereoisomer, or d) enriched in one enantiomer;

and which is optionally salified.

20. A pharmaceutical composition comprising a compound according to claim 1 at at least one pharmaceutically acceptable excipient.

21. A process for preparing a compound according to claim 1 of formula (I) comprising the step of hydrolyzing a compound of formula (II)

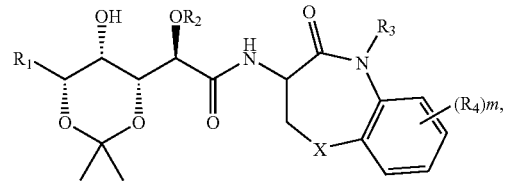

so as to obtain a compound of formula (I).

22. A process according to claim 21 further comprising the step of reacting a compound of formula (III)

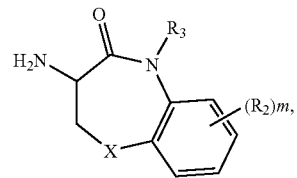

with a compound of formula (IV)

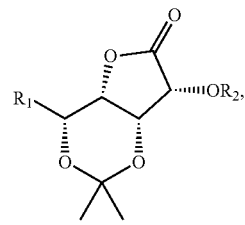

to give a compound of formula (II).

23. A process for preparing a compound according to claim 1 of formula (I) comprising the step of reacting a compound of formula (III)

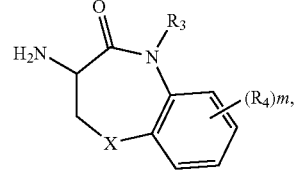

with a compound of formula (V)

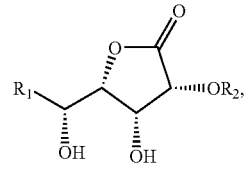

so as to obtain a compound of formula (I).

24. A process according to claim 23, further comprising the step of hydrolyzing a compound of formula (IV)

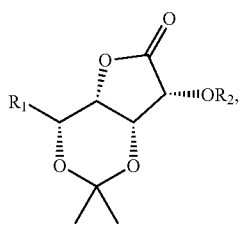

to give a compound of general (V)

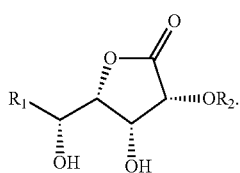

25. A process according to claim 23 comprising the step of reacting a compound of the formula

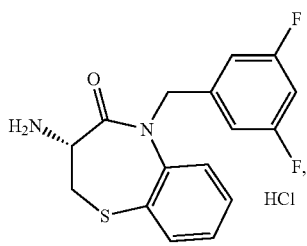

with a compound of the formula

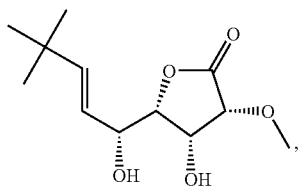

in order to obtain a compound of the formula

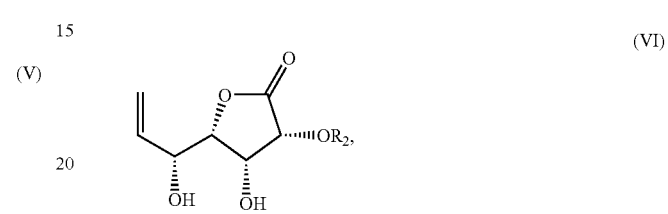

26. A process according to claim 23 further comprising the steps of hydrolyzing a compound (VII)

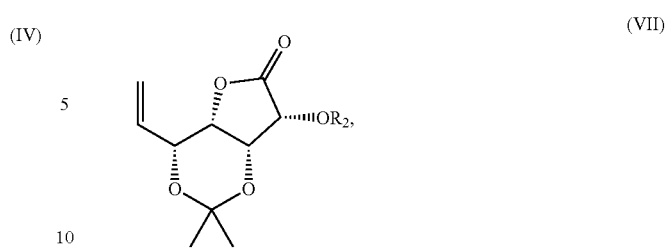

in order to obtain a compound of formula (VI)

and then subjecting the compound of formula (VI) to metathesis to obtain a compound of formula (V)

wherein $R_1$ represents —CH=CH—$R'_1$ and $R'_1$ represents a (C1-C6)alkyl, cycloalkyl, heterocyclyl, aryl or heteroaryl group.

27. A process according to claim 26 further comprising the step of subjecting a compound of formula (VIII)

to a double dehydration to obtain a compound of formula (VII)

28. A compound of formula (II)

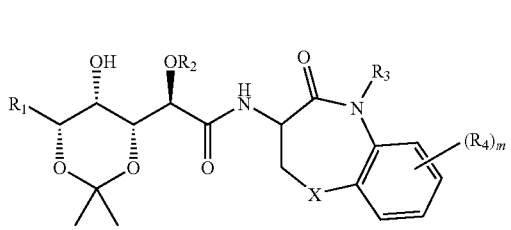

wherein:
- R₁ is independently selected from the group consisting of (C1-C12)alkyl, (C2-C12)alkenyl, (C2-C12)alkynyl, cycloalkyl, heterocyclyl, aryl, heteroaryl, cycloalkyl(C1-C12)alkyl, cycloalkyl(C2-C12)alkenyl, cycloalkyl(C2-C12)alkynyl, heterocyclyl(C1-C12)alkyl, heterocyclyl(C2-C12)alkenyl, heterocyclyl(C2-C12)alkynyl, aryl (C1-C12)alkyl, aryl(C2-C12)alkenyl, aryl(C2-C12)alkynyl, heteroaryl(C1-C12)alkyl, heteroaryl(C2-C12)alkenyl and heteroaryl(C2-C12)alkynyl, the aryl group of each R₁ being optionally substituted with one or more halogens;
- R₂ is selected from the group consisting of (C1-C6)alkyl, aryl(C1-C6)alkyl, heteroaryl(C1-C6)alkyl, aryl, heteroaryl, (C1-C6)alkylthio(C1-C6)alkyl, di(C1-C6)alkylamino(C1-C6)alkyl, aryloxy(C1-C6)alkyl and (C1-C6)alkoxy(C1-C6)alkyl;
- R₃ is selected from the group consisting of H, COO(R₅), CONH(R₅), CO(R₅), O(R₅) and R₅;
- R₄ is independently selected from the group consisting of H, F, Cl, Br, N(R₅)₂, NO₂, CN, COO(R₅), CON(R₅)₂, NHCO(R₅), NHCOO(R₅), OCONH(R₅), O(R₅) and R₅, or alternatively two substituents R₄, linked to two adjacent carbons of the phenyl, together form a ring chosen from cycloalkyl, heterocyclyl, aryl and heteroaryl, optionally substituted with one or more R₄;
- m has the value 0, 1, 2, 3 or 4;
- X is chosen from S, SO and SO₂;
- R₅ is independently chosen from a non-bonding lone pair of electrons, H, (C1-C12)alkyl, (C2-C12)alkenyl, (C2-C12)alkynyl, halo(C1-C12)alkyl, aryl(C1-C12)alkyl, heteroaryl(C1-C12)alkyl, heteroarylaryl(C1-C12)alkyl, aryl, heteroaryl and cycloalkyl, in which each R₅ is optionally substituted with at least one substituent chosen from OH, halogen, (C1-C4)alkyl, (C1-C4)alkoxy, aryl(C1-C4)alkyl, aryl, heteroaryl(C1-C4)alkyl, heteroaryl, —N(CH₃)₂, —NH₂, CONH₂,

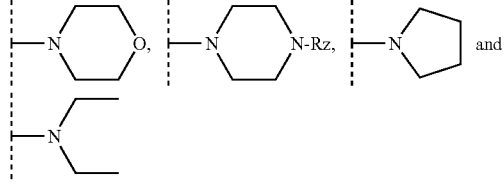

each of the Rz is independently selected from the group consisting of H, COO(R₅), CONH(R₅), CON(R₅)₂, CO(R₅) and R₅, in which each R₅ is independently chosen from (C1-C4)alkyl, halo(C1-C4)alkyl, aryl (C1-C4)alkyl and heteroaryl(C1-C4)alkyl, in which each R₅ is optionally substituted with a substituent chosen from OH, halogen, (C1-C4)alkyl, (C1-C4)alkoxy, aryl(C1-C4)alkyl, aryl, heteroaryl(C1-C4)alkyl and heteroaryl; or a pharmaceutically acceptable salt of such compound,
wherein heteroaryl is a monocyclic or polycyclic heteroaromatic substituent containing from 1 to 13 carbon atoms and from 1 to 4 heteroatoms selected from oxygen, sulphur, nitrogen and selenium, and heterocyclyl is a saturated or partially unsaturated cyclic hydrocarbon based substituent containing from 1 to 13 carbon atoms and from 1 to 4 heteroatoms selected from oxygen, sulphur, nitrogen and selenium provided that when R₁ is (E) —CH═CH—C(CH₃)₃, R₂ is methyl, X is S, m is 0, then R₃ is other than a hydrogen atom, a —CH₂—CH═CH₂ group, or a (3,5-difluorophenyl) methyl group.

29. A compound of formula (III)

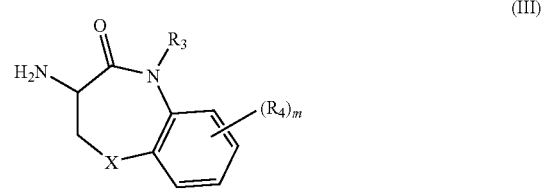

wherein X is S; R₃ is H; methyl; phenylmethyl or (3,5-difluorophenyl)methyl; R₄ is F, Cl, Br, phenyl, cyanophenyl, trifluoromethyl, methoxy or phenoxy; and m is 0, 1, 2, 3 or 4;
provided that when m is 0 and X is S, then R₃ is other than a hydrogen atom or a (3,5-difluorophenyl)methyl group; and
provided that when X is S and R₃ is phenylmethyl, the R₄ is other than trifluoromethyl or methoxy.

30. The compound according to claim 1 wherein heteroaryl is pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl.

31. The compound according to claim 1 where heterocyclyl is a saturated or partially unsaturated hydrocarbon based substituent which is monoocyclic and contains 4 or 5 carbon atoms and 1 to 3 heteroatoms.

32. The compound according to claim 28 wherein heteroaryl is pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl.

33. The compound according to claim 1 where heterocyclyl is a saturated or partially unsaturated hydrocarbon based substituent which is monoocyclic and contains 4 or 5 carbon atoms and 1 to 3 heteroatoms.

* * * * *